United States Patent
Bier

(10) Patent No.: US 8,395,112 B1
(45) Date of Patent: Mar. 12, 2013

(54) MASS SPECTROMETER AND METHOD FOR USING SAME

(76) Inventor: Mark E. Bier, Pittsburgh, PA (US)

( * ) Notice: Subject to any disclaimer, the term of this patent is extended or adjusted under 35 U.S.C. 154(b) by 24 days.

(21) Appl. No.: 12/898,264

(22) Filed: Oct. 5, 2010

Related U.S. Application Data

(63) Continuation-in-part of application No. 11/903,018, filed on Sep. 20, 2007, now Pat. No. 7,807,963.

(60) Provisional application No. 60/846,020, filed on Sep. 20, 2006.

(51) Int. Cl.
*H01J 49/34* (2006.01)
*B01D 59/44* (2006.01)

(52) U.S. Cl. .......................... 250/281; 250/282; 250/291

(58) Field of Classification Search .......... 250/281–282, 250/290–292, 298
See application file for complete search history.

(56) References Cited

U.S. PATENT DOCUMENTS

| | | | |
|---|---|---|---|
| 3,065,640 A | 11/1962 | Langmuir et al. | |
| 4,642,165 A | 2/1987 | Bier | |
| 4,791,292 A | 12/1988 | Cooks et al. | |
| 4,885,500 A | 12/1989 | Hansen et al. | |
| 5,026,987 A | 6/1991 | Bier et al. | |
| 5,162,650 A | 11/1992 | Bier | |
| 5,420,425 A * | 5/1995 | Bier et al. | 250/292 |
| 5,420,549 A | 5/1995 | Prestage | |
| 5,521,379 A * | 5/1996 | Franzen et al. | 250/282 |
| 5,572,022 A | 11/1996 | Schwartz et al. | |
| 5,640,010 A | 6/1997 | Twerenbold | |
| 5,679,950 A * | 10/1997 | Baba et al. | 250/281 |
| 5,747,801 A * | 5/1998 | Quarmby et al. | 250/292 |
| 5,750,993 A | 5/1998 | Bier | |
| 5,756,996 A | 5/1998 | Bier et al. | |
| 5,763,878 A | 6/1998 | Franzen | |
| 5,783,824 A * | 7/1998 | Baba et al. | 250/281 |
| 6,075,244 A * | 6/2000 | Baba et al. | 250/292 |
| 6,107,627 A * | 8/2000 | Nakagawa et al. | 250/292 |
| 6,489,609 B1 * | 12/2002 | Baba et al. | 250/282 |
| 6,566,651 B2 * | 5/2003 | Baba et al. | 250/281 |
| 6,710,334 B1 | 3/2004 | Twerenbold | |
| 6,737,641 B2 * | 5/2004 | Kato | 250/281 |
| 6,777,673 B2 * | 8/2004 | Chang et al. | 250/290 |

(Continued)

FOREIGN PATENT DOCUMENTS

CA 2196291 2/1996

OTHER PUBLICATIONS

Frankevich, V. et al., "Laser-induced fluorescence of trapped gas-phase molecular ions generated by internal-source matrix assisted laser desorption/ionization in a Fourier transform ion cyclotron resonance mass spectrometer," Eur. J. Mass. Spectrom. 11, 475-482 (2005).*

(Continued)

*Primary Examiner* — David A Vanore
*Assistant Examiner* — Wyatt Stoffa
(74) *Attorney, Agent, or Firm* — David G. Oberdick; Peter J. Borghetti

(57) ABSTRACT

Apparatus including an ion trap, a controller connected to the ion trap, wherein the controller includes a memory containing computer readable instructions which, when executed, cause the controller to send control signals to the ion trap so that the ion trap produce and maintain a trapping field in the ion trap, a waveform generator to change the trapping field so that ions of a predetermined mass in the trapping chamber are selectively moved; a secondary waveform generator to change the orbits of the ions; an energy source to excite ions to emit photons, an optical detector to detect the emitted photons, and a processor which can apply fast-Fourier transform analysis of the time-domain signal of the detected emitted photons to generate a frequency or mass spectrum related to mass-to-charge ratio of the ions.

28 Claims, 45 Drawing Sheets

U.S. PATENT DOCUMENTS

| | | | |
|---|---|---|---|
| 7,019,285 B2 | 3/2006 | Dresch et al. | |
| 7,081,617 B2* | 7/2006 | McLean et al. | 250/283 |
| 7,119,331 B2* | 10/2006 | Chang et al. | 250/292 |
| 7,161,147 B1* | 1/2007 | Chang et al. | 250/292 |
| 7,645,987 B2* | 1/2010 | Chang et al. | 250/288 |
| 7,807,963 B1* | 10/2010 | Bier | 250/283 |
| 2003/0052264 A1* | 3/2003 | Baba et al. | 250/281 |
| 2003/0122070 A1* | 7/2003 | Chang et al. | 250/292 |
| 2005/0029448 A1* | 2/2005 | Chang et al. | 250/292 |
| 2005/0092919 A1* | 5/2005 | Bellec et al. | 250/290 |
| 2005/0118650 A1* | 6/2005 | Dasseux et al. | 435/7.2 |
| 2005/0189485 A1* | 9/2005 | McLean et al. | 250/287 |
| 2006/0284074 A1* | 12/2006 | Chang et al. | 250/288 |
| 2007/0131871 A1* | 6/2007 | Chang et al. | 250/427 |
| 2008/0035858 A1* | 2/2008 | Hegazi | 250/461.1 |
| 2009/0078861 A1* | 3/2009 | Hill et al. | 250/282 |
| 2009/0084979 A1* | 4/2009 | DeWalch | 250/458.1 |
| 2009/0218481 A1* | 9/2009 | Dewalch | 250/281 |

OTHER PUBLICATIONS

Cooley, J., An Algorithm for the Machine Calculation of Complex Fourier Series, Mathematics of Computations, vol. 19, No. 90, pp. 297-301 (1965).*

Makarov, A., "Electrostatic Axially Harmonic Orbital Trapping: A High Performance Technique of Mass Analysis" Anal. Chem. 2000, 72, 1156-1162.*

Cai, Y. et al., Optical Detection and Charge-State Analysis of MALDI-Generated Particles with Molecular Masses Larger Than 5 MDa, Analytical Chemistry, Sep. 1, 2002, pp. 4434-4440, vol. 74, No. 17, Published on Web Jul. 26, 2002.

Quadrupole ion trap, http://en.wikipedia.org/wiki/Quadrupole_ion_trap, printed May 9, 2006, 3 pgs.

Quadrupole mass analyzer, http://en.wikipedia.org/wiki/Quadrupole_mass_analyzer, printed May 9, 2006, 2 pgs.

Mass spectrometry, http://en.wikipedia.org/wiki/Quadrupole_mass_spectrometer, printed May 9, 2006, 12 pgs.

Mass Spectrometer, http://hyperphysics.phy-astr.gsu.edu/hbase/magnetic/maspec.html, printed May 9, 2006, 4 pgs.

The Mass Spectrometer, http://www.chemguide.co.uk/analysis/masspec/howitworks.html, printed May 9, 2006, 8 pgs.

Wuerker, R.F. et al., Electrodynamic Containment of Charged Particles, Journal of Applied Physics, Mar. 1959, pp. 342-349, vol. 30, No. 3.

Bier, Mark E., et al., Electrospray-Ionization Quadrupole Ion-Trap Mass Spectrometry, Electrospray-Ionization Mass Spectrometry, Chapter 7, pp. 235-289, 1997, John Wiley & Sons.

Nie, Zongxiu, et al., Microscopy-Based Mass Measurement of a Single Whole Virus in a Cylindrical Ion Trap, Angew. Chem. Int. Ed. 2006, 45: 8131-8134, Wiley InterScience.

Schatz, T. et al., Crystalline ion beams, Nature, vol. 412, Aug. 16, 2001, pp. 717-720, MacMillan Magazines Ltd.

Marshall, A.G. et al., Tailored Excitation for Fourier Transform Ion Cyclotron Resonance Mass Spectrometry, J. Am. Chem. Soc. 1985, 107, pp. 7893-7897.

Marshall, A.G. et al., Fourier Transform Ion Cyclotron Resonance Mass Spectrometry: A Primer, Mass Spectrometry Reviews, 1998, 17, pp. 1-35, John Wiley & Sons Inc.

Schlemmer, S., et al., Nondestructive high-resolution and absolute mass determiniation of single charged particles in a three-dimensional quadrupole trap, J. Applied Physics, vol. 90, No. 10, pp. 5410-5418, Nov. 15, 2001, American Institute of Physics.

Wen-Ping, P., et al., Optical Detection Methods for Mass Spectrometry of Macroions, Mass Spectrometry Reviews, 2004, 23, pp. 443-465, Wiley Periodicals, Inc.

Office Action for U.S Appl. No. 11/903,018 dated Aug. 31, 2009.

* cited by examiner

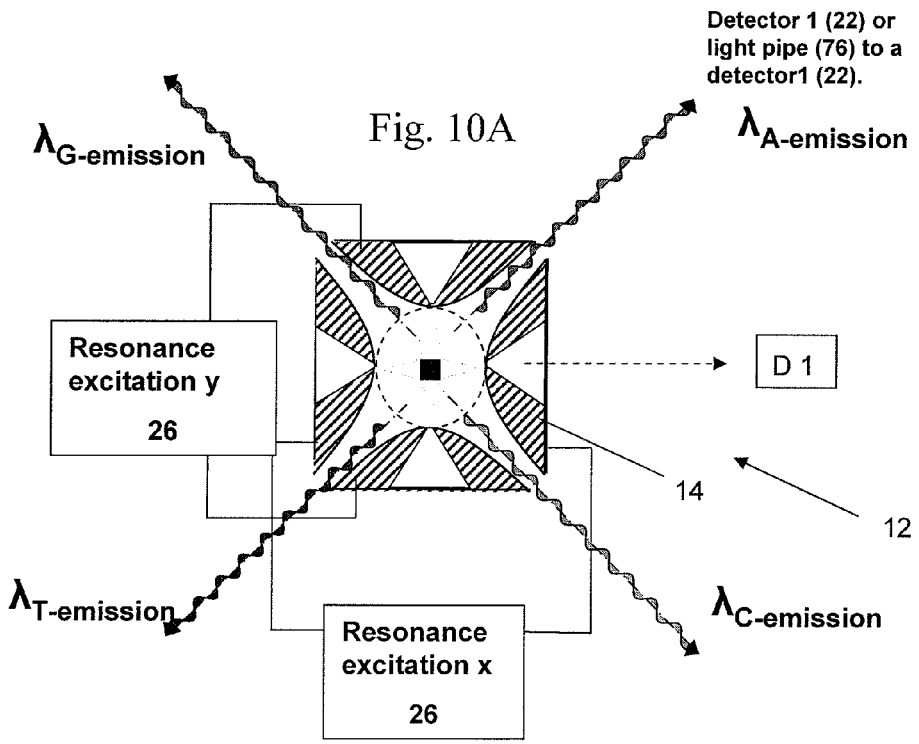
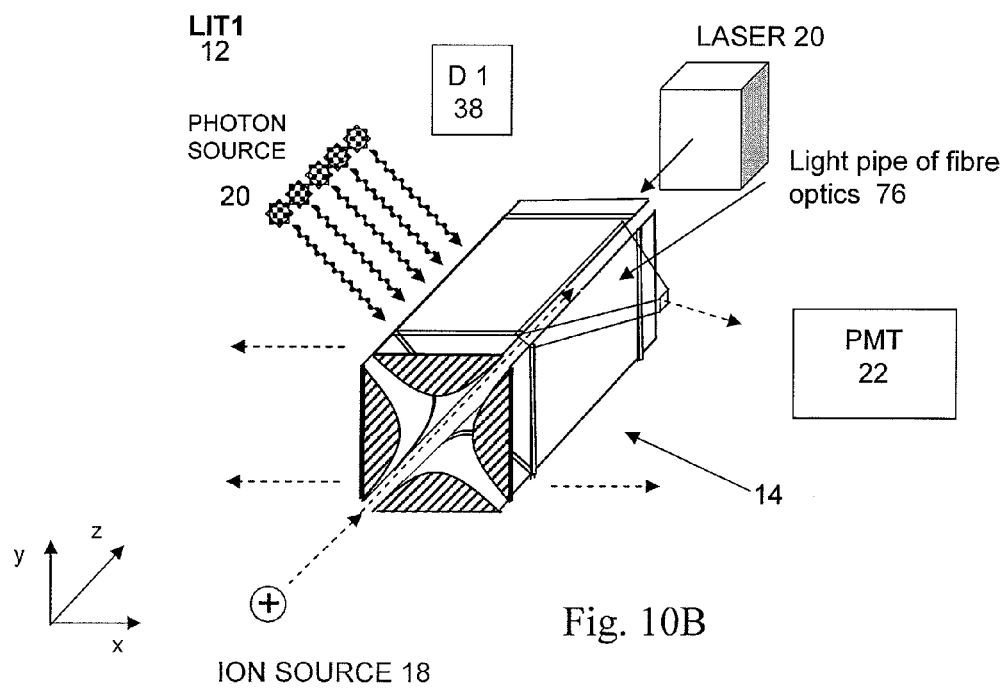

Ion orbit along FTMS trapping cell a.

b.

Frequency of axial oscillations = $\omega = [(z/m)k]^{1/2}$

1. Heavy virus ion

Human poliovirus 1 strain mahoney, 2plv

React with dye

2. Heavy ion tagged with a fluorescent dye.

A

3. Protein complexes of lower m/z

Resonance excitation in y and x dimensions. Areas of possible exposure by the excitation source for LIF are shown at points a. thru f.

Resonance excitation only in y dimension

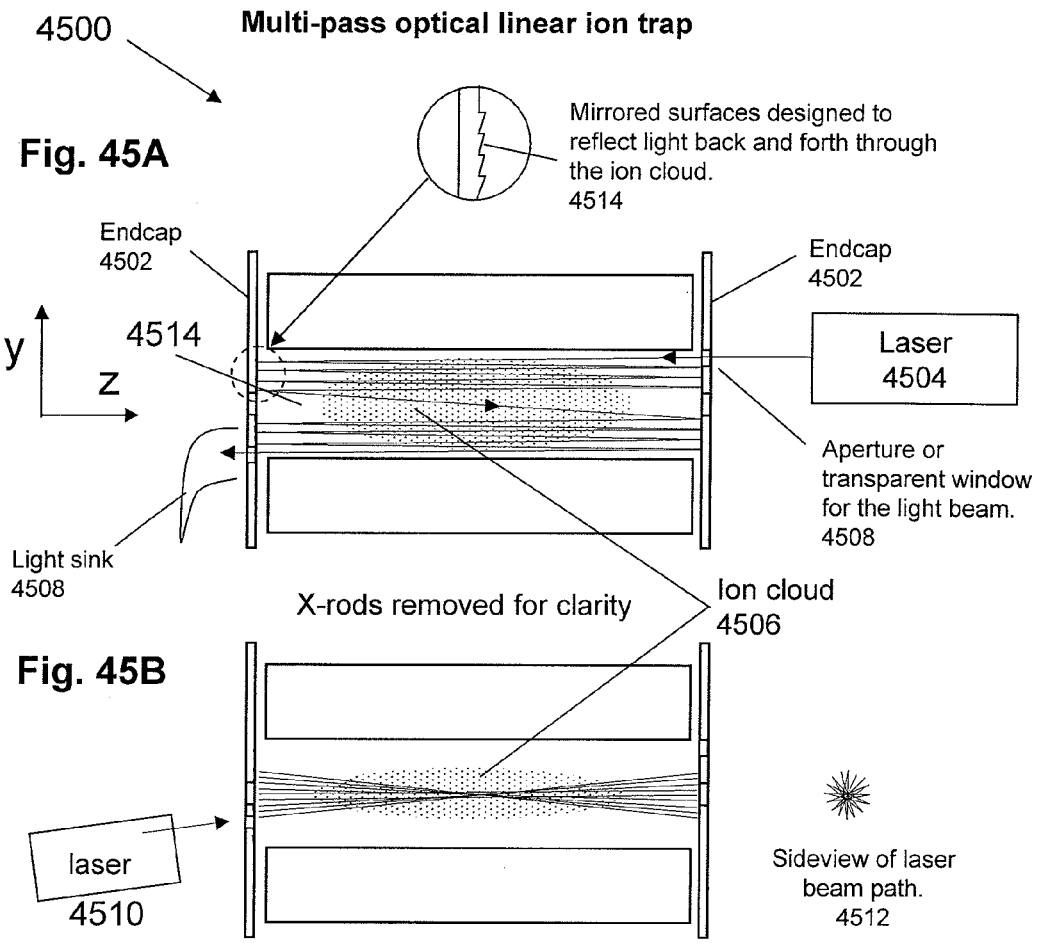
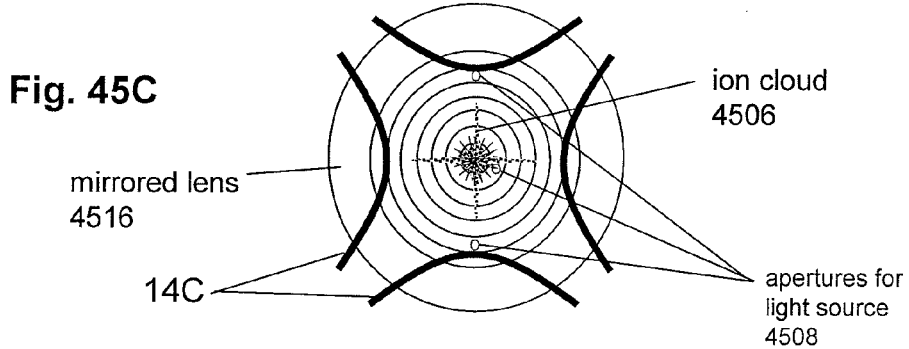
view down the z-axis with the front endcap removed for clarity.

SEQUENCE LISTING

```
<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<223> OTHER INFORMATION: arbitrary sequence to illustrate dna sequencing
      by an apparatus according to the present invention

<400> SEQUENCE: 1
gggaaccttg ctaactcagg ctcgat                                          26
```

MASS SPECTROMETER AND METHOD FOR USING SAME

CROSS-REFERENCE TO RELATED APPLICATIONS

This application is a continuation in part application of U.S. Ser. No. 11/903,018, titled METHOD AND APPARATUS FOR AN IMPROVED MASS SPECTROMETER, filed Sep. 20, 2007 (now U.S. Pat. No. 7,807,963, issued on Oct. 5, 2010), which claims priority from U.S. Provisional Patent Application No. 60/846,020, filed Sep. 20, 2006, which are both incorporated herein by reference.

FIELD OF THE INVENTION

The present invention is directed generally to a mass spectrometer and a method apparatus for using same.

BACKGROUND OF THE INVENTION

Many different mass analyzers are used in the field of mass spectrometry. The most common mass analyzers include ion-cyclotron resonance (ICR) or Fourier transform mass spectrometer ("FTMS"), ion traps, quadrupole, time-of-flight, orbitraps and magnetic sector instruments. All of the commercial versions of these instruments detect the ions by using an ionizing particle detector or by measuring an electrical image current as done when using the Fourier transform technique for FTMS and the orbitrap. Although there has been experimental work using photon emission to make ion measurements inside an ion trap, no known commercial instrument with any of the above mentioned mass analyzer types use optical detection of ions inside the mass analyzer to determine the m/z and/or the presence of select chromophores. In the pioneering work of, Wuerker, Shelton and Langmuir in 1959, they used a 3D-quadrupole field ion trap or what is often now called a "Paul" trap to teach how charged aluminum particles could be confined and photographed in dynamic equilibrium. They applied a voltage across the end caps of the ion trap to measure the resulting frequency of the charged particles at resonance and recorded interesting tell tale photographs of the charged particle trajectories. Holes were machined in the ion trap electrodes to make these observations and when the particles reached a stable orbit they noted the voltage and frequencies applied to the electrodes. They used a conventional 35 mm microscope camera and exposed the film for 0.1-0.2 seconds. They did not purposely move the ions to specific locations in the trap to image or photon count or count from specific regions of the ion trapping volume, but instead they scanned the RF or resonant frequency for mass analysis and recorded for the first time, the complete motion of the trapped charged particles in the ion trapping chamber. Others have since followed Wuerker, Shelton and Langmuir's work and have used improved light sources, such as lasers; detectors, such as photo multiplier tubes; different analyzers and optical techniques such as laser induced fluorescence (LIF) to make improved measurements. In 1975, LIF of a non trapped molecular ion was first reported for $N_2^+$ by Engelking and Smith. In 1977, Miller and Bondybey followed by showing the LIF of non-trapped $CO^+$ and $CO_2^+$ and later with Sears, in 1978-81, of various fluorinated benzene cations. Between 1980-82 $CD^+$ and $BrCN^+$ and $N_2^+$ were trapped for the LIF measurements using a Paul trap by Grieman, Mahan and O'Keefe. There have also been reports of LIF in Penning ion traps by Drullinger and others. Welling, Thompson and Walther in 1996 [IJMSIP, 172, p95.] used a linear ion trap (LIT) to determine the absolute gas phase photo dissociation cross-section of the ionic molecular complexes. They made complexes of $MgC_{60}^+$ by in situ collisions inside the LIT and then dissociated them using a laser shot off-axis. The resultant signal was recorded using mass spectrometry or by using laser induced fluorescence (LIF) of the $Mg^+$ product ion. Welling, Schuessles, Thompson and Walther followed those experiments in 1998 to study ion molecule reactions in the gas phase and again used optical spectroscopy on the trapped ions in a LIT. They used parametric excitation of the secular motion to generate the mass spectrum with ejection amplitudes of 1 $V_{pp}$ and scan rates of 200 $kHzs^{-1}$. They calculated that they trapped $10^6$ ions in a 10 cm long trapping volume which facilitated the spectroscopy measurements even with an off-axis laser and detector. Co-linear excitation was not done. They measured total cross-sections of $MgC_{60}^+$ by LIF and photo-dissociation. Photons from the strong LIF transition from $Mg^+$ were detected perpendicular to the ion axis in a pump probe approach. In these studies they did not do mass analysis using LIF. In 2001, Wang, Hendrickson and Marshall reported on LIF optical measurements of hexafluorobenzene from inside an ion cyclotron resonance mass spectrometer, but they did not use LIF for mass analysis.

Nakamura and coworkers [JAP 2001, 89, 2922], measured various resonances in a linear combined trap in 2001 and measured these frequencies by using a fast Fourier transform method.

In 2001, Schlemmer, Illemann, Wellert and Gerlich [JAP, 90, p5410] demonstrated mass spectrometry of 500 μm $SiO_2$ particles in a Paul-like trap using a light scattering nondestructive method. Their ion trap used end caps, but the field in the r-dimension was generated by eight rods to allow for good penetration of the laser beam into the trap and thus they did not incorporate a ring electrode. In this experiment the particles were illuminated inhomogeneously so that the scattered light would be modulated at the secular frequency of the charged particles trajectories thus allowing the calculation of the m/z using a fast Fourier transform. The laser beam density was used to achieve this measurement and a photodiode detector was used to detect the photon emissions.

In 2002, Khoury, Rodriguez-Cruz and Parks used electrospray ionization (ESI) and a Paul trap to make pulsed fluorescence measurements of trapped molecular ions for rhodamine 640 and Alexa Fluor 350. For ion trapping during ion injection, the helium was pulsed to $2 \times 10^4$ Torr for 0.25 to 0.5 seconds. Their calculations showed that for $10^3$ trapped ions, approximately 1% of these were detected by photon emissions through a hole in the ring electrode. The low percentage of ions detected per pulse was partially due to a maximum laser beam overlap of 3-15% of the ion cloud and the detection of the photons emitted through a 1.2 mm hole to the photomultiplier. They were able to eliminate background laser scattering during the pulse by delaying the measurement which greatly improved the signal-to-noise level. Measurements were taken over minute exposure times. They did not use the LIF signal to determine m/z. In 2003, Danell and Parks showed that fluorescence resonance energy transfers (FRET) measurement can be made on oligonucleotides duplexes in an ion trap using spectroscopy and a 3D-quadrupole field ion trap. They stressed that the elimination of background scattered radiation at the detector was essential to make their measurements.

Baba and Waki studied the sympathetic cooling rate of gas-phase ions in linear ion traps in 2002. In their experiment a laser beam was directed on-axis in the LIT. Marshal et al.

determined fluorescence lifetimes of ions in a Penning trap and demonstrated the feasibility of resolving these ions from a heterogeneous mixture.

In 2003, Cai, Peng and Chang used a dual Paul trap to do LIF on labeled polystyrene particles. The first trap was used to trap all the charged particles while the second trap received select particles from the first and was used for LIF. They used a frequency scan from 0.5 Hz to 50 kHz for mass analysis. Particles up to 27 nm were analyzed by this method as well as fluorescently labeled IgG at 150 kDa. In 2005, Peng, Yang, Lin and Chang showed high precision mass determination for single polystyrene spheres using a Paul trap [Anal. Chem., 2005, 77, 7084.]. In these experiments they used a single trap and monitored the star like trajectory pattern to determine the mass following Hars and Tass [JAP 1995, 77 p4245.].

And finally, Iavarone, Meinen, Schulze and Parks made fluorescence measurements to probe peptide conformations in their Paul ion trap and did the mass analysis using conventional methods.

BRIEF SUMMARY OF THE INVENTION

This invention teaches improved methods and apparatuses for selective mass analysis of ions by measuring the photons emitted from ions in an "optical" mass spectrometer. Laser induced fluorescence (LIF) or light scattering are two processes that could be used to make such an optical measurement. The invention should improve resolution, mass accuracy, detection limits and sensitivity with efficient photon excitation and simultaneous measurement of the frequency and intensity of ion fluorescence from an ensemble of trapped ions. The secular frequencies of all the stored fluorescing ions can be measured at once by detecting the frequency of the photons emitted after inhomogeneous laser excitation of the trapped ion volume or individually by moving the select ion or ions into the measurement region. Additionally, unique fluorescent tag molecules with specific excitation and emission frequencies may be chosen. Efficient photon excitation can be accomplished by using lasers, large excitation volumes with a large cross-section and long absorption path lengths, mirrors and strong fluorescent tag molecules. Fluorescent tag molecules may not be needed if the ion already fluoresces. Efficient photon detection can be accomplished by using an optical trap with light pipes, reflective or transparent electrodes and focusing light optics so that the maximum number of photons can be detected and measured. The detection scheme allows the same set of ions to be mass analyzed repetitively and without ion loss. That is, ions do not require ejection from the device for LIF or light scattering mass analysis and an array of "optical traps" could be used to extend the analysis time per ion packet while not limiting the frequency of ion sampling. The ion trapping volumes should be large, such as found in a linear ion trap, so that a large number of ions can be trapped without the deleterious effects of space-charge and so that a long path length exists for ion excitation and the emitted photons should be measured so that they can be recorded in the absence of scattered light noise. An optical horn can be used to trap the laser light to avoid backscattering. Many different fluorescent tag molecules, lasers, filter and detectors can be used for the select analysis and an example will be explained in detail in a later section. Ions can me selectively resonated into or out of the laser beam or beams for specific scan modes. The frequency of the modulated photon signal collected at a photo multiplier tube over time from all the ions or a select set of resonating ions can be analyzed using a fast Fourier transform (FFT) to create the mass spectrum (frequency spectrum). An imaging array detector such as a charge coupled device (CCD) can be used so that either the total photon signal at the array can be measured or the individual photon signals collected at an individual pixel of the detector of an imaging array may undergo a FFT analysis. The focus of the invention as describe here is on ion trap mass spectrometers that use two-dimensional (2D)-quadrupole fields, but other ion "trapping" mass analyzer may be employed including a three-dimensional (3D) quadrupole field ion traps, a Fourier transform mass spectrometer, a Penning trap and an orbitrap. Other ion traps with electrode shapes with rectilinear or cylindrical geometry would apply.

Ion imaging of the trapped ions can also be used for mass analysis, to determine ion position, to determine the photon emission frequency of an ion, to study ion/molecule and/or ion/ion reactions, to study ion mobility and to study ion behavior in an ion trap. Large trapping volumes of some mass analyzers would be ideal for these measurements because of the increased photon signal density that would result. In this measurement scheme the m/z, the position and the color (frequency of light emitted) of the ions could be determined for each pixel of an imaging detector array.

As mentioned above ion/ion or ion/molecule reactions could be followed inside an optical ion trap and used to make ions optically visible. Such reactions might be used to add a chromophore to a select functional group of the trapped ions so that the ion will "light up" revealing that it had such a group. For example, such a reaction could be used to determine if a peptide was phosphorylated or what amino acid was phosphorylated after mass spectrometry/mass spectrometry (MS/MS) analysis. Another example of using a chromophore reaction in the mass spectrometer would be to add on a tag molecule so that it can be observed for a mass measurement. Ion/Ion reaction using positive (+) and negative (−) reactant ions would be especially efficient due to the opposite charge states making an increased reaction cross-section. In some cases the emission frequency may be shifted, reduced in amplitude or stopped after the reaction.

Several other applications of the invention describe here could benefit from the mass analysis improvement. For example, the invention could be a method and apparatus used to mass analyze large molecules above 100 kDa (Mega Daltons to Giga Daltons) where conventional mass detectors have a reduce signal or fail because they are mass and ion velocity dependent. For example, macromolecular ions do not give a strong signal response from conventional ionizing detectors. This invention combined with photo dissociation could also be a method to study fragmentation of these ions. The method may require the incorporation of a fluorescent tag molecule or molecules. The tag molecule contains a chromophore that absorbs the light from the excitation source. The tag molecule will emit a photon at another wavelength that can be detected by a photon multiplier tube (PMT). In this way the m/z of the tagged ion can be followed optically.

The invention could also be used to determine adduct association of various species. In a fluorescence resonance energy transfer (FRET) experiment, two different fluorescent molecules are used to measure the binding strength between, two molecules. For example, to study a protein-protein association, one protein is bound with an acceptor molecule while the other is bound with a donor molecule. When the two proteins come together (<10 nm) the strength of the interaction may be determined by the intensity of the emitted photon signal of the acceptor.

A gas phase measurement similar to the differential in-gel electrophoresis (DIGE) technique could also be done to determine the m/z and abundance for different proteins and peptides for two or more different cell populations. This experiment involves at least two different fluorescent tag molecules in the analysis.

Gas phase DNA sequencing is another application of the optical ion trap where DNA fluorescently tagged ions could be detected to determine the terminal A, T, G or C nucleotide and m/z. Unique tag molecules, lasers and filters could be used to determine the nucleotide and these lasers could be uniquely modulated or timed to uniquely identify each signal.

Many variations are possible with the present invention. These and other teachings, variations, and advantages of the present invention will become apparent in the detailed description of the invention section.

Use of optical detection can greatly improve the measurement of some m/z. This invention shows how using new ion trapping geometries with unique excitation and emission optical measurement schemes should greatly improve the sensitivity, resolution and mass accuracy of these optical mass spectrometers so that they can be routinely performed. This invention combines optical devices such as bright light sources and lasers that excite the maximum number of ions along long absorption paths or areas which is possible in larger ion trapping volumes and unique photon measuring devices and methodologies to capture the maximum number of photons emitted. In concert, different inhomogeneous excitation and measurement schemes are taught which will allow for the excitation of a unique set of ions as determined by the waveforms applied to the electrodes, the light sources, the m/z and excitation frequency of the ions. The invention shows how the improvement can be obtained by trapping, exciting and detecting the maximum number of ions so that the improved resolution, mass accuracy and sensitivity for those charged particles can be obtained.

Large 2D quadrupole field trapping volumes that can be applied to this work were taught by Bier et al. (U.S. Pat. No. 5,420,425), but 3D quadrupole field ion trap and other ion trapping fields can be applied. The frequency of the ions can be measured directly using FFT analysis and these frequencies related directly back to the m/z of the ions. The ion frequencies can be measured near the center of the LIT or under the influence of resonance excitation signals applied to the end caps of a 3D trap or rods of a LIT. In some cases moving the ions to select regions of a large ion trapping volume, the unique m/z is measured by the photon emission without the interference of the other ions or simultaneously with other light measurements of other regions of the ion trap. In the orbitrap or the FTMS cell, the laser is directed so that it excites the ions during each orbit (or axial motion in the orbitrap). The frequency and intensity of the photons emitted can be used to determine the m/z of the selected ions inside the trapping device using improved optics and measurement schemes as described.

Several advantages of the optical LIT are realized. i.) no ion ejection slots in the rods are required allowing for the formation a near perfect quadrupolar field. ii.) This also means that even larger (longer in the z-dimension for the LIT) ion trapping geometries are possible. iii.) since ions are not necessarily lost or ejected, the frequencies of these ion may be measured over very long times. Resolution measurements may be possible to R=1,000,000 at low pressures and for well engineered systems. That is, an ion trap built from parts machined to a high accuracy and precision. iv.) unlike in the FTMS experiments tried on a quadrupole ion trap, photons are measured not an induced electrical signal in the presence of the large main RF signal which would create noise. In addition, unlike FTMS, a large, expensive magnet is not required for the operation of the LIT at high resolution.

These and other teachings, variations, and advantages of the present invention will become apparent from the following detailed description of the invention.

BRIEF DESCRIPTION OF THE DRAWING

Embodiments of the present invention will now be described, by way of example only, with reference to the accompanying drawings for the purpose of illustrating the embodiments, and not for purposes of limiting the invention, wherein:

FIGS. 4 and 4A illustrate another embodiment of an apparatus according to the present invention using transparent electrodes. The four optically transparent electrodes (OTEs) can be made from quartz, glass, diamond or other transparent material and surface coated if needed with a conductive and transparent material like diamond. Agilent Corp. in California already makes gold coated quartz quadrupole electrodes. The Agilent electrode, however, is not optically transparent. In FIG. 4 the ions emit photons after excitation with a laser and these photons are focused through the quartz quadrupole rods due to the hyperbolic surface and a uniquely shaped back surface of the electrodes which optically corrects for the hyperbolic surface and focus the maximum amount of light from the line source to a point. It may be advantageous to use a quartz or glass window in the electrode that occupies only a portion of the electrode along the z-axis. (Note that the electrodes could also be made from highly reflective material so that the light is efficiently reflected and transmitted out of the inner trapping volume and into a PMT.) Optical filters maybe used as appropriate. For example, if one was doing DNA sequencing using different oligonucleotides tags each filter would be chosen so that the emission signal could pass through only one of the filters for each tag, respectively. Alternatively, four different lasers could be triggered at different frequencies (modulated) and the resultant signal deconvolved to create the appropriate spectra. Note that a transparent quartz cylinder may be used to transmit the photons out of the device while allowing for a higher pressure of helium inside the trap if needed. Care must be taken so that the quartz pieces do not charge and a semiconductor coating may be required to dissipate any charge. In some cases this cylinder could be made to be reflective to transmit the maximum amount of light out of the cell.

FIGS. 10A and 10B illustrate another embodiment of an apparatus according to the present invention where ions are resonated into larger orbits before excitation and photon detection. In this embodiment the ions can be selectively resonated in either the x- or y-axes separately. Ions may also be selectively resonated out of the center region of the trap for selective excitation by a laser or other light source in an inhomogeneous fashion or for excitation of the remaining trapped and helium damped ions. All electrode surfaces can be made to be reflective so that the quadrupole acts like a light pipe. The same LIT could be used for both the optical m/z measurement and for mass analysis by ejection as shown by the ion detector in FIG. 10A.

FIG. 37 illustrates a method of tagging a large protein complex with chromophore molecules so that the m/z can be determine by measuring the LIF and FFT. Light scattering can also be used directly followed by FFT analysis in a LIT. For example, heavy virus ions can not be seen in the ion trapping volume unless they emit detectable photons. The particle can not be seen be conventional ionizing detectors. Heavy ions can, however, be seen in the ion trapping volume if they are tagged with a fluorescent dye. The strongest photon emission signal will come from the precursor protein complex because of the higher number of tags. Protein complexes of lower m/z can also be seen in the ion trapping volume because they are tagged with a fluorescent dye. The photon emission signal from these smaller complexes will be reduced because they will have few tags molecules. The mass spectrum is shown at the bottom of FIG. 37.

FIGS. 45A, 45B, and 45C show a multi-pass light beam from an excitation source.

DETAILED DESCRIPTION OF THE INVENTION

Optical Trap

Figure 1:
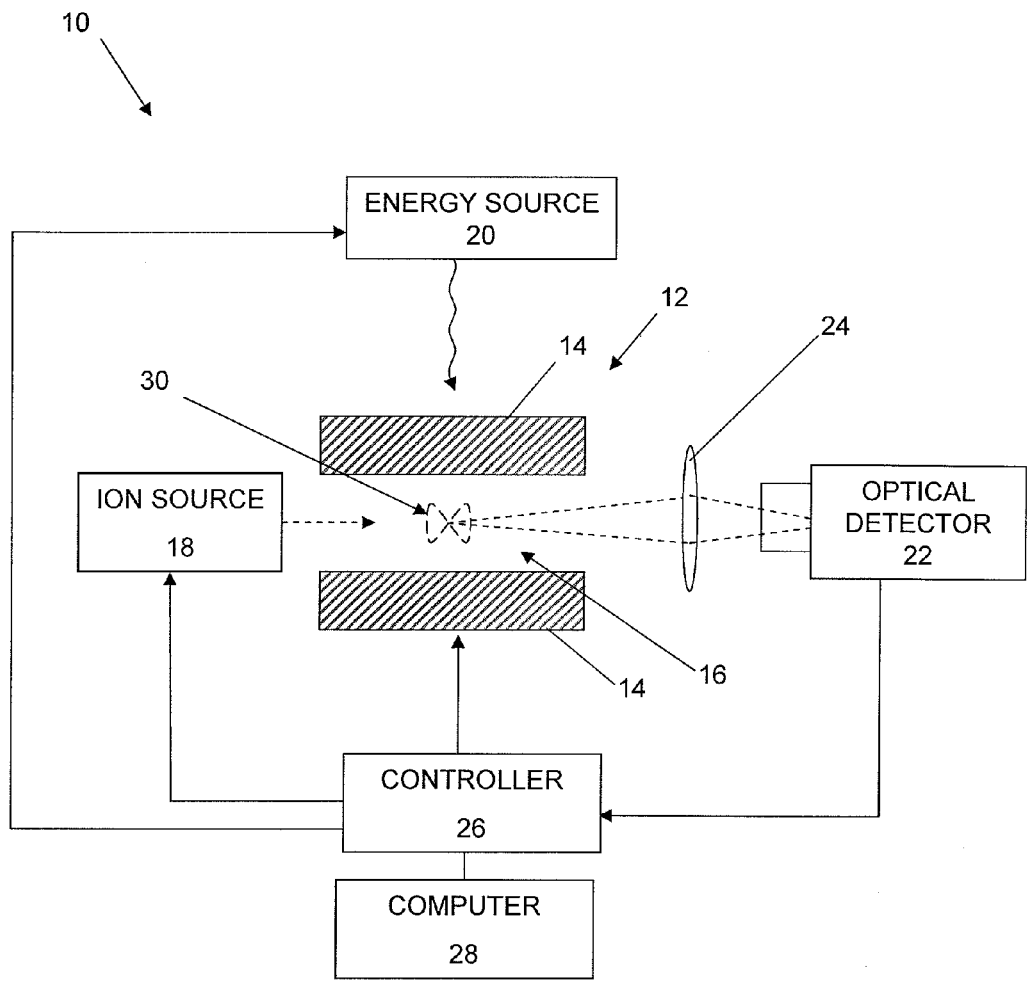
FIG. 1 illustrates one embodiment of an apparatus according to the present invention in which ions are trapped inside a linear ion trap (LIT). The LIT is controlled by a controller that applies waveforms onto the electrode so that ions will remain trapped inside the device for long periods of time. An ion source makes ions that are gated into the trap. An energy source such a laser is used to excite or shoot photons at the trapped ions. For laser induced fluorescence ions emit photons that can be captured at a photo multiplier tube or other photon measuring or imaging device. The frequency of an ion can be determined by the frequency in which the photons from that ion are received at the detector.

FIG. 1 illustrates one embodiment of an apparatus 10 according to the present invention. The apparatus 10 includes an ion trap 12, a plurality of electrodes 14 defining a trapping chamber 16, an ion source 18, an energy source 20, an optical detector 22, a controller 26, and a computer 28. Ions from the ion source 18 are injected into the ion trap 12, where they are trapped or contained. The energy source 20 excites the ions in the ion trap 12 and the optical detector 22 detects photons emitted from the ions in the trap 12. This embodiment also illustrates exemplary trajectories 30 of ions within the trapping chamber 16.

The ion trap 12 will generally be described as a linear ion trap ("LIT"), although the present invention may be used with other forms of ion traps and is not limited to the specific embodiments described herein. For example, the ion trap 12 may be other forms of ion traps such as, for example, a three-dimensional or two-dimensional quadrupole field ion trap, orbitrap or FTMS ion trap mass spectrometer. Other trapping mass analyzers may also be adapted to use with the present invention. The ion trap 12 traps ions with a "trapping field". The trapping field can be any field used to trap ions in an ion trap 12. The trapping field will generally be described in terms of a quadrupole field. However, the present invention is also applicable to ion traps 12 utilizing other fields, such as hexapole fields, octopole fields, multipole fields, and other fields that may be used in ion traps including, but not limited to orbitraps, ion cyclotron resonance devices, and other Fourier Transform devices.

The electrodes 14 may include one or more "transparent" electrodes 14. As will be described in more detail hereinbelow, a transparent electrode 14 includes at least a portion which is both optically transparent and electrically conductive. In other words, the transparent electrode 14 operates as a normal electrode but also allows light to pass through the transparent portion and be sensed by the optical detector 22. The transparent electrode 14 may be entirely transparent, or less than all of the transparent electrode 14, such as a "window" in the electrode 14, may be both transparent and electrically conductive.

The ion source 18 provides ions into the trapping chamber 16. An energy source 20 introduces energy into the trapping chamber 18.

The energy source 20 may be any source of energy applicable to use according to the present invention. For example, the energy source may be light, such as from light emitting diodes, lasers, or other sources of energy. The energy source 20 may be, for example, used to excite or otherwise provide energy to the trapped ions. For laser induced fluorescence, ions would emit photons that can be captured by a photo multiplier tube or other optical detector 22. The frequency of an ion can be determined by the frequency in which the photons from that ion are received at the detector 22. The energy source 20 may, for example, provide energy to the trapped ions through a transparent electrode 14. Alternatively, the energy source 20 may provide energy via openings between electrodes 14, or through non-conductive openings in electrodes 14.

The optical detector 22 detects light from the trapping chamber 16. The optical detector 22 may be, for example, a photo multiplier tube ("PMT"), a charge coupled device ("CCD"), or other optical or imaging devices. The optical detector 22 may detect an optical light, whether visible or invisible to the human eye. The optical detector 22 may be oriented so that the optically transparent portion of a transparent electrode 14 is oriented between the optical detector 22 and the trapping chamber 16. In this way, the optical detector 22 can detect light from the trapping chamber 16. A lens 24 may be included to focus the light from the trapping chamber 16 onto the optical detector 22.

One or more controllers 26 may be included to receive information from the optical detector 22 and other devices, and to control the electrodes 14, ion source 18, energy source 20, and other parts of the apparatus 10. A computer 28 can be used to send signals or to load control software into the controller 26.

The controller 26 applies electrical control signals to the electrodes 14. Under typical operation, the control signals from the controller 26 to the electrodes 14 are typically waveforms to cause the electrodes 14 to produce and maintain a quadrupole field in the trapping chamber 16 so that ions introduced into the trapping field 16 will remain trapped inside the trap 16 for long periods of time. The controller 26 can also change the control signals to the electrodes 14, such as to change or add additional control signals, in order to modify the quadrupole field or to cause other desired effects. This may be done, for example, so that trapped ions of specific masses are selectively moved within the trapping chamber 16. As will be described in more detail hereinbelow, such selective movement of ions may be used for selective imaging of ions, improved m/z analysis, and for other tests and analysis of the ions in the trapping chamber 16. The controller 26 and other aspects of the present invention are described in more detail hereinbelow.

The present invention may also use damping gas. Damping gas, such as helium, can be added to the ion trap 12 to improve the resolution of the analysis by damping the ions to the center of the ion trap 12. The helium removes the kinetic energy of the ions through collisions so that the trajectories inside the trapping device will not be influenced by the initial kinetic energy from the ion injection and trapping process. Once the ions are damped to the center of the trap 12 the ions can be excited with a photon source or with other energy sources 20. For example, the ions may be damped into an ion containment cylinder space ("ion trapping volume") of approximately 1 mm in radius and of lengths that could be 200 mm long. Other ion trapping volumes are also possible. Because the ions are damped, the best measurement of the secular frequency of each ion and the best resolution can be obtained. In addition to helium, laser cooling, or other methods could be used to reduce the energy of the ions. Resolution values might be achieved where R>1,000,000 for some m/z because long measurement times are possible. These signal measurement times can be orders of magnitude longer than what is used in the traditional LIT sold commercially. In some cases, the helium or other damping gas should be turned off and may be pumped away before the analysis. Ultra low pressures may be required to achieve ultra high resolution.

Figure 2:
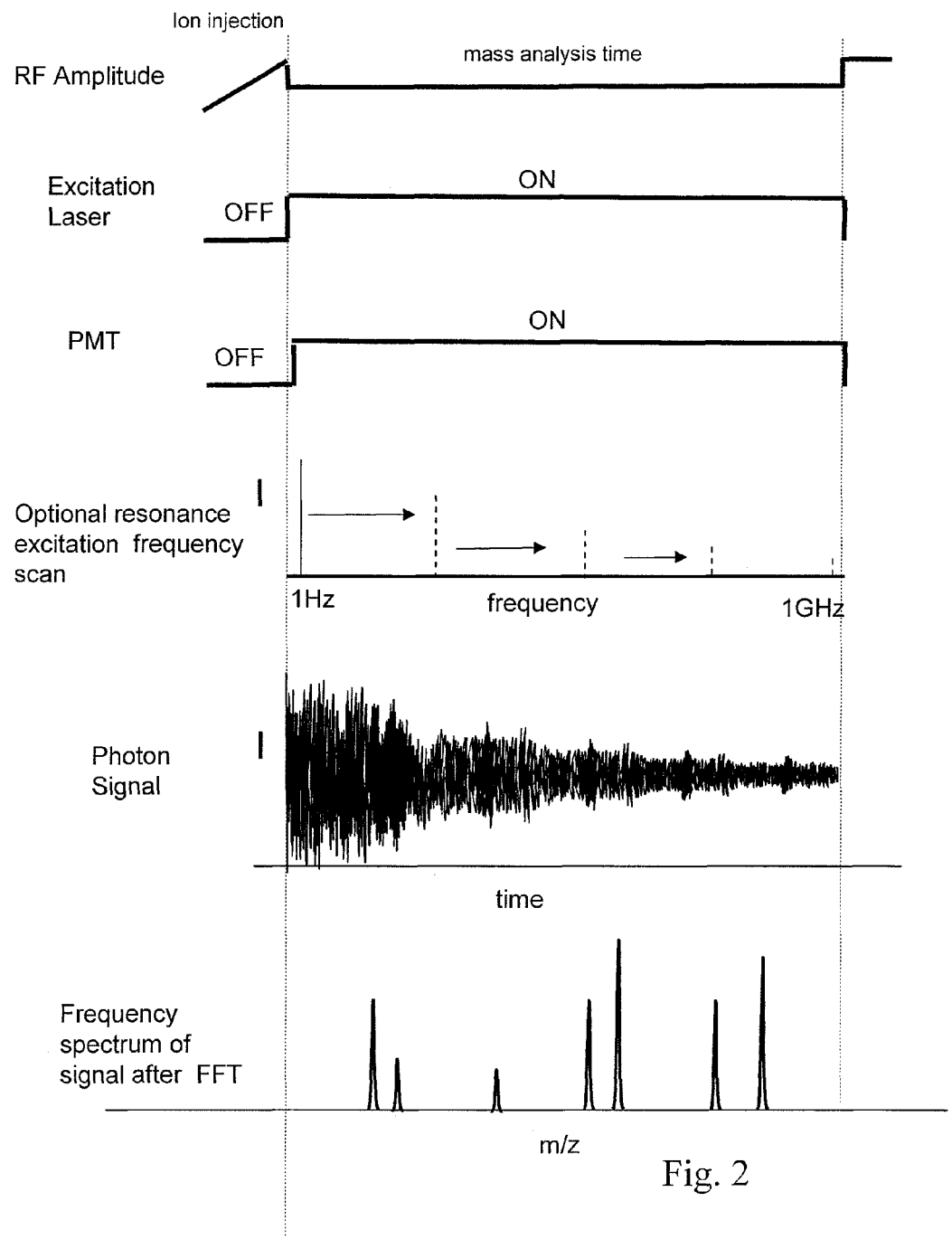
FIG. 2. Illustrates a timing diagram of one embodiment of the present invention where ions are trapped in the LIT for a period of time that allows for a LIF measurement. A laser is pulsed or is used as a continuous beam and a PMT measures the resultant emitted photon signal. An efficient photon collection means as describe herein, is used for optimum performance. Since each ion has a specific secular frequency inside the LIT due to its m/z, the signal can be converted into a mass spectrum by taking a fast Fourier transform. An optional and supplementary resonance excitation frequency scan (e.g., dipole signal applied to opposite rods or end cap electrodes) from high to low frequency or low to high frequency (e.g., 1 Hz to 10 GHz) with an adjustment in the signal amplitude with m/z could also be used to excited the ions into larger orbits. In addition, a waveform which is made up of all ion frequencies could be applied to the x-pair or y-pair of opposite electrodes so that all ions resonate at their secular frequencies in the x and y dimensions. In this way, the large excitation region is available for photon excitation. The Rf amplitude could also be increased to a higher voltage for a new scan. This would allow high m/z ions to be at a higher q or Beta value and thus frequency and this would allow one to achieve higher resolution. In other examples, the Rf amplitude may remain fixed or parked for the optical measurement. The laser beam can be directed along the z-axis or off-axis, but still parallel to the z-axis of the LIT (at different (x, y) coordinates) to achieve the best signal or for unique experiments. The ions do not have to be ejected for analysis and in the preferred embodiment long measurement times are preferred. These scans could be done with or without helium damping gas and pulsing the helium may be favorable in some cases. (Note that this FFT method could also be used with other mass analyzer types like the FTMS cell or the orbitrap.)

After ions are injected into the ion trap 12, the ions are damped and stored in an ion trapping volume or trapping chamber 16 along the axis of the trap 12. The length of the trap 12 could be as long as can be manufactured accurately. Quartz quadrupoles that are approximately 20 cm long are now possible. A laser (illustrated in FIG. 3) can be positioned to illuminate the ion cloud along the axis or slightly off-axis so that the maximum absorption of photons is possible. The laser beam will illuminate the ions inhomogeneously because of the Gaussian photon density of the beam. Whether on-axis or off-axis the photons will excite those ions that can absorb the light. The excitation frequency will depend on the secular frequency of the ions so that a direct measurement of the emitted photon signal can undergo Fourier transform analysis to generate the frequency or mass spectrum. A simple timing diagram is shown in FIG. 2 which shows the ion injection into a LIT 12, followed by LIF and FFT analysis. The PMT may be delayed slightly before turning on (not shown) to avoid the scattered light noise before the signal measurement. An FFT is used to take the photon signal and generate a frequency spectrum (mass spectrum).

FIG. 2 illustrates a timing diagram of one embodiment of the present invention where ions are trapped in the LIT 12 for a period of time that allows for a LIF measurement. A laser (illustrated in FIG. 3) is pulsed or is used as a continuous beam and an imaging device 22 measures the resultant emitted photon signal. An efficient photon collection device or method, as describe herein, may be used for optimum performance. Since each ion has a specific secular frequency inside the LIT 12 due to its m/z, the signal can be converted into a mass spectrum by taking a fast Fourier transform. An optional and supplementary resonance excitation frequency scan (e.g., dipole signal applied to opposite rods or end cap electrodes) from high to low frequency or low to high frequency (e.g., 1 Hz to 10 GHz) with an adjustment in the signal amplitude with m/z could also be used to excited the ions into larger orbits. The laser beam can be directed along the z-axis or off-axis, but still parallel to the z-axis of the LIT 12 (at different (x, y) coordinates) to achieve the best signal or for unique experiments. The ions do not have to be ejected for analysis and in the preferred embodiment long measurement times are preferred. In an additional scan mode, the main RF amplitude could be increased to several higher voltages in a step wise fashion (not shown). At each new high RF amplitude a FFT measurement of the signal would be taken so that higher m/z ions would have higher secular frequencies for improved resolution. For this scan you would lose the lower mass ions as they would fall off the edge of the stability diagram. These scans could be done with or without helium damping gas. This FFT signal processing method could also be used with other mass analyzer types, such as the FTMS cell or the orbitrap.

Referring back to FIG. 1, Helium or another gas or other damping methods could also be used in the trap to damp resonance excitation orbits so that the ions remain inside the tapping ion volume (or trapping chamber 16) for long measurement times. Helium or another gas or other damping methods could also be used in the ion trap 12 for ion mobility experiments. In the mobility applications a high pressure of helium or other gas would be used to damp the motion of the ions. Protein ions with different cross-sections due to different conformation differences would be separated by the motion through the gas since the migration of the two ion conformations would be different. The separation of the protein conformers could be detected by imaging or laser probing different regions of the trap 12.

In some embodiments of the present invention, the motion of the ions along the z-axis of a LIT 12 after ion injection could be used to determine the m/z of the ion based on the harmonic frequency of motion along the z-axis. An FFT of the photon emission or the induction signal over time can be used to generate the mass spectrum.

Certain aspects of the present invention will now be described in more detail. As mentioned above, the computer 28 can be used to send signals or to load control software into the controller 26. Although the computer 28 and the controller 26 are illustrated in FIG. 1 as being separate devices, the computer 28 and the controller 26 may also be integrated together. For example, the computer 28 and the controller 26 may be a single device. In general, the present invention will be described in terms of just a controller 26, although in other embodiments the present invention may include both a controller 26 and a computer 28.

The controller 26 can be used to provide control signals to various electronic modules for the ion source 18, the ion trap 12, and the detector 22. For example, a controller 26 can be used to signal an ion trap 12 controller such as an RF/DC waveform generator and amplifier to drive the amplitude and/or frequency of the RF and DC fields generated by power supplies to contain the ions within the trap 12 and to control the resonant frequencies and amplitude provided for resonance excitation or ejection. The present invention may, for example, utilize an ion trap controller (not shown) which may be part of the controller 26, or it may be a separate controller. The controller 26 may be a single device or several devices including, for example, an ion trap controller. The controller 26 can be programmed to drive other electronic devices that will provide signals to one or more parts of the apparatus. For example, in FIG. 1 the controller 26 provides control signals to the ion source 18 to control the injection of ions into the ion trap 12, the controller 26 provides control signals to the energy source 20 to control the excitation of ions in the ion trap 12, and the controller 26 provides control signal to the optical detector 22 and the ion trap 12 controller as mentioned.

In other embodiments, the controller 26 provides control signals to less than all of the other devices. The controller 26 may also receive signals from one or more other devices, and those signals may be used, for example, when the controller 26 provides control signals to other devices. More or less devices may also be used. For example, the controller 26 and the ion trap controller (not shown) were previously described as separate devices, although it is possible for a single controller to be used to perform the functions of the controller 26 and the ion trap controller. In other embodiments, additional controllers may be used. For example, a separate controller may be used with the optical detector 22, and another separate controller may be used with the energy source 20, and another separate controller may be used with the ion source 18.

The energy source 20 produces energy and directs that energy at the ions in the ion trap 12. The energy source 20 may be of any type such that when the energy is absorbed by the particles, neutral or ionized, it results in the emission of a photon or photons. For example, infrared light, near infrared light, visible light, ultraviolet light, other wavelengths of light, and other forms of energy, such as x-rays, may be used with the present invention. A laser or other sources of photon energy, such as a xenon lamp, laser diodes or filament lamp, or other sources of energy, such as an x-ray source, may be used. In some embodiments, the energy source 20 is selected so that certain ions absorb a specific wavelength of the energy and other ions do not. Ions that absorb this energy enter an excited state that may result in certain ions fluorescing or producing stimulated emissions which can be detected by a PMT or other optical detector 22 or which otherwise provides information about the ions within the ion trap. Various types of energy sources 20 may be used to make certain ions more visible to the optical detector 22 or to cause the ions to produce light or other energy indicative of characteristics or features of the ions which are of interest. In addition to LIF light scattering measurement can also be used to measure the ion secular frequencies.

In another embodiment, the electrodes 14, such as quadrupole electrodes or other electrodes, are made out of a material that will transmit the photons, x-rays, or other energy used with the present invention readily through the electrodes so that excitation and emission can be made through the electrodes if so desired. One such quadrupole could be made form quartz with a "see-through" transparent conductive coating on the inside, electrode surface. The see-through material may be, for example, diamond. The see-through material does not necessarily need to be transparent at visible wavelengths. For example, if the energy used to image or otherwise analyze the ions is not in the visible spectrum, then the see-through material may appear opaque to the human eye but still be see-through for the purposes of the present invention. Many variations of the present invention are possible. For example, the entire electrode 14 does not need to be "see-through." In some embodiments, a window could be made on the electrode 14. The window may be made, for example, of quartz with a diamond coating, or it may be made of other materials. Additionally, either along the asymptotes or through slots, slits, or other openings in the electrodes or through conductive screens, both excitation and emission processes can occur so that a photon signal can be collected and or imaged. A wire grid could also be used to form the electrodes and allow for efficient excitation or collection of photons.

In another embodiment, the shape of the transparent electrode 14 may be such that it assists in the excitation of the ions and/or in the collection of photons emitted from the ions. The electrode 14 itself can assist in the photon measurement analysis or imaging by directing photons to a detector 22. For example, one or more optically transparent electrodes 14 (quadrupole rods) may be shaped to bend or focus light or other energy passing through the electrode 14. In this way, the electrode 14 may act as a lens to efficiently capture and focus energy. As discussed above, the electrode 14 acting as a lens may, but is not required to, be transparent to visible light. In some embodiments, the electrode may be opaque to visible light but transparent to other forms of energy used in the device. In addition to photon detection, the electrodes can be shaped on the back side to focus excitation photons onto the trapped ions.

In another embodiment, the four optically transparent electrodes (OTEs) 14 of a LIT 12 can be made from quartz and surface coated with a conductive and transparent material like diamond. Agilent Corp. already makes gold coated quartz quadrupole electrodes. The ions inside the LIT emit photons which are focused through the quartz quadrupole rods due to the hyperbolic surface and a uniquely shaped back surface of the electrodes which optically corrects for the hyperbolic surface and focus the light from a line source to a point where optical detector 22 is located.

In another embodiment a lens 24 is positioned so that the photons that are emitted from the LIT 12 (such as between the rods 14, through a slot or aperture, or directly through a transparent electrode 14 or transparent electrode window) can be captured and focus using light pipes, fiber optics or lenses such as a Fresnel lens.

In other embodiments, select ions are imparted with greater energy as in resonance excitation by an excitation frequency. For example, in a 3D quadrupole field ion trap 12 the resonance frequency of an ion can be calculated using $f_h = (hf_{RF} \pm \beta_z f_{RF}/2)$ where $h = \{0, \pm 1, \pm 2, \pm 3 \ldots\}$. By knowing the $q_z$ of an ion, one can calculate the $\beta_z$ value and thus the resonant frequencies of an ion following equation. At low $\beta_z$, the frequency components ($|h| > 0$) have a negligible effect on ion motion and unless large voltages are applied to the end caps these higher order frequencies are usually insignificant and thus, not utilized. In general, the fundamental resonant frequency of an ion is defined as the frequency where $h=0$ (i.e., $fz_{-res} = f_0 = \beta_z f_{RF}/2$).

This resonance excitation causes these ions to travel to parts of the ion trap where other, non-excited ions do not travel. The resonantly excited ions may be imaged or analyzed, for example, by focusing the laser on one or more parts of the ion trap where they are traveling, but where other ions are not. For example, a laser beam may be focused on one or more locations away from the center of the ion trap in order to optically excite ions that are undergoing resonant excitation in that region. An optical detector 22 can be used to capture these stimulated emissions from the excited ions and a FFT could be used to convert the signal to a frequency and thus mass spectrum or the signal could be correlated to the RF level and thus m/z. For example, in a LIT mass spectrometer ions can be resonantly ejected out of two opposing rods. Instead of resonantly exciting the ions out of the trap, the ions can be kept below the resonance excitation threshold for ejection thus limiting the ion trajectory. Instead of ejection, the ions fall out of resonance as the main RF amplitude is scanned past the resonance point and are damped with helium back to the center of the LIT 12. A photon signal could be measured and a mass spectrum created. Eventually, with increasing RF amplitude applied to the rods these ions would fall of the edge of the stability diagram and be lost. To avoid the loss of ions, a resonant excitation frequency can be scanned across all ion frequencies from 0 to 1 G Hz (or in reverse) to resonantly excite one m/z after another sequentially. The resonance excitation amplitude should be adjusted during the scan so the ions of all m/z remain in the trap for repetitive scanning. Additional electrodes between the rods of a LIT could be used to apply the resonance ejection waveform. It should be noted that a direct FFT analysis without resonantly excitation can also be done.

In another embodiment a DC potential is applied to two opposing electrodes so as to displace the ions toward or away from the respective electrodes 14 depending on the charge state of the ion and polarity of the electrode 14. This method can be used, for example, to cancel out the effects of gravity for macromolecules.

In another embodiment the ions can be resonantly excited in both the x and y dimensions by applying waveforms that contains all frequencies except for a notched frequency to opposite pairs of rods 14. The notched frequency is at the ion secular frequency of interest. The notch in the frequency spectrum will keep the ion at this secular frequency from resonating away from the center of the trap 12 so that it can me analyzed separately from the ions that have been resonantly excited.

In other embodiments the photon energy source 20 is used primarily to impart energy for stimulated emissions and similar effects, and the ion trap 12 is controlled so as to provide for certain ions to take trajectories within the ion trap 12 and away from other ions. This may be done, as described herein below, by adjusting or adding control signals to the ion trap 12 to resonate certain ions more than others, thereby causing the resonated ions to follow trajectories beyond those of the other ions. One method of resonating ions into larger trajectory can be accomplished by applying a dipole resonance excitation to two of the opposite poles in the ion trap 12. These two poles can be the end caps in the 3D quadrupole field ion trap 12 while they can be two opposing pairs of rods 14 in the 2D quadrupole field ion trap. Small AC resonant excitation voltages at the proper ion frequency which is dependant on the ions m/z will cause the ions to enter into resonance and the distance that the ion traverses will be increased. Ions of the incorrect m/z will not undergo the resonance process and remain near the center of the trap 12. Many variations and combinations are also possible such as resonating ions in both the x and y dimension with two dipole signals applied to opposite pairs of rods in a LIT 12.

The Doppler effects should be considered when making these the light measurements for m/z analysis. It may be advantageous to make measurements when the ions are moving at their lowest velocity away or towards the light detector. This would typically be at the apex of the ion trajectory where the ion will change directions. In some cases this would be near the hyperbolic surface of the electrode. As a result the laser should be focused to the apex of the ion trajectory to measure the smallest shift in the frequency in which the light is measured. In this same regard, it would be best not to measure the ion emission as the ion is quickly coming toward or away from the detector. Instead try to measure perpendicular to this ion motion so the velocity to and fro is minimized. A calibration could be used to minimize this frequency error.

Since according to one method of this invention, the ion are not ejected, but instead held and measured for long time periods, higher resolution and sensitivity should result. Long measurement times can be uses to measure the secular frequency of each ion very precisely by FFT of the LIF signal or scattered light. The field near the electrode 14 is not distorted because no holes or slots are required for the analysis. The lack of these modifications to the electrodes 14 should result in a purer quadrupole field without non-linear resonances that could add additional undesirable frequencies to the spectrum and the purer field should allow for improved resolution. Since there is no loss of ions due to ejection and a set of ions is not required for analysis unless desired, improved sensitivity and duty cycle should result.

For mass spectrometry/mass spectrometry (MS/MS) scans the precursor ion of interest can be isolated, collisional activated and then the fragments determined by LIF as explained herein, but in this invention the precursor ion could also be resonantly excited without isolation if the ensemble of ion intensity is first measured non-destructively to a high degree of accuracy with high resolution. Since a baseline will be established during this first measurement, the MS/MS measurement will reveal the new product ions once the baseline spectrum is subtracted from it. The MS/MS scan can be repeated on a new ion without isolation or ejection of other ions.

In another embodiment the ions can be optically analyzed by LIF and then injected into a second analyzer. The normal scan operation as done with the currently commercial instrumentation of Sciex Corp. in Toronto, Canada or Thermo-Electron Corp. in San Jose, Calif. can be used to mass analyze all ions, even those that do not fluoresce. Additionally, a second mass analyzer like FTMS could be used. In the second mass analyzer a normal mass analysis scan can take place. In the LIT case, this would mean ejection out of the analyzer to an ionizing detector.

One example of such an embodiment of the present invention is a gas phase DNA sequencer that uses multiple lasers and fluorescent tag molecules for each of the bases: A, T, G, and C. The DNA mixture is ionized and trapped in a LIT 12. Each laser excites a different fluorescent molecule and these molecules emit a photon at a different wavelength. Each laser could be modulated at different frequencies and a lock-in amplifier could be used to obtain the respective signal for each base. Alternatively four different photon filters can be used to selective transmit the emitted photon to a specific PMT. The signals collected at each PMT could then go under FFT analysis to create four mass spectra, one for each base. The spectra can be combined and the sequence read off for each m/z.

Another specific example of the application of the present invention is the molecular weight determination and fragmentation of a 13 mega Dalton capsid from a virus particle. These particles are made up of many large proteins that cannot typically be mass analyzed by conventional detectors. By tagging the large complex with many, perhaps hundreds, of dye molecules a strong photon signal should result once excited by the proper excitation source. Since we are measuring photons emitted from theses mega Dalton ions we can detect them. Conventional prior art detectors like a microchannel plate (MCP) detector, which is of the ionizing type, would not generate a significant signal. Dissociating this large particle into its smaller protein subunits could be further imaged and mass analyzed using FFT. The molecular weight limit to this optical trap technology should be greater than the Giga Dalton range of singly charge ions, but lower m/z ions would work as well.

Many other variations are also possible with the present invention. For example, an additional DC voltage may be used to displace the ions toward or away from the respective electrodes depending on the charge and polarity and can be used to cancel out gravity for macromolecules. One could also resonate all ions at once to outer orbits and then measure the frequency that photons that are received from all ions in one region of the trap and then take a Fourier transform of this signal to determine the m/z. In other embodiments of the present invention utilizing Fourier Transform, one may measure at a high frequency $\Omega$ so that the secular frequencies of the ions are large.

An advantage of the LIT 12 according to the present invention is that the frequency of the secular motion $\omega_x$ and $\omega_y$ can be the same so that harmonics of the two frequencies will be absent. There can also be a frequency due to the oscillation of the particle along the z-axis which could be filtered out or used for ion mobility or other experiments or damped with helium. Ions can be resonated between the two trapping end plates and the position and/or frequency measured to gain information about this motion as well.

The present invention may also space the trap electrodes 14 so that the non-linear resonances are reduced (e.g., octopole, hexapole) or added for improved performance. The present invention may have no slots in the LIT 12 to form a more perfect quadrupole field with minimum interference of hexapole and octopole fields. Those and other variations and modifications are possible with the present invention. Several other variations and embodiments of the present invention will now be described.

Figure 3:
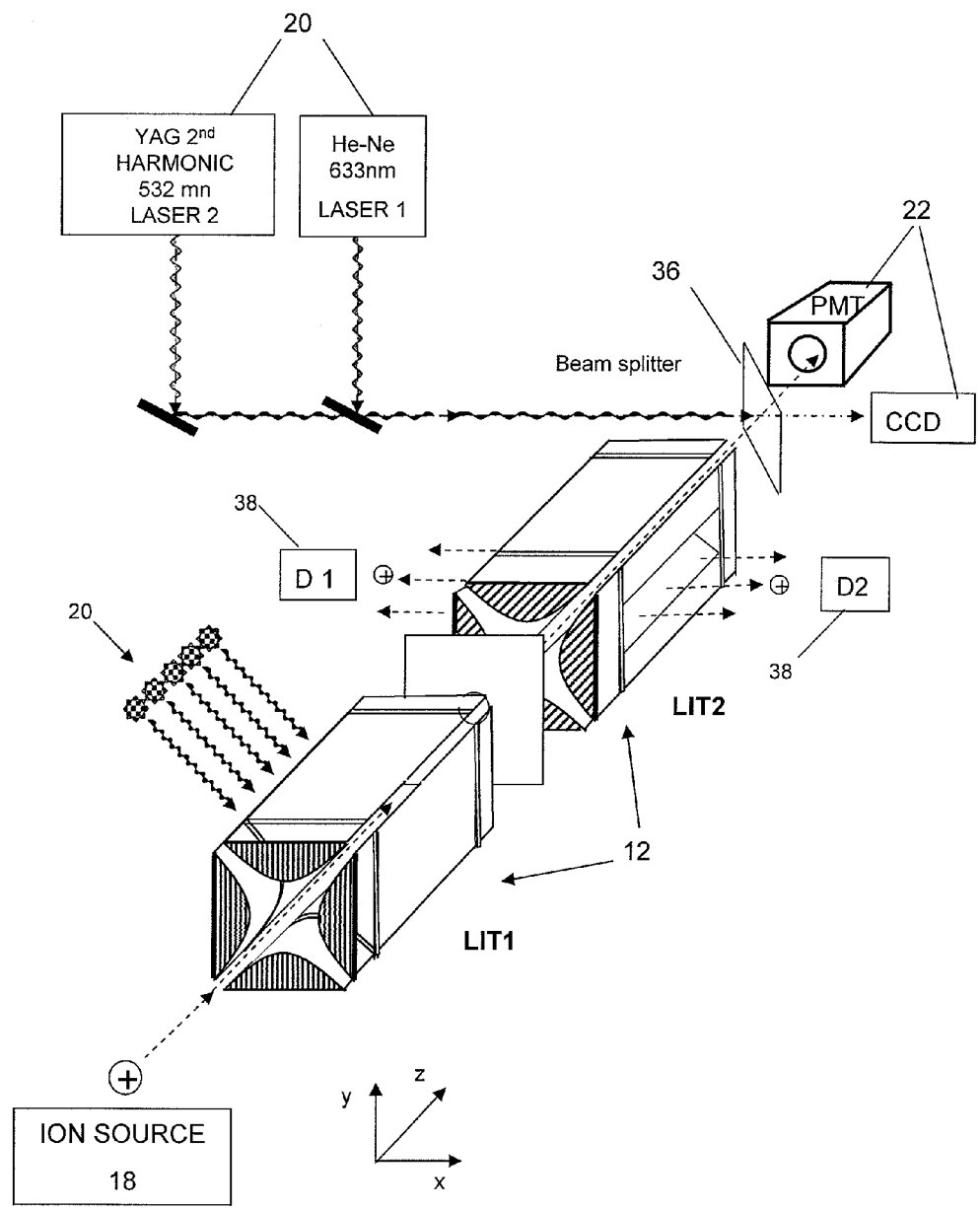
FIG. 3 illustrates another embodiment of an apparatus according to the present invention where two LITs are coupled together. LIT1 is an optical ion trap mass analyzer which uses non destructive mass analysis means and long measurement times while mass analyzer 2 is an ion ejection LIT or a mass analyzer of another type. LIT1 does not have slots cut into the hyperbolic electrodes and is used as the optical mass analyzer. Ions with fluorescent chromophores are detected by measuring the modulated photon emission signal using a PMT or imaging device. Ions in LIT1 can be fragmented for $MS^n$ analysis using collisional activated dissociation (CAD) or photon induced dissociation (PID) or electron transfer dissociation (ETD) or electron capture dissociation (ECD) or other means and further analyzed and/or transferred from LIT1 to another mass analyzer along the z-axis. Note that two lasers are shown to excite the chromophores at different wavelengths. Alternatively another excitation source could be used like light emitting diodes as shown by LIT1. In addition, both the optical and ion ejection method of m/z analysis could occur in the same mass analyzer and this may be advantageous in some cases.

FIG. 3 illustrates another embodiment of an apparatus according to the present invention where two ion traps 12 (LIT1 and LIT2) are coupled together. LIT1 is an optical ion trap mass analyzer which uses non destructive mass analysis means and long measurement times while mass analyzer LIT2 is an ion ejection LIT or a mass analyzer of another type. LIT1 does not have slots cut into the hyperbolic electrodes 14 and is used as the optical mass analyzer. Ions with fluorescent chromophores are detected by measuring the modulated photon emission signal using a optical detector 22. Ions in LIT1 can be fragmented for MS$^n$ analysis using CAD or PID or ETD or other means and further analyzed and/or transferred from LIT1 to another mass analyzer along the z-axis. Note that two lasers 20 are shown to excite the chromophores at different wavelengths via a beam splitter 36. Alternatively another excitation source could be used like light emitting diodes as shown by LIT1, and more or fewer sources than two may be used. Ion detectors 38 (D1 and D2) are used to detect ions that are ejected from LIT2 through an opening 32 in the LIT. Openings may be formed between electrodes 14 or openings 32 may be in an electrode 14. According to another embodiment of the present invention, one or both ion detectors 38 may be replaced with optical detectors 22 so that optical measurements can be made. In other embodiments, an opening (not shown) may be formed within the top electrode of LIT2 and an optical detector 22 (not shown) may be located above LIT2 so that both the ion detectors D1 and D2 and the additional optical detector 22 (not shown) can be used to make measurements.

A charge coupled device (CCD) is shown in combination with an PMT near the beamsplitter 36. In this embodiment the CCD is used for optical imaging and the PMT is used for Fourier Transform measurement. Other variations and combinations of optical detectors 22 may also be used.

Figure 4:
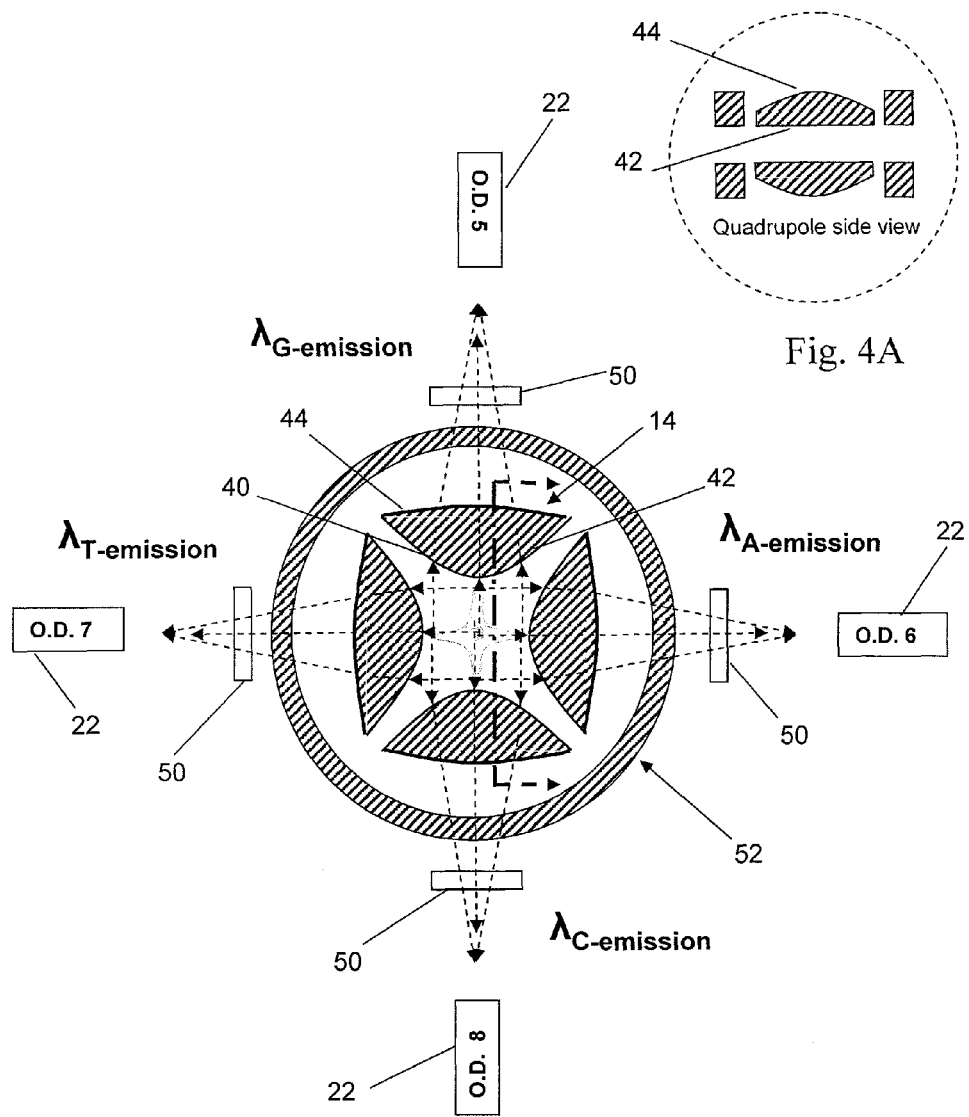

FIG. 4 illustrates another embodiment of an apparatus according to the present invention including optical electrodes for photon collection and focusing. This embodiment uses four transparent electrodes 14. The four optically transparent and electrically conductive electrodes 14 can be made from quartz or diamond or glass or KBr or NaBr or transparent plastic and surface coated with an electrically conductive and optically transparent material 40 such as diamond. As described herein, the transparent electrodes 14 may be entirely transparent or they may include only a portion that is both optically transparent and electrically conductive. For example, Agilent Corp. makes gold coated quartz quadrupole electrodes. The electrically conductive, optically transparent coating 40 may be located on one or more surfaces of each transparent electrode 14. For example, the coating 40 may be on all or a portion of the inner surface 42 of the electrode 14, on all or a portion of the outer surface 44 of the electrode 14, or on both surfaces 42, 44. Furthermore, if the electrode 14 has surfaces other than inner 42 and outer 44 surfaces (such as if an electrode 14 is constructed with side surfaces), those other surfaces may contain the coating 40. In other embodiments, the coating 40 may be integrated into the electrode 14, such as being located between two pieces that collectively form the electrode 14. The coating 40 may be a planar material applied like a sheet or strips to the electrode 14. Other variations are also possible. For example, the coating 40 may be a grid or mesh that provides a conductive coating 40 that is also optically transparent. For example, a gold mesh may be used to provide an electrically conductive, and optically transparent coating even though gold is not optically transparent. In another embodiment, the electrode itself could be a grid or mesh, thereby eliminating the need for an optically transparent material to which the grid is attached. The coating 40 may also be an etched grip or other etched coating.

In some embodiments the transparent electrodes 14 may be entirely transparent, such as being entirely made of optically transparent quartz or glass or diamond. In other embodiments, only portions of the electrodes 14 are both transparent and electrically conductive. For example, a portion of the electrode 14 may form a "window" or other optically transparent portion in an otherwise optically opaque electrode 14. In such cases, the electrically conductive coating 40 may be located only on the optically transparent portion of the electrode 14.

Although the illustrated embodiment shows that all four electrodes 14 are optically transparent, the present invention may also be used in apparatuses 10 in which less than all of the electrodes 14 are transparent. Furthermore, the present invention is illustrated as having four electrodes 14, although the present invention is not limited to four electrodes 14 and the present invention may be used with different numbers of electrodes 14.

The transparent electrodes 14 may be specially shaped to facilitate better operation of the device. For example, the transparent electrodes 14 may include an hyperbolic inner surface 42, and an outer surface 44 (or back surface) that compensates for the hyperbolic inner surface 42 and allows the emitted light to be focused on and collected by the optical detector 22. The outer surface 44 may be, for example, shaped to form a Fresnel or convex lens. The inner surface 42 of the transparent electrodes 14 face the trapping chamber 16.

The ions emit photons which are focused through the electrodes 14 (e.g., quartz quadrupole rods) due to the hyperbolic inner surface 42 and a uniquely shaped outer (back) surface 44 of the electrodes 14 which optically corrects for the hyperbolic surface 42 and focus the maximum amount of light from the line source to a point, such as the optical detector 22. In other embodiments, the electrodes 14 could also be made from highly reflective material so that the light is efficiently reflected and transmitted out of the inner trapping volume and into a optical detector 22.

Optical filters 50 maybe used as appropriate. For example, if one was doing DNA sequencing using different oligonucleotides tags each filter would be chosen so that the emission signal could pass through only one of the filters 50 for each tag, respectively. Alternatively, four different lasers 20 (not shown) could be triggered at different frequencies (modulated) and the resultant signal deconvolved to create the appropriate spectra. Note that a transparent quartz cylinder 52 may be used to transmit the photons out of the device 10 while allowing for a higher pressure of helium inside the trap 12 if needed. Care must be taken so that the quartz pieces do not charge and a semiconductor coating may be required to dissipate any charge. In some cases this cylinder 52 could be made to be reflective to transmit the maximum amount of light out of the cell.

FIG. 4A illustrates a cross-sectional view along the dashed line in FIG. 4. In FIG. 4A, the shape of the electrodes can be more clearly seen.

Figures 5A, 5B, 5C:
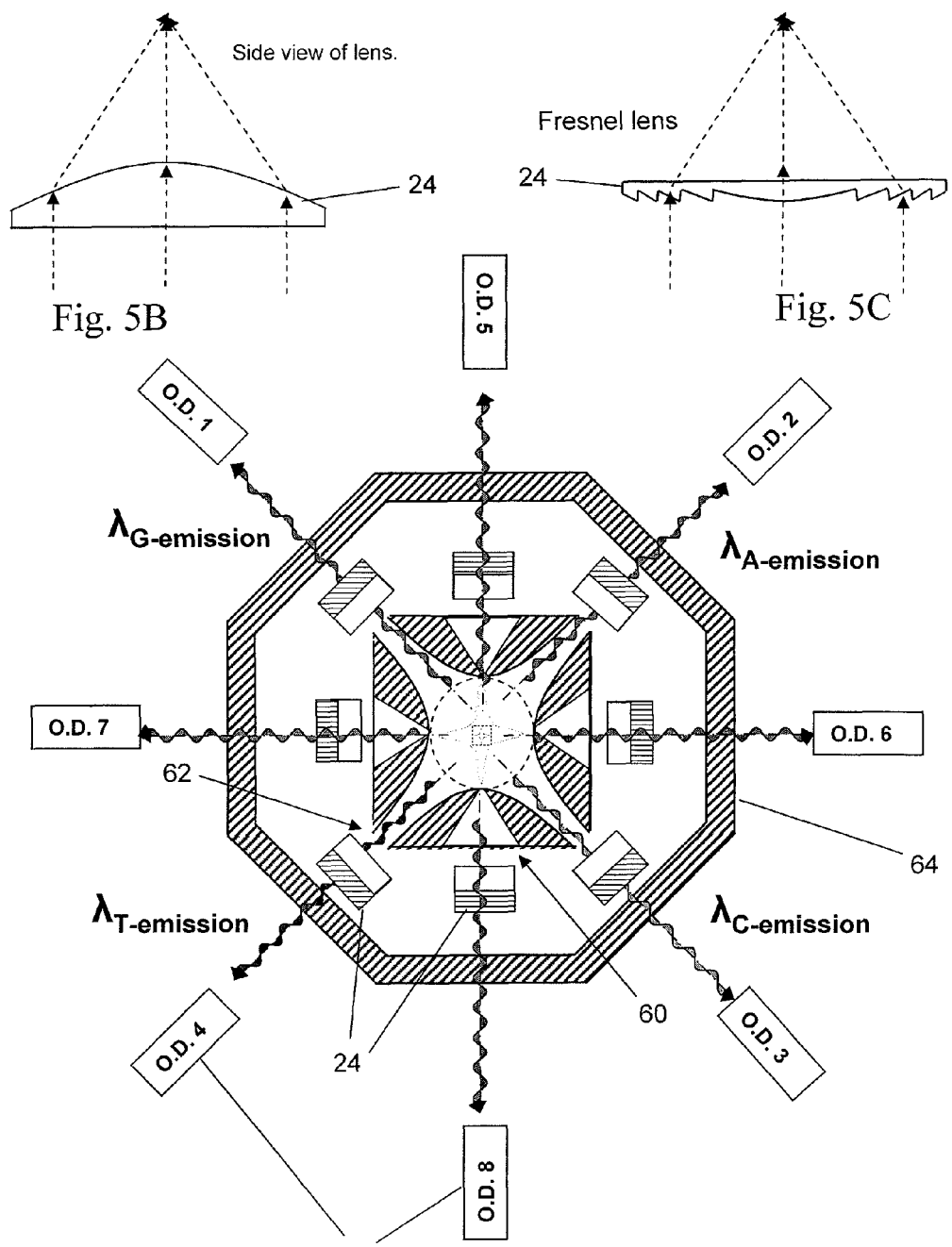
FIGS. 5A, 5B, and 5C illustrate another embodiment of an apparatus according to the present invention where photons are detected through slots in the electrodes or along the asymptotes. Traditional convex and Fresnel lenses are used to collect and focus the photons. The quadrupole rods may be sleeved into a transparent quartz cell of cylindrical of multi-sided geometry to let the photons escape while allowing for helium to be trapped inside the cell at 1 mTorr. The lens elements may be placed outside this transparent chamber inside the chamber or manufactured as part of the chamber wall. Shown here the elements are inside the chamber.

FIGS. 5A, 5B, and 5C illustrate another embodiment of an apparatus 10 according to the present invention where photons are detected through slots 60 in the electrodes 14 or along the asymptotes 62. The slots 60 in the electrodes 14 may be openings in the electrodes 14, or the slots 60 may be both optically transparent and electrically conductive portions of the electrodes 14 as described herein. FIG. 5A illustrates one embodiment of the apparatus 10, and FIGS. 5B and 5C illustrate embodiments of lens 24. Tradition convex and Fresnel lenses 24 are used to collect and focus the photons. The quadrupole rods 14 may be sleeved into a transparent quartz cell 64 of cylindrical of multisided geometry to let the photons escape while allowing for helium to be trapped inside the cell 64 at 1 mTorr. The lens 24 elements may be placed outside this transparent chamber 64 inside the chamber 64 or manufactured as part of the chamber 64 wall. Shown here the elements 24 are inside the chamber 64.

Figure 6:
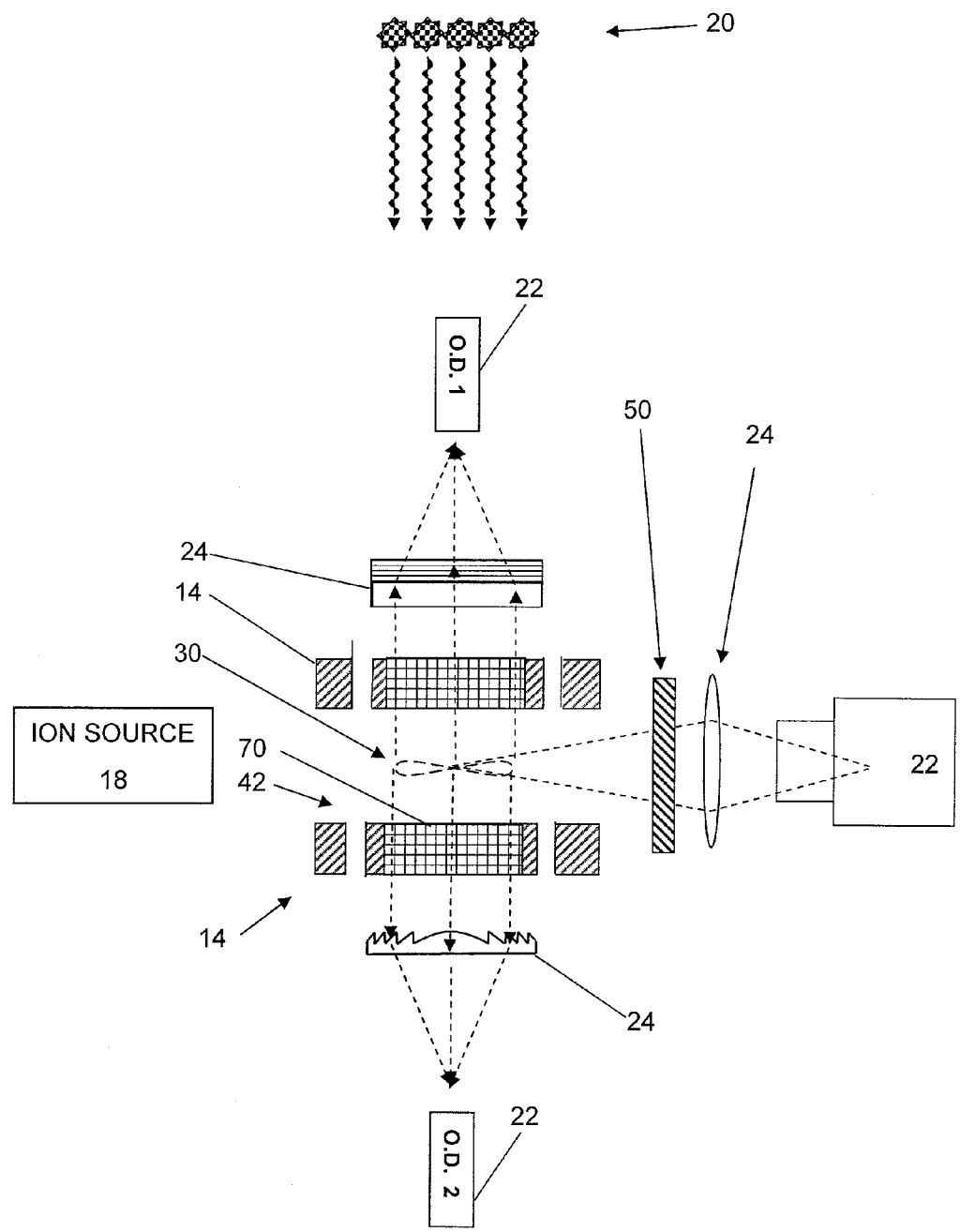
FIG. 6 illustrates another embodiment of an apparatus according to the present invention using two different kinds of lenses as shown in FIG. 5. In addition, light may be focused to a PMT along the ion axis. The inner surfaces of the electrodes if not transparent could be made to be reflective. The electrodes could also be made out of a grid or wire mesh. One such design would be to use a quartz quadrupole similar to what is taught in U.S. Pat. No. 4,885,500, but rather than using solid gold "conductive strips" one would use one or more conductive grids along the apex of hyperbola, as shown in FIG. 5, so that a high percentage of light is transmitted thru the quadrupoles, while still allowing for the electrode surfaces to remain electrical conductive and hyperbolic in shape.

FIG. 6 illustrates another embodiment of an apparatus 10 according to the present invention using two different kinds of lenses 24 as shown in FIG. 5. In addition, light may be focused to an optical detector 22 along the ion axis. The inner surfaces 42 of the electrodes 14 if not transparent could be made to be reflective. The electrodes 14, or a portion of the electrodes 14, could also be made out of a grid or wire mesh to form an optically transparent and electrically conductive portion 70 of the transparent electrode 14.

Figure 7:
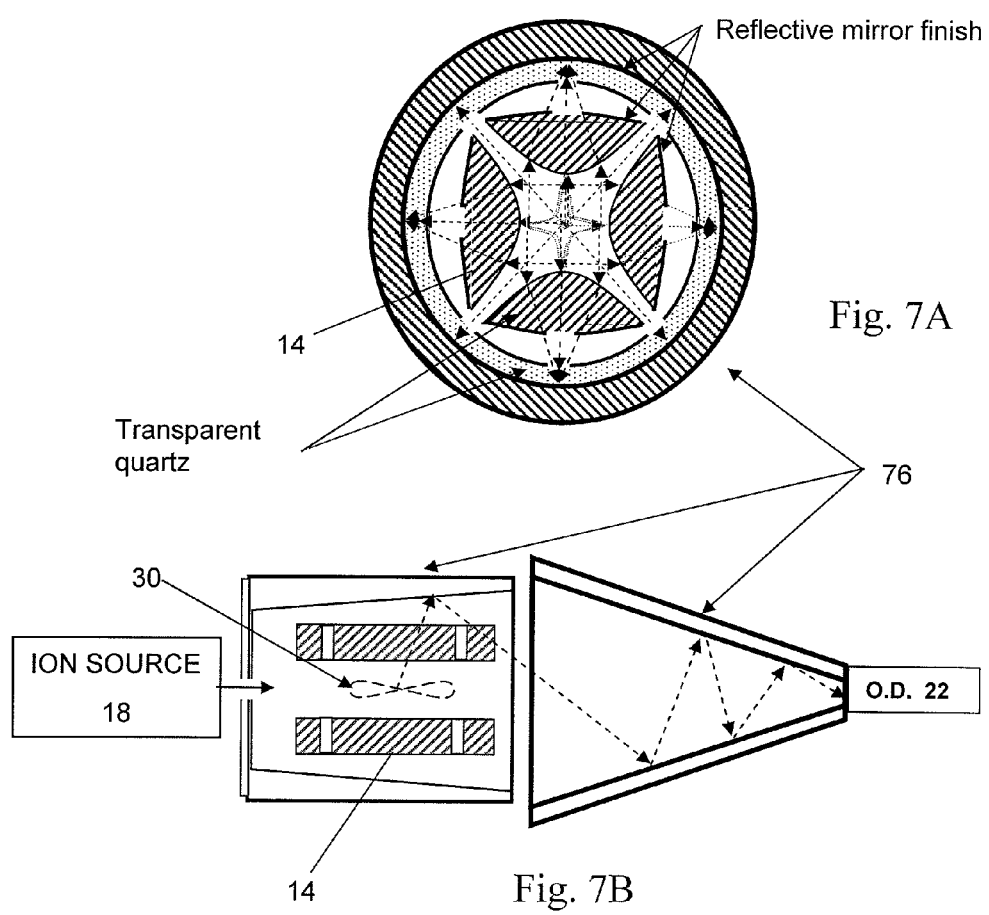
FIGS. 7A and 7B illustrate another embodiment of an apparatus according to the present invention where photons are detected after transmitting through the quadrupoles and entering a uniquely shaped cylinder that can both reflect and transmit photons. Part of the quadrupoles could also be reflective so that you transmit the maximum number of photons to the detector. You could uniquely modulate four different lasers each at different wavelengths and use one PMT to measure the respective photon signals.

FIGS. 7A and 7B illustrate another embodiment of an apparatus 10 according to the present invention utilizing optical electrodes for photon collection and focusing. In this embodiment, photons are detected after being transmitting through the transparent electrodes or quadrupoles 14 and entering a uniquely shaped cylinder, or light pipe 76, that can both reflect and transmit photons. The term "light pipe" 76, as used herein, means a device or devices for reflecting, directing, or channeling light to a desired location, such as an optical detector 22. The light pipe 76 may be reflective surfaces, optical fibers, other devices, and combinations thereof. Part of the quadrupoles 14 could also be reflective so that you transmit the maximum number of photons to the detector 22, which is a PMT in this embodiment, although other optical detectors 22 may also be used. One could uniquely modulate four different lasers (not shown) each at different wavelengths and use one optical detector 22 to measure the respective photon signals.

Figure 8:
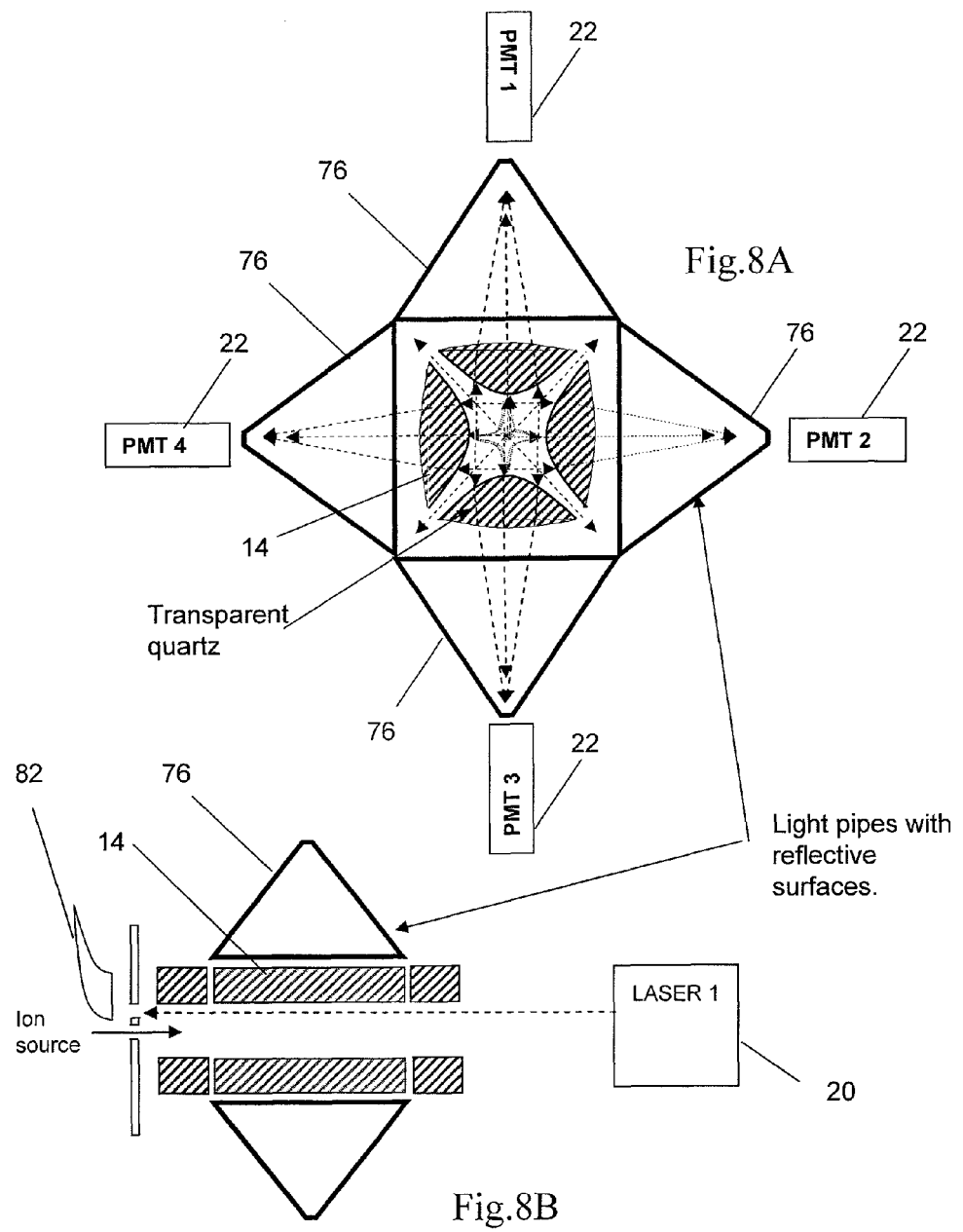
FIGS. 8A and 8B illustrate an embodiment of the present invention similar to that in FIG. 7, except with light pipes made out of a material that can capture and transmit photons back to a detector. This embodiment can uniquely modulate four different lasers each at different wavelengths and use one PMT to measure the respective photon signals.

FIGS. 8A and 8B illustrate an embodiment of the present invention similar to that in FIGS. 7A and 7B, except with light pipes 76 made out of a material that can capture and transmit photons back to a detector 22. The embodiment illustrated in FIG. 8A can uniquely modulate four different lasers each at different wavelengths and use one PMT 22 to measure the respective photon signals. As the electrodes 14 in FIG. 8A are transparent, either entirely or in part, so as to allow light to pass through the electrodes 14 and reach the optical detectors 22. Also noted in FIG. 8B is a lens element between the ion source and the LIT. This lens has an additional hole cut into it so that the laser light that is not absorbed by the ions can pass out of the LIT to prevent backscattering. Once on the other side of the aperture the light will go inside a horn 82 to prevent light backscattering.

Figure 9:
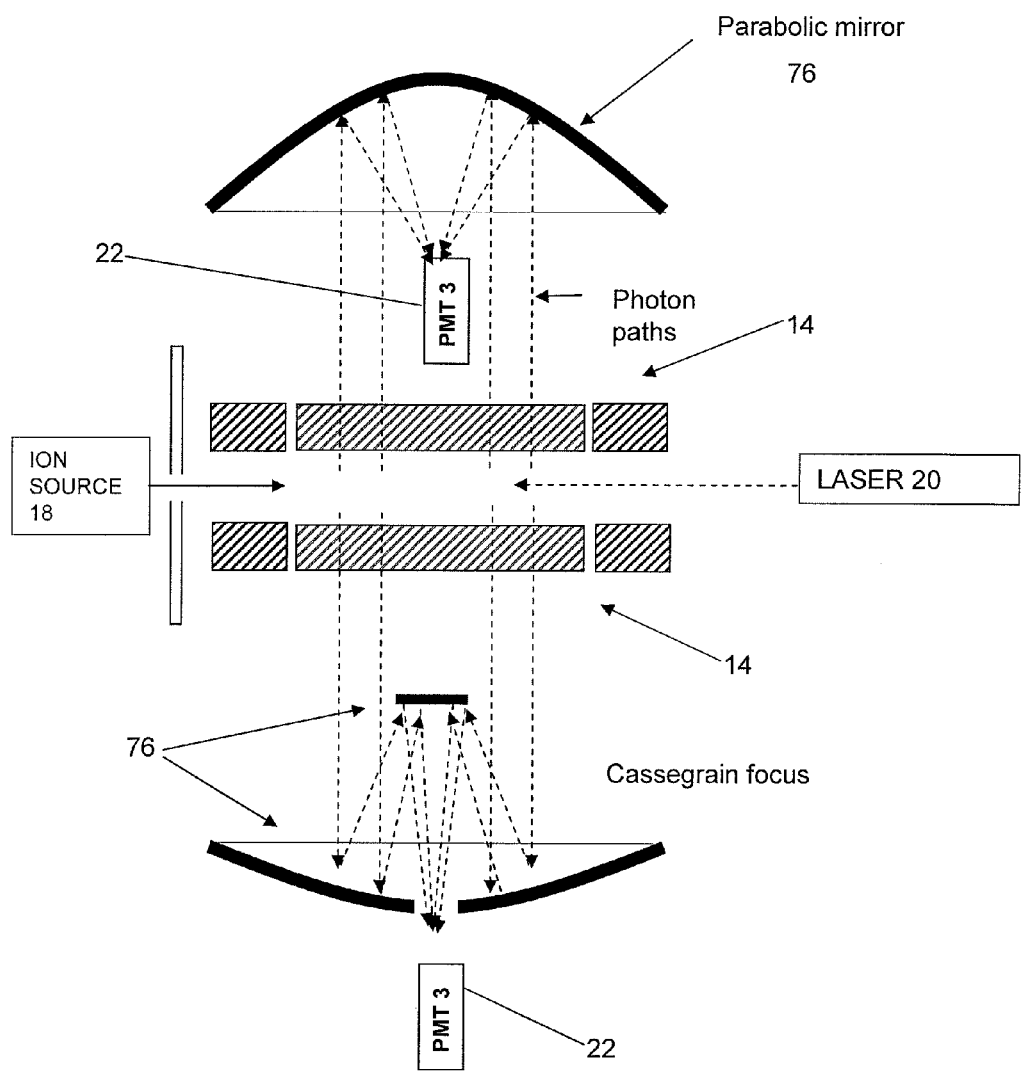
FIG. 9 illustrates another embodiment of an apparatus according to the present invention where photons are detected after reflecting from a curved mirror surface similar to that used in reflector telescopes. In this embodiment a modified reflective type telescope could be used to collect the light.

FIG. 9 illustrates another embodiment of an apparatus 10 according to the present invention where photons are detected after passing through transparent electrodes 14 and reflecting from a curved mirror surface 76 similar to that used in reflector telescopes. In this embodiment a modified reflective type telescope could be used to collect the light. As described herein, the transparent electrodes 14 may be entirely transparent or they may include a portion that is both transparent and electrically conductive.

FIGS. 10A and 10B illustrate another embodiment of an apparatus 10 according to the present invention where one or more controllers 26 control the electrodes 14 so that ions are resonated into larger orbits before excitation and photon detection. In this embodiment the ions can be selectively resonated in either the x- or y-axes separately. Ions may also be selectively resonated out of the center region of the trap 12 for selective excitation of the remaining trapped and helium damped ions. One or more optical detectors 22 may be used directly or via light pipes 76. The same LIT could be used for both the optical m/z measurement and for mass analysis by ion ejection as shown by the ion detector 38 in FIG. 10A. These embodiments may also use transparent electrodes 14 as described herein.

Figure 11:
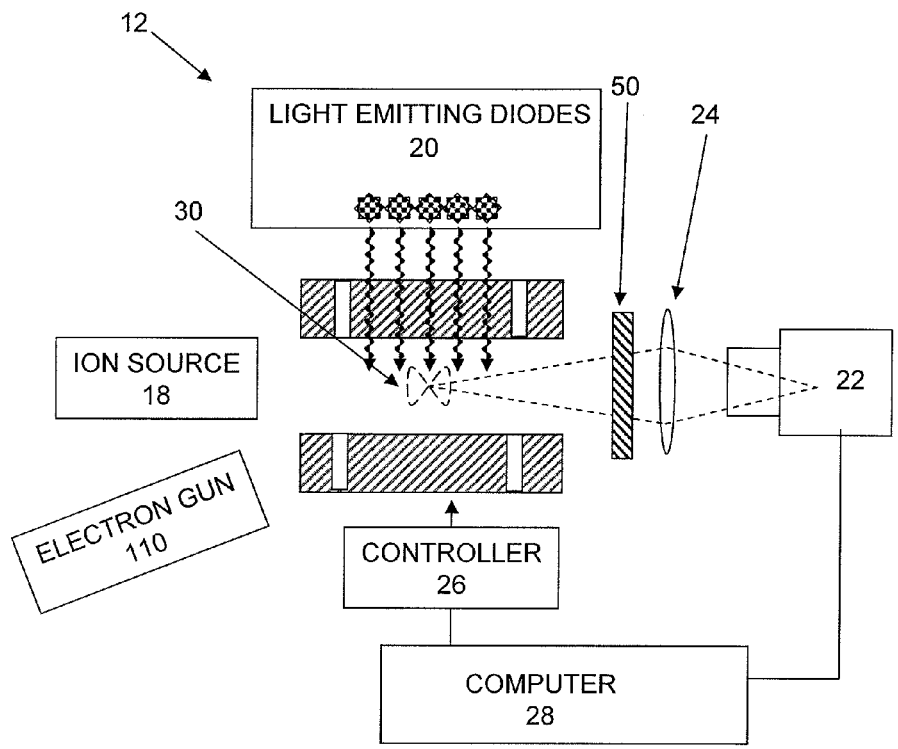
FIG. 11 illustrates another embodiment of an apparatus according to the present invention where photons are detected at an imaging device. Images of the ion trajectories inside a linear ion trap may be used for mass analysis with or with out scanning a supplementary resonance signal applied to two opposing electrodes. Long exposure times are possible due to the long storage times of the ions. For example, ions can be trapped for days, thereby allowing for long exposure or study.

FIG. 11 illustrates another embodiment of an apparatus according to the present invention where photons are detected at an optical detector 22. Images of the ion trajectories 30 inside a linear ion trap 12 may be used for mass analysis with or with out scanning a supplementary resonance signal applied to two opposing electrodes 14. Long exposure times are possible due to the long storage times of the ions. For example, ions can be trapped for days, thereby allowing for long exposure or study. The controller 26 may be used, for example, to control RF and DC signals produced by the electrodes 14. This embodiment also includes an electron gun 110. The electron gun 110 can be used, for example, to change the charge state of particles in the trapping chamber 16. The energy source 20 may, for example, provide energy to the trapped ions through a transparent electrode 14. Alternatively, the energy source 20 may provide energy via openings between electrodes 14, or through non-conductive openings in electrodes 14.

Figure 12:
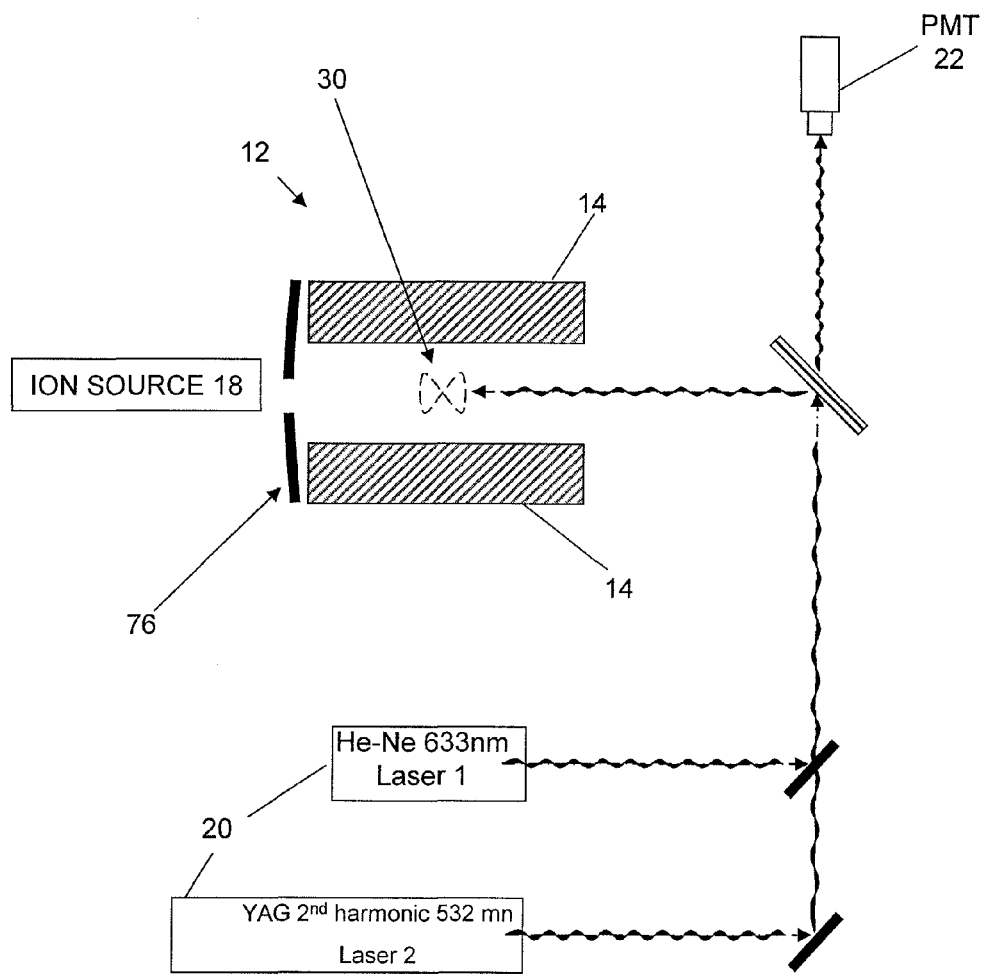
FIG. 12 illustrates another embodiment of an apparatus according to the present invention where the ion trajectories are imaged inside a linear ion trap. Ions may also be resonated into the laser beams and the emission signal measured at a PMT. Two lasers may be modulated to differentiate the emission signal from two different florescent tags. Long exposures are possible due to the trapping of the ions.

FIG. 12 illustrates another embodiment of an apparatus according to the present invention showing synchronized z-axis laser excitation and emission measurement with an optical detector 22. In that embodiment, the ion trajectories 30 are imaged inside a linear ion trap 12. Ions may also be resonated into the laser beams and the emission signal measured at a PMT 22. Two lasers 20 may be modulated to differentiate the emission signal from two different florescent tags. Long exposures are possible due to the trapping of the ions.

Figure 13:
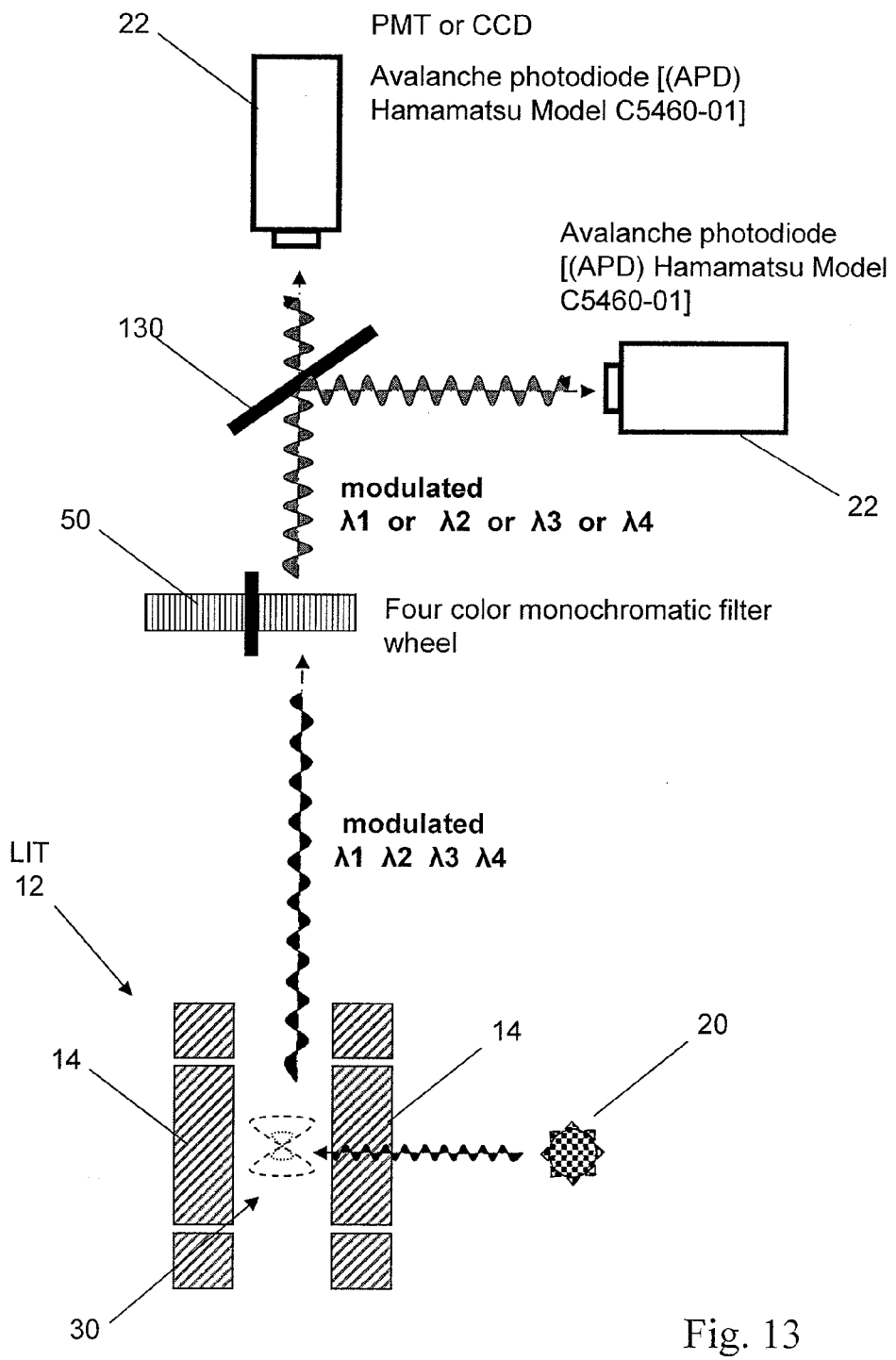
FIG. 13 illustrates another embodiment of an apparatus according to the present invention where a rotating filter wheel is used to measure the emission photons at multiple wavelengths using one or more detectors with a beam splitter.

FIG. 13 illustrates another embodiment of an apparatus according to the present invention where a rotating filter wheel 50 is used to measure the emission photons at multiple wavelengths using one or more detectors 22 with a beam splitter 130.

Figure 14:
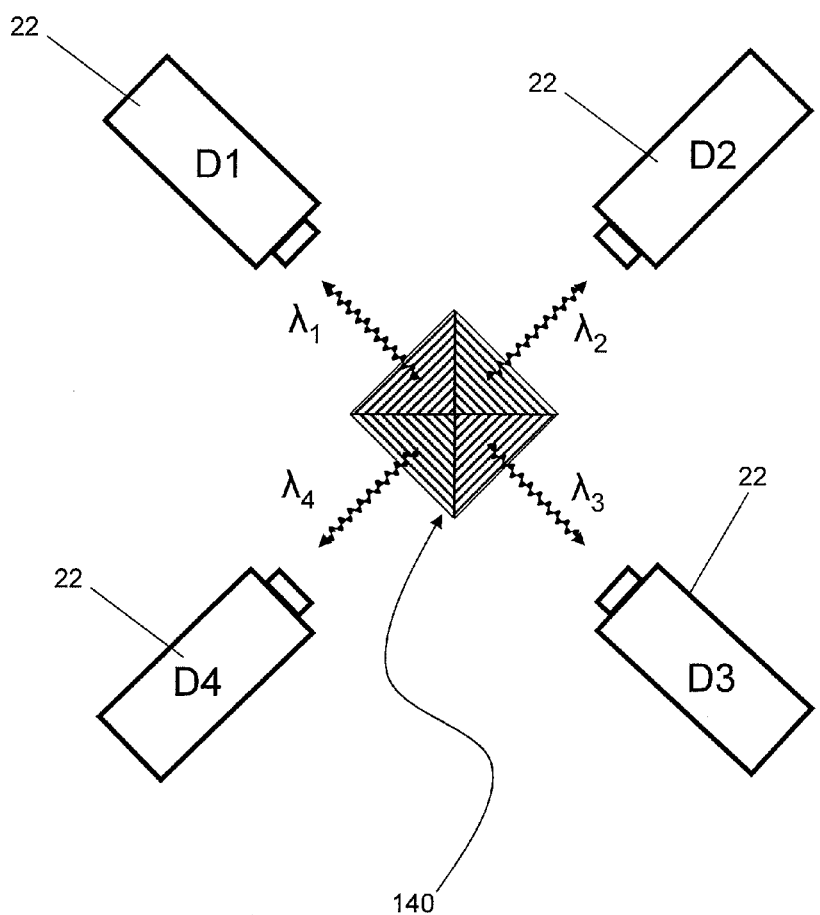
FIG. 14 illustrates another embodiment of an apparatus according to the present invention where a reflective pyramid mirror is used to detect multiple frequencies of photons. The pyramid shaped optical element could be, for example, a four sided prism.

FIG. 14 illustrates another embodiment of an apparatus according to the present invention where a reflective pyramid mirror 140 is used to detect multiple frequencies of photons. The pyramid shaped optical element could be, for example, a four sided prism. This embodiment, for example, allows for the use of multiple detectors 22 without requiring the detectors 22 to be in close proximity to each other. This is particularly important, for example, because the detectors 22 are sometimes physically large and difficult to arrange close together.

Figure 15:
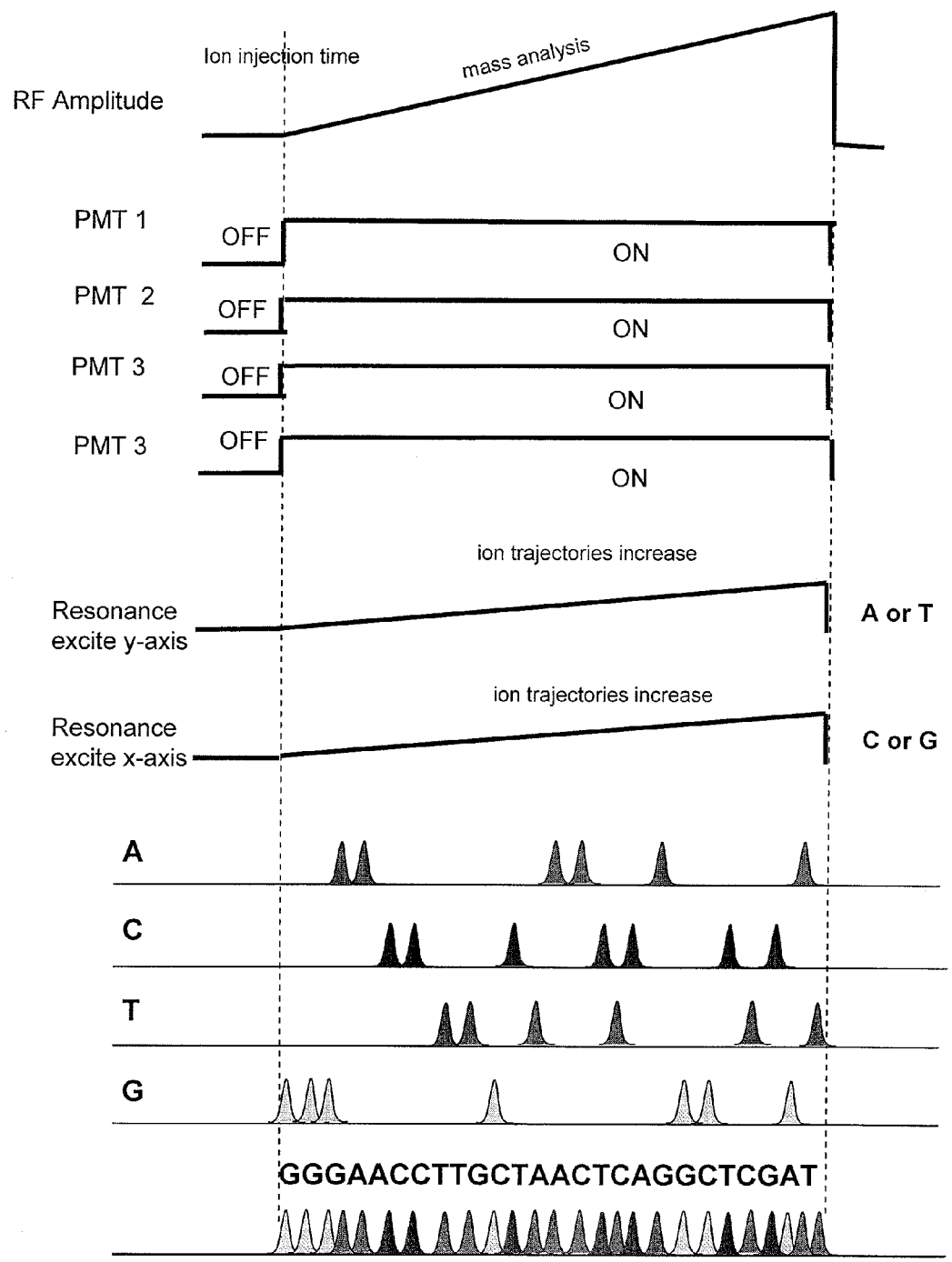
FIG. 15 illustrates a timing diagram where the RF amplitude and the resonance excitation amplitudes are increased to drive select m/z ions into resonance excitation orbits so that they can be detected in larger orbits. Lasers beams are used near the poles of each electrode to excite the specific m/z at a select frequency. Using this type of scan mode (RF amplitude ramp) even if the ion is not ejected by the resonance excitation signal, the ions would eventually be ejected once they fall outside the stability diagram whether in a LIT or a 3D in trap. For a different timing diagram see FIG. 2.

FIG. 15 illustrates a timing diagram for gas phase DNA sequencing by LIT 12 with optical detection. In that embodiment, the RF amplitude and the resonance excitation amplitudes are increased to drive select m/z ions into resonance excitation orbits so that they can be detected in larger orbits. Lasers beams are used near the poles of each electrode to excite the specific m/z at a select frequency. Using this type of scan mode (RF amplitude ramp) even if the ion is not ejected by the resonance excitation signal, the ions would eventually be ejected once they fall outside the stability diagram whether in a LIT or a 3Dion trap. For a different timing diagram see FIG. 2.

Figure 16B:
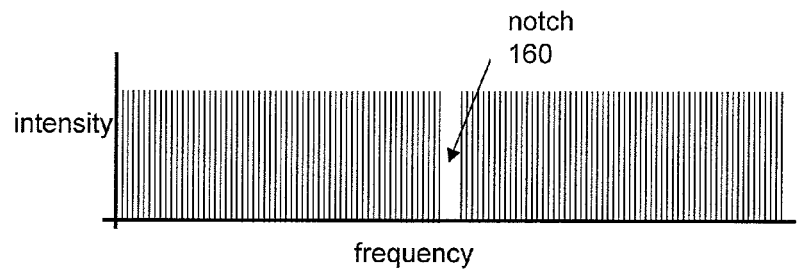
FIGS. 16A and 16B illustrate another embodiment of an apparatus according to the present invention where ions are mass analyzed in the center of the trap by resonantly exciting ions of all other masses except the m/z of interest. A sum-of-sines or SWIFT waveform is applied to the x-rods and a separate waveform is applied to the y-rods to excite all ions except at the notched frequency. The center region is occupied by non-resonance ions of a known m/z. The photons from these ions can be counted by using a PMT. Since each mass will be terminated with an A, T, C or G the sequence can be determined. Note that four different light sources are used and helium may or may not be continuously used in the trap at 1 mTorr.
Figure 16A:
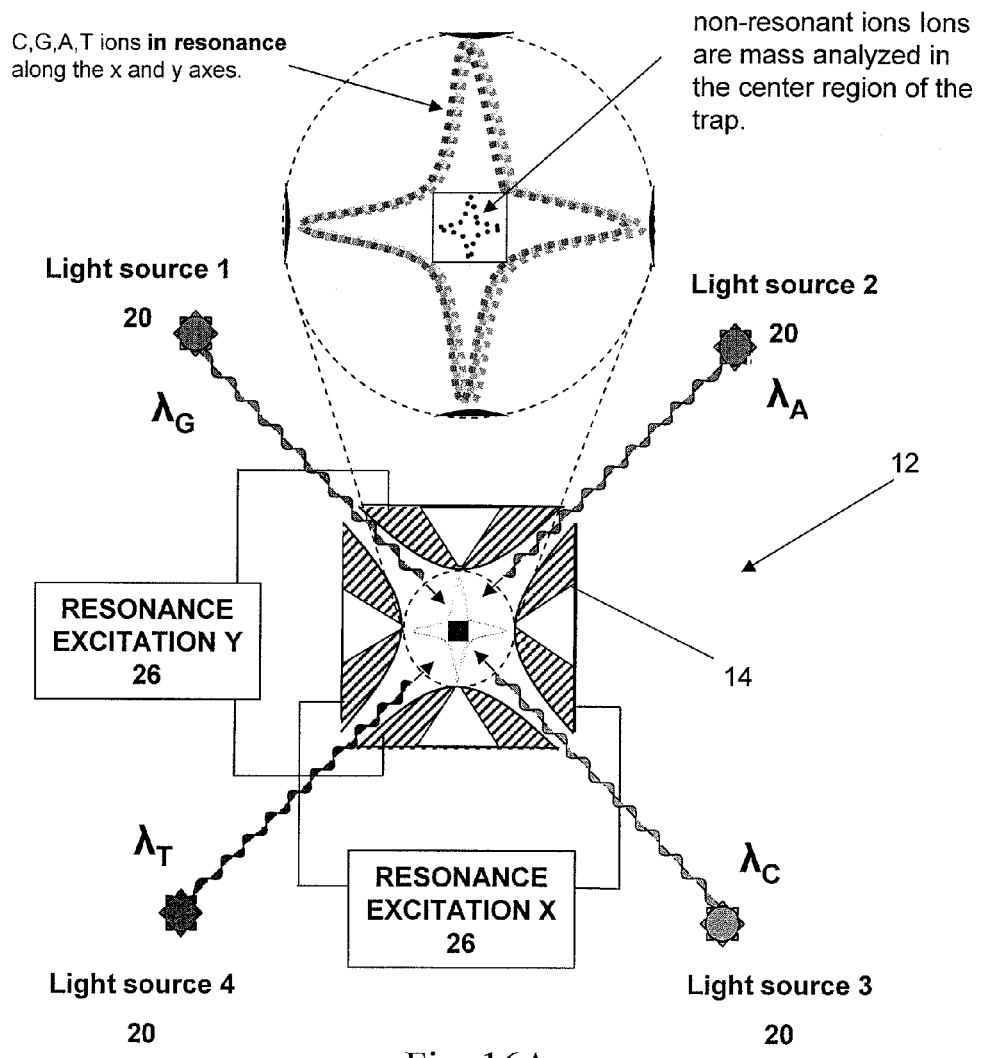

FIGS. 16A and 16B illustrate another embodiment of an apparatus according to the present invention where ions are mass analyzed in the center of the trap 12 by resonantly exciting ions of all other masses except the m/z of interest. A sum-of-sines or SWIFT waveform is applied to the x-rods 14 and a separate waveform is applied to the y-rods 14 to excite all ions except at the notched frequency 160, as illustrated in FIG. 16B. The center region is occupied by non-resonance ions of a known m/z. The photons from these ions can be counted by using a PMT 22 (not shown). Since each mass will be terminated with an A, T, C or G the sequence can be determined. Note that four different light sources 20 are used and helium may or may not be continuously used in the trap 12 at 11 Torr.

Figure 17:
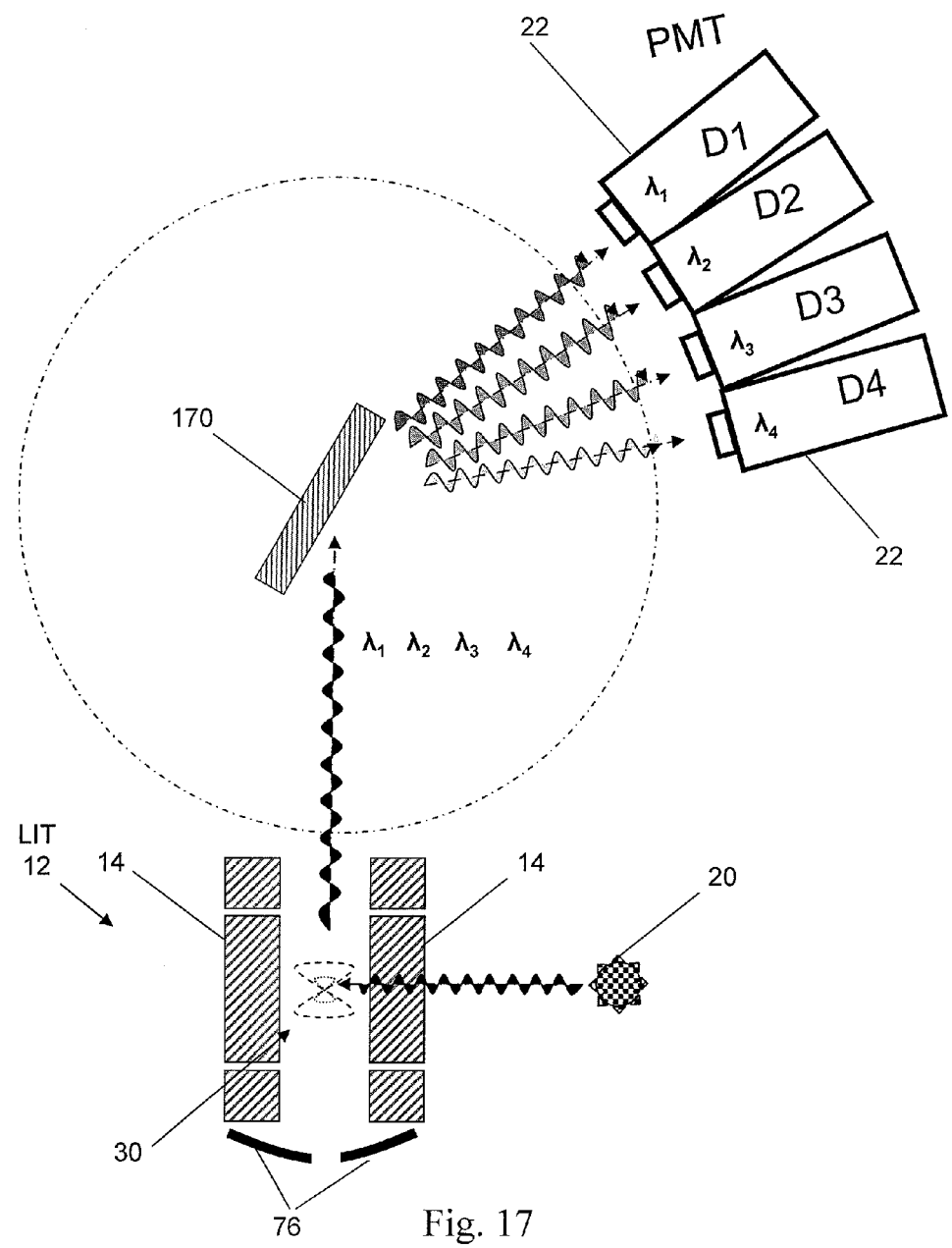
FIG. 17 illustrates another embodiment of an apparatus according to the present invention where an optical scheme is used with multiple detectors for on-axis detection of photons at four different wavelengths. A grating or prism is used to deflect the light from the specified region of the LIT to the detector. An FFT or image measurement could be made using this setup.

FIG. 17 illustrates another embodiment of an apparatus according to the present invention with on-axis detection of photons at four different wavelengths. In that embodiment, an optical scheme is used with multiple detectors 22 for on-axis detection of photons at four different wavelengths. A grating or prism 170 is used to deflect the light from the specified region of the LIT 12 to the detectors 22. An FFT or image measurement could be made using this setup.

Figure 18:
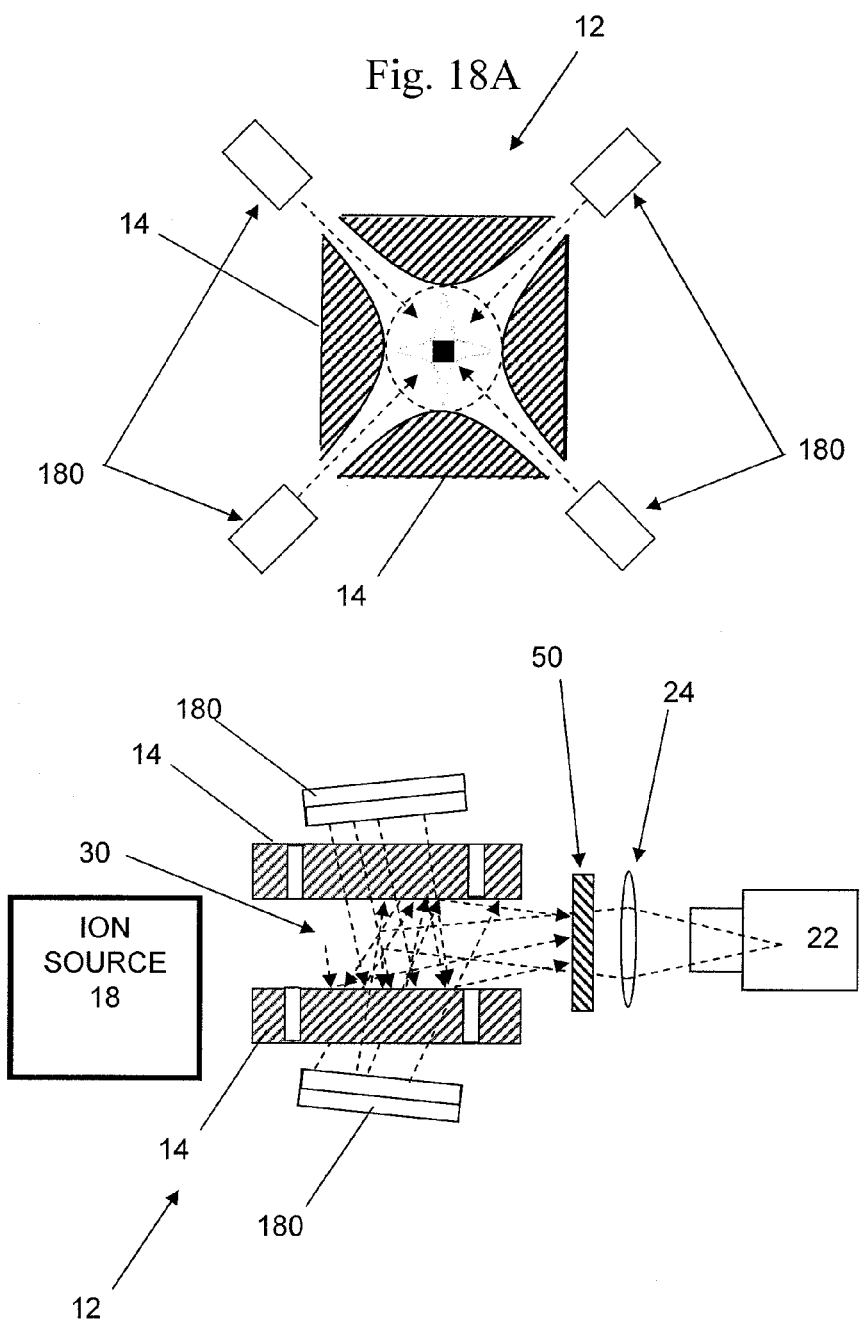
FIGS. 18A and 18B illustrate another embodiment of an apparatus according to the present invention where all electrode surfaces are reflective so that the quadrupole acts like a light pipe. Light exiting along the asymptotes is reflected back into the cell toward one end of the quadrupole using mirrors until the light exits to a photo multiplier tube (PMT). Note that a reflector light collector as shown in FIG. 9 can be used in place of the detector shown in this figure so that the maximum amount of light can be collected.

FIGS. 18A and 18B illustrate another embodiment of an apparatus according to the present invention where all electrode 14 surfaces are reflective so that the quadrupole acts like a light pipe. Light exiting along the asymptotes is reflected back into the cell toward one end of the quadrupole using angled mirrors 180 until the light exits to a photo multiplier tube (PMT) 22. Note that a reflector light collector as shown in FIG. 9 can be used in place of the detector shown in this figure so that the maximum amount of light can be collected.

Those and other variations and embodiment of the present invention are contemplated according to the teachings presented herein.

Ion Imaging

Figure 19:
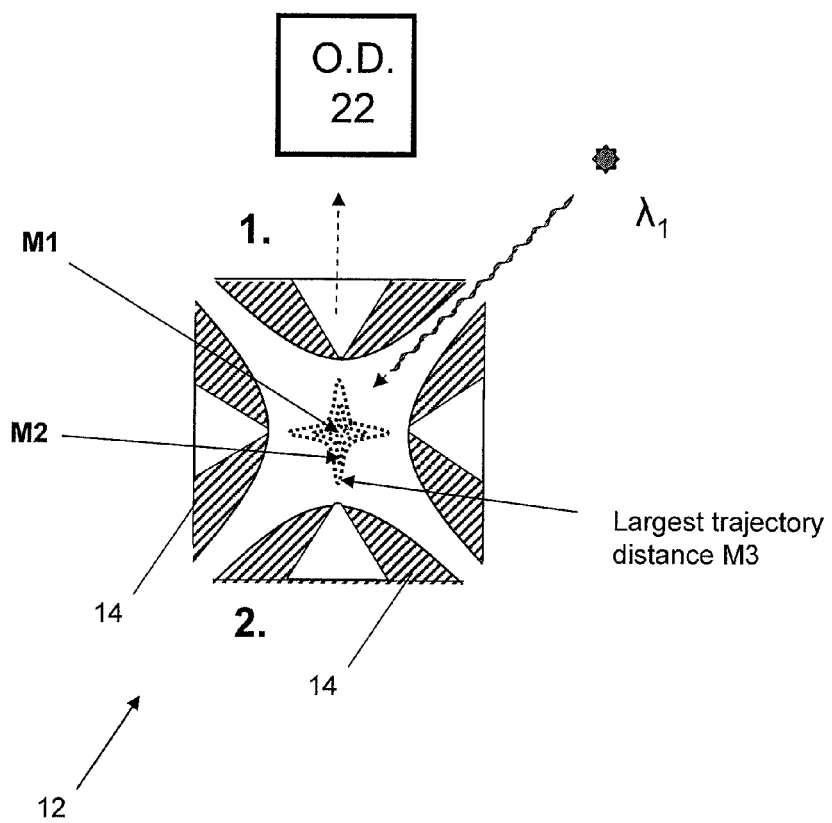
FIG. 19. Illustrates another embodiment of an apparatus according to the present invention with a simplified cross-section of a linear ion trap where three different m/z ions are trapped inside. A dipole waveform may be added to opposite rods (1 and 2) for resonance excitation with or without damping gas. Imaging or photon counting with FFT analysis in an inhomogeneous fashion may take place in any region of the trapping volume. The main RF may be scanned or the dipole resonance frequency may be scanned. For the latter case, the ions can remain inside the trap for long measurement times. Note that the ions of the largest mass are held closer to the center of the trap unless they are resonantly excited outward at which point they will gain enough energy to have orbits/trajectories outside the lower m/z ions.

FIG. 19 illustrates another embodiment of an apparatus according to the present invention with a simplified cross-section of a linear ion trap 12 with three different m/z ions are trapped inside. This embodiment illustrates photon and m/z detection using ion imaging. A dipole waveform may be added to opposite rods (1 and 2) for resonance excitation with or without damping gas. Imaging or photon counting with FFT analysis may take place in any region of the trapping volume in an inhomogeneous fashion. The main RF may be scanned or the dipole resonance frequency may be scanned. For the latter case, the ions can remain inside the trap 12 for long measurement times.

The optical detector 22 will now be described in more detail. As mentioned above, the optical detector may be, for example, photon detector or imager, and is used to capture images indicative of the trapped ions. The optical detector 22 may be an imaging device or PMT and may be, for example, a device that uses photographic film, a charge coupled device ("CCD"), or anything else for capturing visible or invisible light, such as infrared light, ultraviolet light, or for capturing other energy such as x-rays indicative of the ions in the ion trap. The optical detector 22 may capture images in black and white, in color, in false color, or in other manners. The optical detector 22 may include or be used in conjunction with a lens or other devices for focusing or adjusting the operation of the imaging device or PMT. The optical detector 22 could focus along the axis of the 2D quadrupole field linear ion trap 12.

The optical detector 22 could also be modulated with the instrument so that it takes an image at certain times during an ion motion. The optical detector 22 may capture a picture from the ion trap 12, or it may perform some other "imaging" or analysis. For example, the position of the emitted ions and their wavelength of emission and m/z would be recorded during the mass analysis scan. Repetitive scans are possible since the analysis inside the ion trap 12 is non-destructive until the ions are removed form the trap 12.

The particular location of the optical detector 22 will vary depending on the particular application. For example, the distance between the optical detector 22 and the ion trap 12 will usually be such that the emitted photons can be made to focus. However, in some embodiments it may be desirable to view the ions in an out of focus mode. The location of the optical detector 22 relative to the ion source 18 and any other devices, such the energy source 20, may also vary. For example, it may be desirable for the optical detector 22 to be oriented so as to not capture light or energy from sources other than the ions in the ion trap 12. In other embodiments, the location of the optical detector 22 may be dictated by the direction in which ions produce light or energy when excited by the energy source 20. For example, the direction in which light or energy is produced by the excited ions may be a function of the direction from which the energy from the energy source 20 is received.

In some embodiments, the optical detector 22 may capture the entire width and height of the ion clouds in the trap 12. For example, in a typical embodiment the optical detector 22 may capture an area of 20 mm by 20 mm, although larger and smaller areas may also be used. In other embodiments, the optical detector 22 captures less than the entire width and height of the trapped ions. For example, 1 mm by 1 mm. A smaller area may be desired, for example, when focusing on an area away from the center of the ion trap 12 in order to capture information on ions having a trajectory taking them away from the other ions.

In some embodiments, more than one optical detector 22 is provided. For example, two or more optical detectors 22 may be provided, with one optical detector 22 capturing the entire width and height of the trapped ions, and another optical detector 22 capturing a small portion of the trapped ions. In other embodiments, two or more optical detectors 22 may capture the same imaging area, but will capture different wavelengths of light or energy. In other embodiments, one optical detector 22 may be used to capture different imaging areas and/or to capture different wavelengths of light or energy. Other variations and combinations are also possible. Many types and variations of optical detectors 22 may be used with the present invention. In general, more resolution and greater sensitivity is desired. However, in some embodiments, other factors, such as cost or other performance specifications may be more important than maximum resolution and sensitivity. Multiple optical detectors 22 may also be incorporated to simultaneously capture different wavelengths of light. Additionally, different light optics, including lenses, prisms, mirrors, choppers, filters etc. may be employed for the specific experiments to capture the proper photon signal and the highest number of photons.

Figure 22:
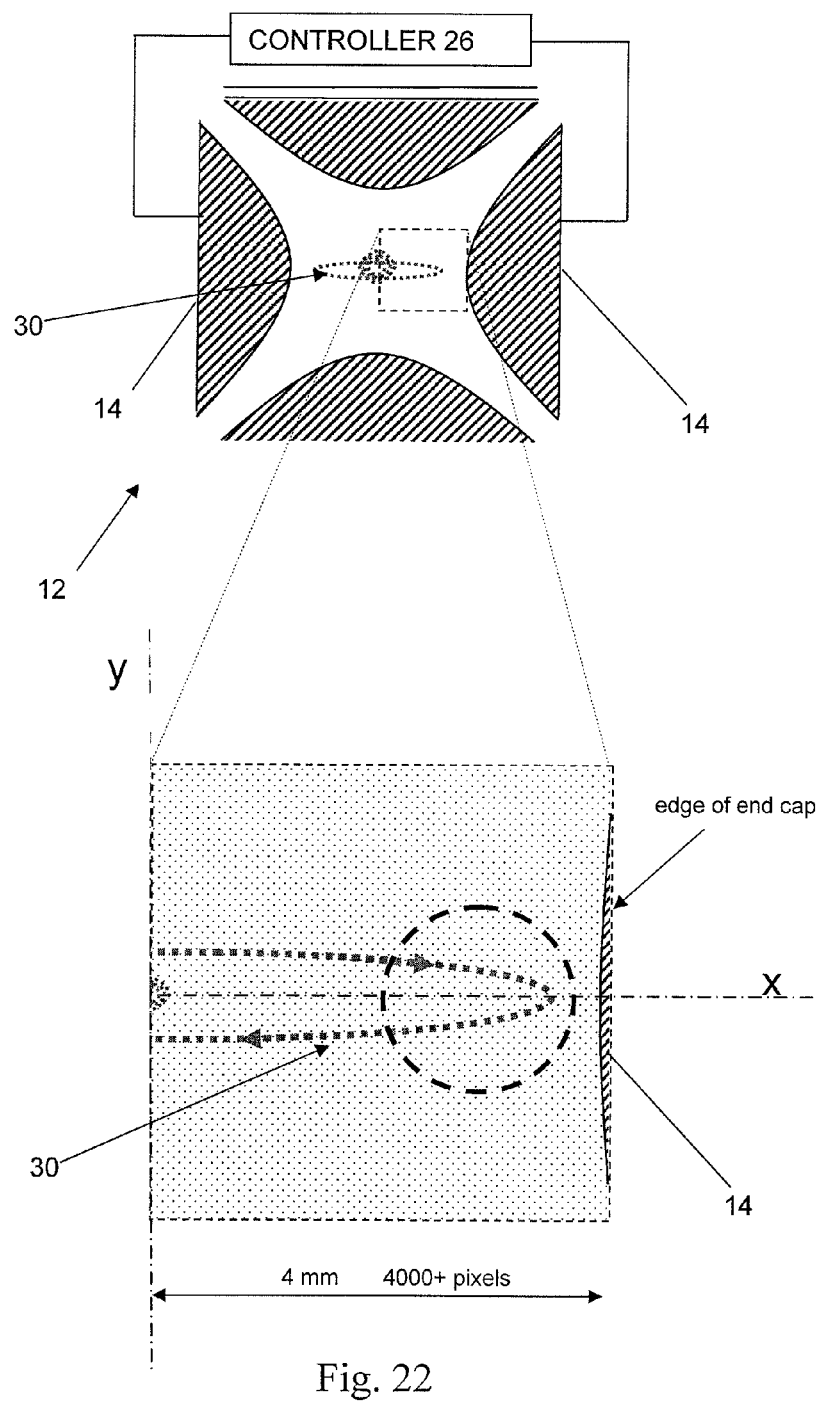
FIG. 22 illustrates another embodiment of an apparatus according to the present invention where ion images are shown with a high resolution camera.

FIG. 22 illustrates another method according to the present invention. In one embodiment, the method includes injecting one or more ions, containing the ions, exciting the ions, and imaging the ions. Imaging the ions may include, for example, capturing energy produced by the ions in response to excitation. FIG. 22 illustrates the imaging of the ions, in which a portion of the area (shown as the enlarged area at the bottom of FIG. 22) within the ion trap is imaged so that the ions in that area are imaged. The imaging can be selective so that, for example, ions of a certain mass are perturbed or excited so that those ions resonate into the window that is being imaged. The other ions tend to resonate such that they do not enter the area to be imaged, or they spend relatively little time in the area to be imaged. A portion of the imaged area may also be selectively illuminated or excited, such as by focusing a laser on a particular part of the area of interest. At the bottom of FIG. 22, there is a dashed line circle which may represent an area illuminated or excited by a laser 20 or some other narrow beam energy source 20.

Another method according to the present invention includes imaging the ions during some perturbation of the ions. For example, the ions may be perturbed electrically, such as with electromagnetic forces, the ions may be perturbed by one or more gases introduced into the ion trap, and the ions may be perturbed by photon or other energy absorption. For example, the ions could be imaged as precursor molecular ion are fragmented by collisions with a gas such as helium or by photodissociation (PD) or by electron capture or electron transfer reactions or some other means which deposit internal energy into the ion. The fragments may or may not contain a portion of a chromophore or a fluorescent tag that can then be used to view the product ions. These ions will be at a lower mass, but not necessarily a lower m/z. The fragment ions that fluoresce will give an indication what ion contains the tag and thus what functional group the tag must be bound to. The degree of fluorescents will also tell how many tags might be on a particular fragment ion or the abundance of a particular fragment. The abundance of the fragment signals would indicate the amount of energy deposited in the excitation process.

Another method according to the present invention includes varying the frequency of the oscillating electric field of the ion trap, varying the amplitude of the oscillating electric field of the ion trap, varying both the frequency and the amplitude of the oscillating electric field, and adding additional signals or magnetic fields to the ion trap. By varying one or both of the amplitude and frequency, or by adding additional signals or fields, ions with different m/z ratios will behave differently. For example, ions with different m/z ratios will oscillate at different resonant frequencies and by so doing will have trajectories that extent outside the normal damped ion trajectory region. As a result, ions with a particular m/z ratio that undergo resonance excitation will gain in amplitude that will be greater than what ions not resonantly excited would gain. The resonant ions thereby separate themselves from the other ions and allow for imaging or special photon counting or other analysis of resonant ions separate from the other ions. By varying the frequency and/or amplitude of the oscillating electric field of the ion trap, ions with different m/z ratios can be separated from the rest of the ions for study. In one embodiment, one or both of the frequency and amplitude of the oscillating electric field of the ion trap is varied within a range of values in order to separate ions of different m/z ratios.

Other variations of the present invention are also possible. For example, rather than changing the amplitude or frequency of the oscillating electric field of the ion trap, one or more additional signals or fields may be added to the ion trap. For example, a three-dimensional quadrapole ion trap has end caps that are often grounded. In one embodiment of the present invention, one or more of the end caps carry a signal that creates an electromagnetic field in the ion trap and causes resonance with select ions in the ion trap. The signal on the end caps can be varied, as described above, to resonate ions with particular m/z ratios. In another embodiment, one or more additional signals are superimposed on the signals normally used to create the electric fields for the ion trap.

In some embodiments of the present invention, ions with a particular m/z ratio are resonated to separate them from the other ions and allow for more specific imaging or other analysis. Thereafter, the resonance is changed and ions with a different m/z ratio are separated from the other ions. Additional changes to the resonance can be made to continue imaging or other analysis of ions having different m/z ratios. After the imaging or analysis of each group of ions, the ions may be allowed to remain in the ion trap after being imaged or analyzed, or those ions may be ejected from the ion trap by creating a sufficiently strong resonance for ejection. For example, in one embodiment ions are ejected after being resonated excited, thereby reducing the number and types of ions remaining in the ion trap. In another embodiment, ions remain in the ion trap after being resonated, thereby maintaining the same mix and combination of ions throughout the analysis. In other embodiments, some ions are ejected and others remain in the ion trap after imaging or other analysis.

In some embodiments, the present invention can be used to analyze the composition of unknown ions. For example, after the ions are in the ion trap, known ions or known m/z ratio ions are resonated and imaged or analyzed. This process can be performed for one or more discrete m/z ratios, or for one or more ranges of m/z ratios. As a result, the composition of the ions in the ion trap can be determined.

Figure 21:
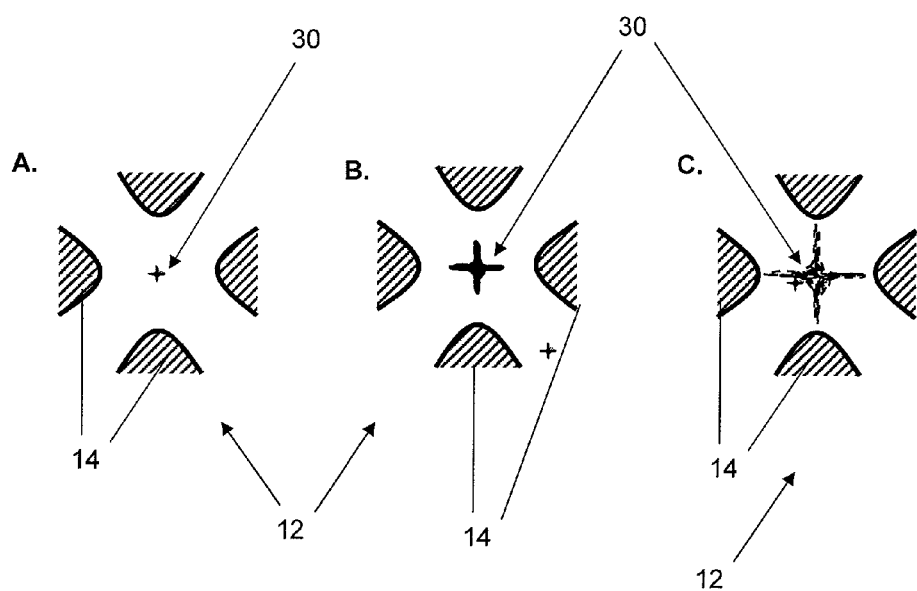
FIG. 21 illustrates another embodiment of an apparatus according to the present invention where ion images are shown of the same m/z at different points in the stability diagram or the trajectory of ion of different m/z which will have different sized orbits. Alternatively, ions can be sequentially excited to increase their trajectory/orbits from low m/z to high m/z or reverse. Ion trajectories can be increased using all other methods of m/z selected excitation using DC, RF and supplementary waveforms as shown above. Dipolar and quadrupolar excitation can be used.

FIGS. 19 and 21 illustrate simplified cross-section views of a linear ion trap 12 with three different ions trapped inside. A dipole waveform may be added to opposite rods (1 and 2 in FIG. 19) for resonance excitation with or without damping gas. If the dipole waveform is added to rods 1 and 2, the ions will tend to resonate along a horizontal path between the rods 1 and 2. The actual ion trajectories are not shown, although the position of the ions in the figure illustrate the relative amplitude of the ions paths within the ion trap 12. The difference in the amplitude of the ions paths is due to the m/z ratio or the degree of resonance excitation. In the example illustrated in FIG. 19 the ions are excited, but not ejected due to a resonance excitation at a particular q value. The m/z ratio of M1 is greater than the m/z ratio of M2, and the m/z ratio of M2 is greater than the m/z ratio of M3. Alternatively, the ion at m/z of M2 could have the greatest orbit distance from the center or ion axis of the trap 12 due to resonance excitation at M2/z in either the x or y direction.

The imaging areas may be different in size and location. A larger area would capture the entire area in which the ions are trapped. A smaller area could focus on a small area near the center of the ion trap 12. The smaller area may be used when, for example, when imaging is desired without the resonant excited ions. In other embodiments, small areas may be focused on other parts of the ion trap, such as near an edge or otherwise away from the center. Also, more or less than two areas may be imaged or photons counted in a particular ion trap and the time of that image or photon count can be varied.

FIG. 19 could also illustrate ions of the same m/z at different points in the linear quadrupole ion trap stability diagram. The ions can be excited using any means that forces the ions from the center of the trapping device outward in a larger orbit. Such signals can be of the form of a dipolar or quadrapolar excitation using an on or off resonance technique. In addition, one can apply a DC field so that the ions move the edge of the stability diagram, but they do not eject. For example, one can take an ion to a q=0.907 which is just short of instability of 0.908. In FIG. 21a, the ions exhibit relatively little excitation. At this point, the excitation resonance being imparted by the apparatus is not turned on, or it is turned on, but at a frequency and amplitude that does not significantly excite ions with the m/z ratio of those illustrated in FIG. 21a. In FIG. 21b, the ions exhibit greater excitation, as the secular frequency of the ion at m/z is closer to the resonance frequency being imparted by the apparatus. In FIG. 21c, the ions exhibit the greatest excitation as the m/z ratio of the ions has a strongly resonance with the electric fields being created by the apparatus. The frequency of the said ion of m/z can be calculated using the secular frequency equation given earlier.

Ions are sequentially excited to increase their trajectory/orbits. For example, ions with a low m/z ratio may be excited first, followed by ions with progressively greater m/z ratios. Alternatively, the process may begin with ions having a high m/z ratio and progressing to ions with low m/z ratios. In other embodiments, the ions may be excited in a non-sequential manner. For example, starting with ions having a low m/z ratio, followed by exciting ions with a high m/z ratio, followed by ions with a medium m/z ratio. Another variation would be to excite all ions except for a small $\Delta$m/z out to larger orbits leaving a small subset of the ions behind. Such a resonance excitation process is possible using a sum-of-sine comb function and other methods are possible. In this multi-ion excitation process the PMT or other optical detector 22 may look at the center of the ion trap 12 for photon emission. In this technique the ion of interest is confined to a relatively small ion orbit since it is not resonantly excited. Other variations are also possible.

Figures 31A, 31B, 31C:
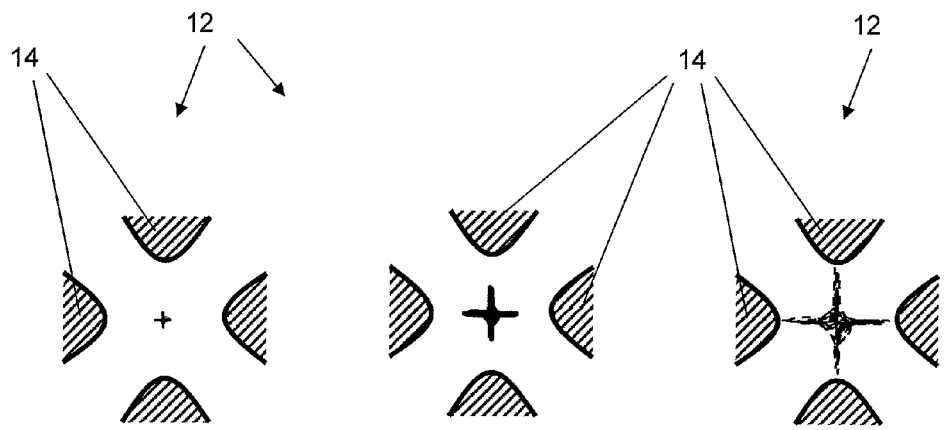
FIGS. 31A, 31B, and 31C show ion orbits in which resonance excitation causes the orbit to increase in size.
Figure 31D:
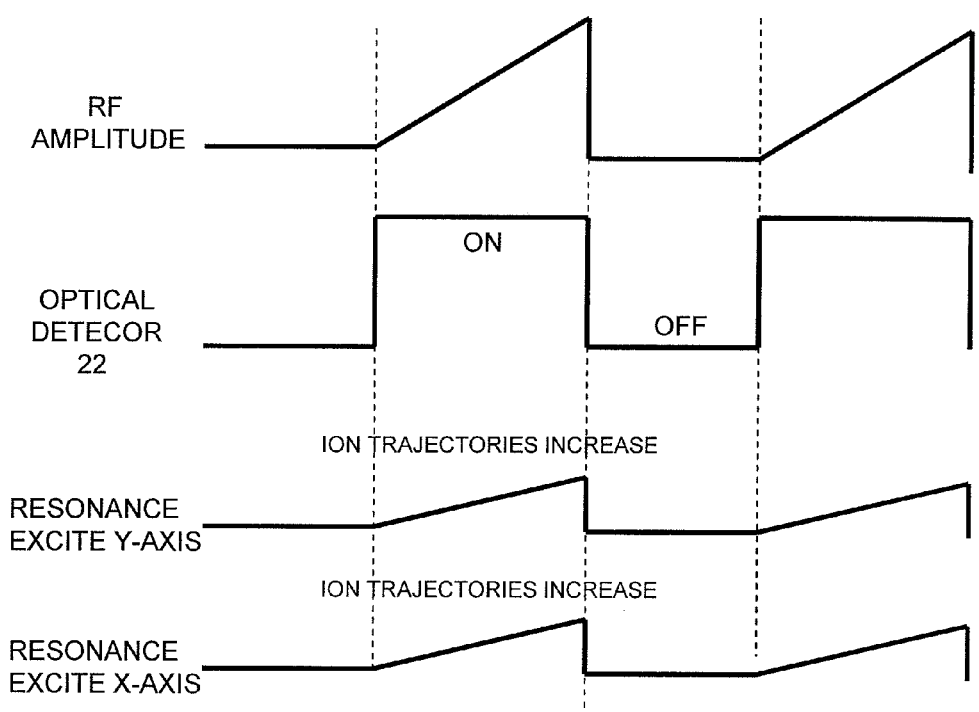
FIG. 31D illustrates a timing diagram and illustrations labeled
Figure 32A:
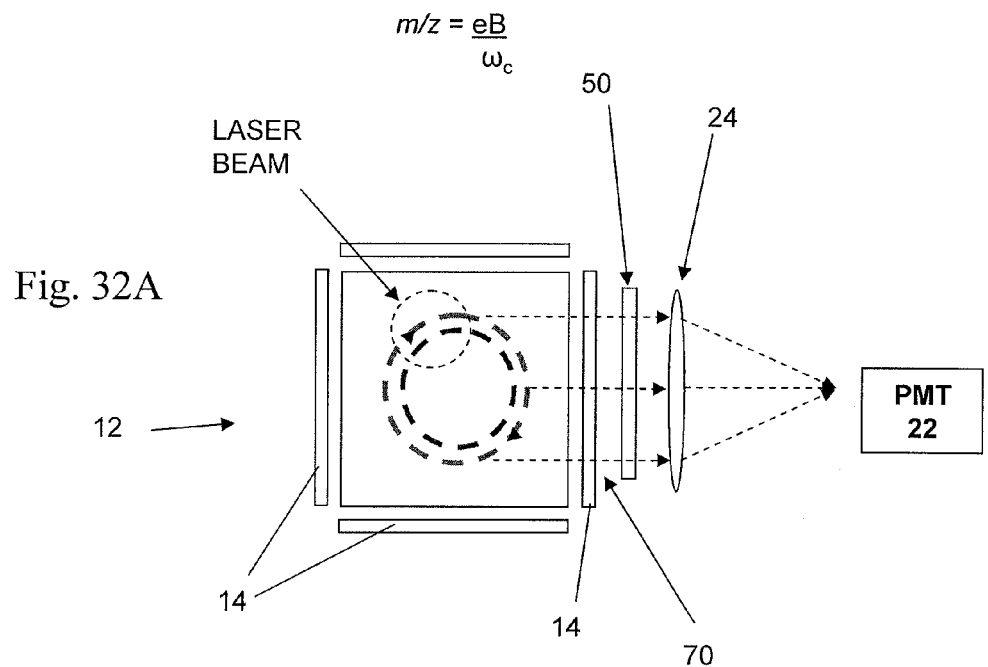
FIG. 32 is an illustration of a Fourier Transform mass spectrometer (FTMS) where an ion frequency is measured not by an induction current, but by the emission of a photon after excitation. The inhomogeneous photon emission signal will allow one to determine the emission signal frequency to high precision. The laser beam should be directed along the ion cylinder cloud as shown in the lower figure.
Figure 32B:
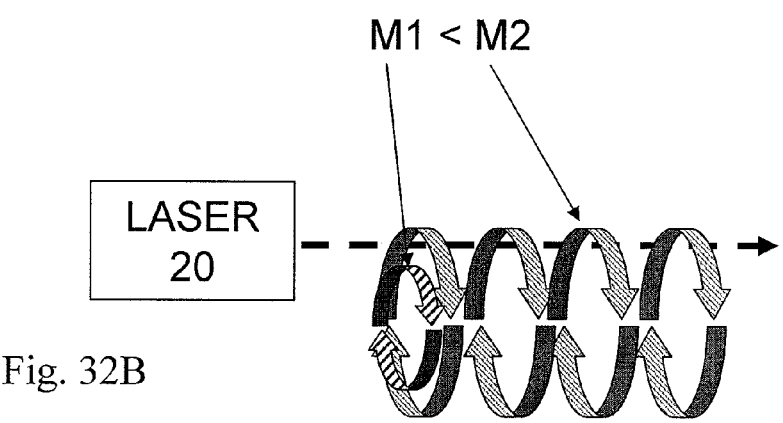

FIGS. 31A-C illustrate ion orbits in which resonance excitation causes the orbit to increase in size and FIG. 31D illustrates a timing diagram. In particular, those figures show ion images of the same m/z at different (a,q) points in the stability diagram. With reference to FIG. 31D, the first signal represents the amplitude of an RF signal being imposed on the electric fields of an ion trap 12 to excite ions of a particular m/z ratio. Typically the main RF frequency is between 1 kHz to 3 MHz. The amplitude of the RF signal is illustrated as steadily increasing so as to excite a range of m/z ratio ions in succession. For high mass work at low q ejection the RF amplitude maximum will typically not exceed 1000 Vp In another embodiment, the optical detector 22 is turned on at the same time the amplitude of the RF signal begins to increase and is turned off when the amplitude of the RF signal returns to its initial value. In other embodiments, the optical detector 22 may be turned on before the amplitude of the RF signal begins to increase in order to, for example, establish baseline or reference results. In addition, the optical detector 22 may remain on after the amplitude of the RF signal returns to its initial value. In other embodiments, the optical detector 22 may also be turned on after the amplitude of the RF signal begins to increase, and turned off before the amplitude of the RF signal returns to its initial value. Other variations are also possible.

The last two waveforms in FIG. 31 represent the resonance excitation of the ions of interest along the y-axis and/or the x-axis, respectively. In this embodiment the ion moves to higher q values (a=0) as the amplitude of the RF signal increases until it reaches the resonance excitation point. Therefore, the ions travel farther from the center of the ion trap, allowing them to be imaged or otherwise analyzed free from the interference of non-resonating ions. When the amplitude of the RF signal returns to it original value, the resonance of the ions also return to their original value and their path becomes more compact and remains closer to the center of the ion trap. See, for example, the embodiment discussed above where one m/z ion is left in the center of the trap and the other ions are resonated to outer orbits. In this case the notch can be scanned throughout the mass range, but without ejecting the ions.

Similar results would be produced by varying frequency rather than amplitude of the signal being imposed on the ion trap. As the resonance excitation frequency approaches the secular frequency of the ions of interest, the resonance of the ions will increased and the ions will travel farther from the center of the ion trap, allowing them to be imaged or otherwise analyzed. When the frequency of the RF signal reaches the optimum resonance frequency for the ions, the resonance of the ions will peak and the ions will travel farthest from the center of the ion trap and may collide with the electrode or be ejected from the trap. In some embodiments this frequency will be maintained for a period of time in order to allow for extended imaging and analysis for improved signal-to-noise measurements and thus detection limits. When the frequency of the RF signal moves away from the optimum resonance frequency for the ions, then the resonance of the ions will begin to decrease and the path of the ions will increasingly become closer to the center of the ion trap 12. A continuous leak or pulsed helium can be used to damp these ions.

Many variations are possible. For example, the amplitude of the RF signal is illustrated as increasing. In other embodiments it may start high and decrease. In other embodiments, the amplitude of the RF signal may vary in a non-uniform manner. For example, the amplitude of the RF signal may be held steady from time to time to allow additional time to image or analyze a particular group of ions. In other embodiments, the amplitude of the RF signal may increase and then decrease. In addition, although FIG. 31 illustrates controlling the amplitude of the RF signal, the frequency of the signal may also be controlled and varied. In some embodiments, the frequency may be controlled and the amplitude is constant. In other embodiments, both the amplitude and frequency are controlled and varied. In other variations the main RF frequency can remain constant and the supplemental resonance excitation amplitude and frequency can be varied to cause excitation. Other variations and combinations are also possible.

FIGS. 19 and 21 illustrates a simplified cross-section of a linear ion trap with ions paths illustrated for ions having three different m/z ratios. M1 has the most compact path within the ion trap (illustrated as white in the center of the ion trap) and stays close to the center of the ion trap. M3 has a path that extends farthest from the center of the ion trap (illustrated as dashed lines). M2 has a path (shown in solid black) that extends farther than M1 but not as far as M3.

The ions illustrated in FIG. 19 illustrate a situation in which M3 is excited or perturbed more than M2 or M1. This may be caused, for example, because M3 is being resonated more than M1 or M2 by an electric field applied to the ion trap or because M3 is absorbing more energy from the energy source than M1 and M2. Regardless of the cause, M3 travels farther from the center of the ion trap than M1 or M2 and, therefore, M3 may be specifically analyzed or imaged by focusing on an area of the ion trap where M3 travels but M1 and M2 do not travel. When it is desired to study another ion, the resonance may be changed, or the characteristic of the energy produced by the energy source may be changed so as to excite or perturb one of the other ions. As result, M3's path will become more compact and another of the ions will travel farther away from the center of the ion trap, allowing it to be imaged or analyzed apart from the other ions.

When M3 or one of the other ions is no longer desired in the ion trap, it may be excited to a point that its path extends so close to the edge of the ion trap that it is either ejected from the ion trap or it can be lost to the walls of the electrodes, leaving the other ions. One or more ions or groups of ions may be ejected, together or in succession, in order to leave a desired group of ions within the ion trap.

In another embodiment, molecular weight determinations of heavy ions can be made by resonating the ions of high m/z and imaging them. For example, one could take a 12 MDa virus particle and tag the molecule with fluorescent tag molecules to enhance its signal. Next the virus particle would be ionized and injected into a linear ion trap. The RF amplitude supplemented with resonance excitation applied to the electrodes would be scanned such that the 12 MDa ion comes into resonance and its trajectory would thus increase to a point just short of hitting the electrode. Although the ion could be ejected for the imaging experiment, the ion could also be held in resonance without ejection. To hold small ions in resonance without fragmentation the helium in the trap should be removed. The dye molecules attached to the protein complex will allow the ion to be readily seen. By the concentration of the fluorescent signal one could calculate the expected number of dye molecules on the protein complex and thus the true molecular weight for the complex. A calibration of the amount of florescence for a certain number of dye molecules could be determined.

An advantage of the optical trap according to the present invention is that the ideal electrode geometry can be used allowing the assembly to minimize field imperfections. No slots or holes or windows are required to be cut in the electrodes for ejection, to introduce light or to detect photons.

For the dual dipole excitation scan, the resonance frequencies can be set to resonate the ions at the same frequency in the two dimensions or at different frequencies. One such method could set the frequencies so that in one dimension the m/z analysis is ahead of the other dimension by $\Delta m$. For example, one could operate the mass analyzer to analyze $m_x/z=m1$ in the x-axis while the resonance frequency in the y-axis can be set to mass analyze $m_y/z=m1+\Delta m$, where $\Delta m$ can be set higher or lower to avoid simultaneous resonance excitation in two dimensions.

Although one embodiment of this invention discussed here shows a quadrupole mass analyzer, other multi-pole trapping analyzers, FTMS cells and orbitraps could be used. The present invention includes resonantly exciting the ions in such a way that mass separation occurs and the ion can then be simultaneously imaged or counted by photon emission. One or more electrodes can be used to both trap and excite ions.

Figure 36:
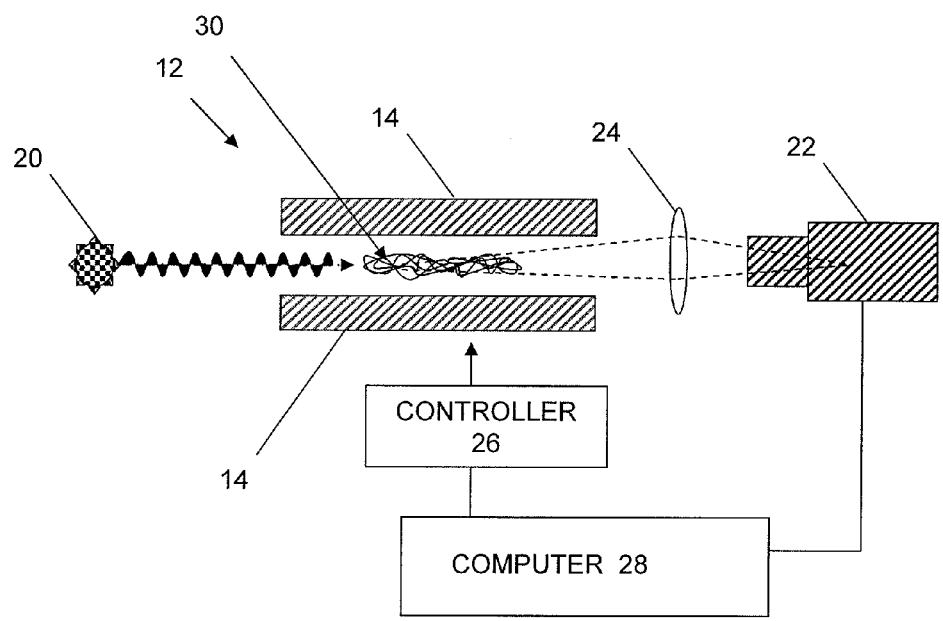
FIG. 36. Illustrates the embodiment of an apparatus according to the present invention where the long trapping path length of a LIT is used to make absorption measurements rather than emission measurements.

FIG. 36 illustrates another embodiment of an apparatus according to the present invention where the long trapping path length of a LIT 12 is used to make absorption measurements rather than emission measurements. In other words, the figure shows light absorption imaging mass spectrometry. In that embodiment, the energy source 20 is located at one end of the ion tap 12 and opposite of the optical detector 22. The optical detector 22 may be, for example, a 10+Megapixel camera. This may be done, for example, to collect an absorption spectrum from the trapped ions. Also, the illustrated embodiment does not show an ion source 18, although an ion source 18 may be provided, for example, along one of the sides of the ion trap 12 or on-axis with the excitation source 20.

Many variations and modifications are possible with the present invention. Several variations and embodiments of the present invention will now be described.

Figures 20A, 20B, 20C:
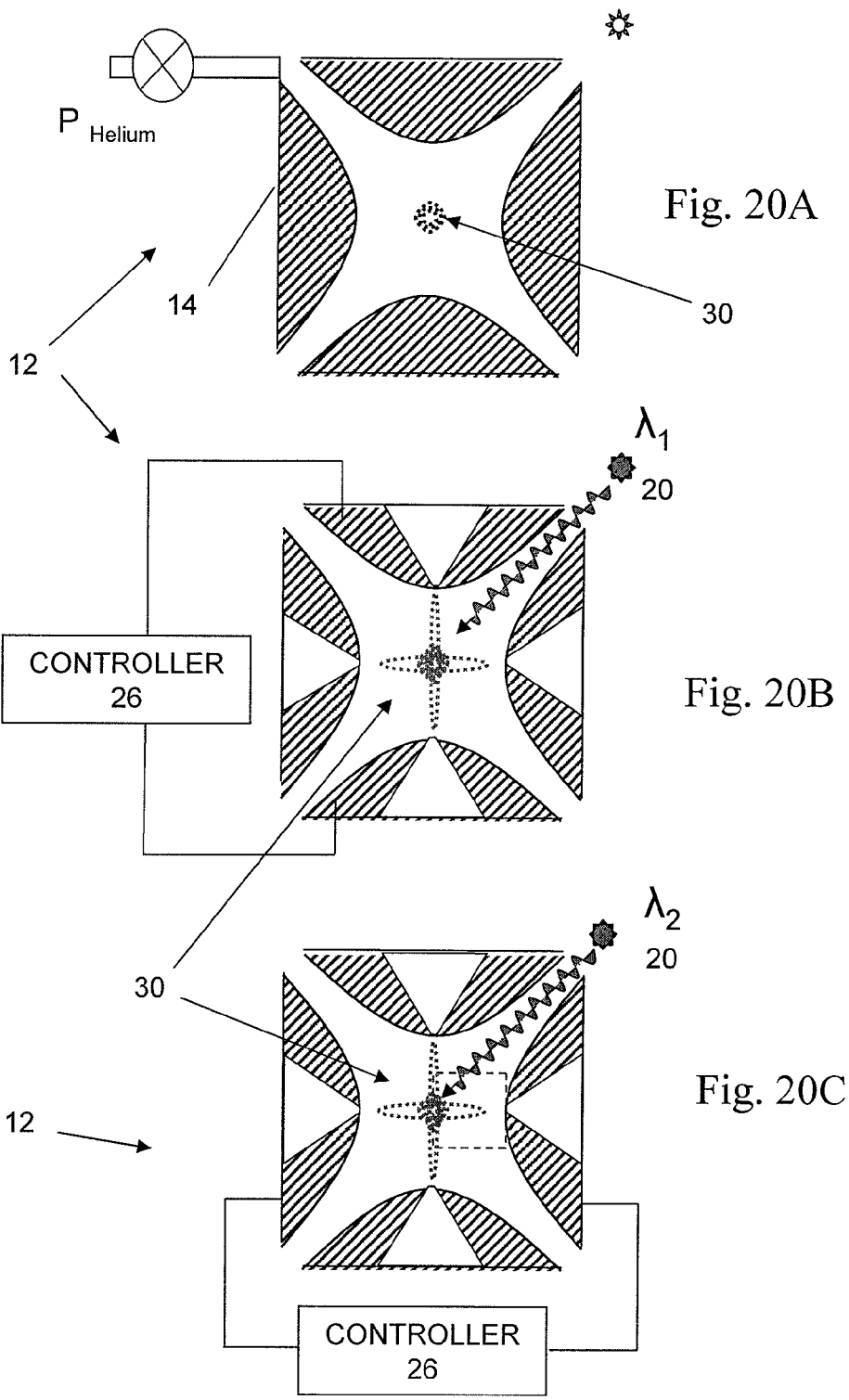
FIG. 20 illustrates another embodiment of an apparatus according to the present invention where ions of a specific mass are excited through resonance excitation and from photon excitation. Only ions that have the proper fluorescents tag and m/z will be seen in the imaged area shown by a dashed square (5 mm×5 mm). Alternatively a PMT can be used to monitor the photons emitted from ions resonantly excited into larger orbits or the damped ions depending on where the excitation laser light is focused. For example, all ions at m/z 1147 could be excited at 540 nm and the emission collected at 590 nm if they contain Cy3 labeling. Ions at m/z 1147 that contain Cy5 labeling would be excited at 620 nm and emit at 680 nm.

FIG. 20 illustrates an embodiment of an apparatus according to the present invention where ions of a specific mass are excited through resonance excitation and from photon excitation. Only ions that have the proper fluorescents tag and m/z will be seen in the imaged area shown by a dashed square. Alternatively a PMT 22 can be used to monitor the photons emitted from ion resonantly excited into larger orbits or damped ions depending on where the excitation laser light 20 is focused.

Figure 23:
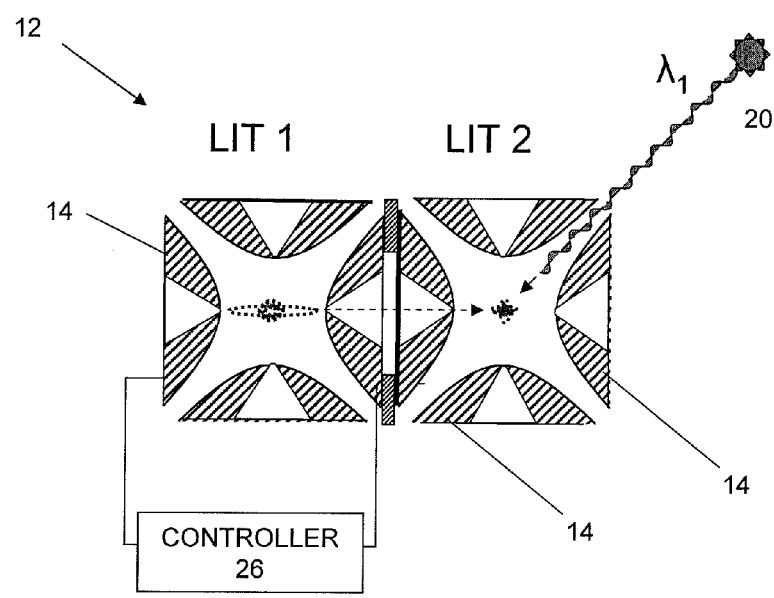
FIG. 23 illustrates another embodiment of an apparatus according to the present invention where ions are resonantly ejected from one LIT into another LIT for measurement by LIF or light scattering. An imaging camera or PMT is position to view along the z-axis of LIT 2. (not shown)

FIG. 23 illustrates another embodiment of an apparatus according to the present invention in which two ion traps 12 are used together to perform two or more analyses on ions. In the illustrated embodiment, mass analysis is performed in LIT1 and detection analysis is performed in LIT 2. In particular, the ions are resonantly ejected from LIT1 into LIT2. In LIT2, the ions are measured by LIF or light scattering. An optical detector 22, such as a PMT, may be positioned to view along the z-axis of LIT 2. (not shown)

Figure 24:
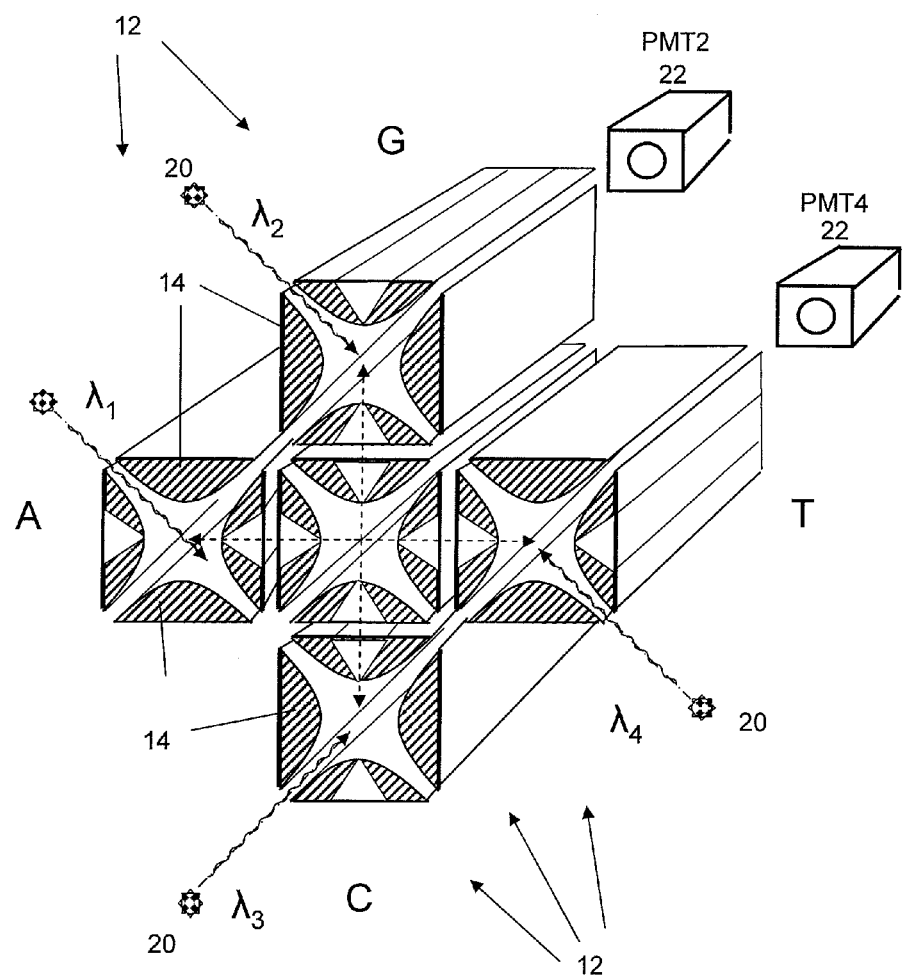
FIG. 24 illustrates another embodiment of an apparatus according to the present invention where ions are ejected from a central LIT into one of four outer LITs. The emitted photons are measured at the respective PMTs. The center trap can serve as the mass analyzer while the satellite LITs serve as the detector traps for DNA sequencing. Ions are mass analyzed and simultaneously ejected into the A, T, G and C LITs for nucleotide determination. No imaging of position is required.

FIG. 24 illustrates another embodiment of an apparatus according to the present invention in which a penta LIT may be used for DNA sequencing. In this embodiment, ions are ejected from a central LIT 12 into one of four outer LITs 12. The emitted photons are measured at the respective PMTs 22. The center trap 12 can serve as the mass analyzer while the satellite LITs 12 serve as the detector traps for DNA sequencing. Ions are mass analyzed and simultaneously ejected into the A, T, G and C LITs 12 for nucleotide determination. No imaging of position is required in this embodiment.

Figure 25:
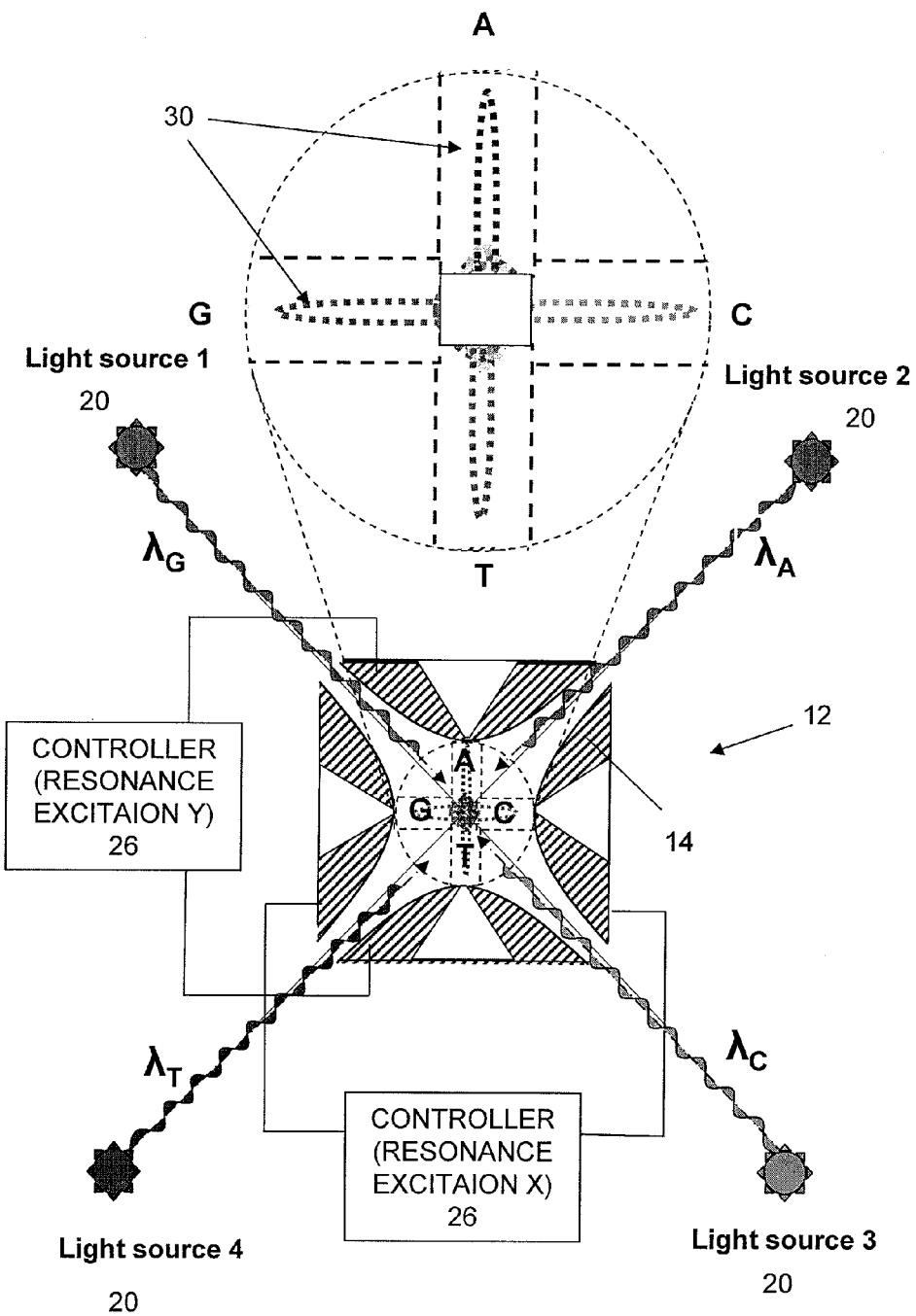
FIG. 25 illustrates another embodiment of an apparatus according to the present invention where ions are not ejected from a LIT, but remain in the trap for the measurement. Ions can be resonated into greater orbits in the x or y or both x and y dimension and the signal measured. Alternately an FFT measurement can be made directly with or without resonance excitation. Resonating the ion into a larger orbit allows for less demanding alignment and focus of the lasers and for different regions to be used for different measurements (e.g. A, T, G, and C chromophores). Ions are mass analyzed and the trajectories can be imaged or the photons are counted from each of the four rectangular areas, A, T, G and C (nucleotides). Four imaging cameras or PMTs (not shown) are position to view one of the four rectangular regions. An FFT measurement can be made for each m/z. Only one rectangle will light up, identifying the terminal nucleotide residue.

FIG. 25 illustrates another embodiment of an apparatus according to the present invention which may be used, for example, as a DNA sequencer. The embodiment, in general, is a gas phase multi-light source and multi-photo detector linear ion trap. In particular, in that embodiment ions are not ejected from a LIT 12, but remain in the trap 12 for the measurement. Ions can be resonated into greater orbit and the signal measured. Alternately an FFT measurement can be made directly with or without resonance excitation. Ions are mass analyzed and the trajectories can be imaged or the photons are counted from each of the four rectangular areas, A, T, G and C. An FFT measurement can be made for each m/z. Only one rectangle will light up, identifying the terminal nucleotide residue.

Figure 26:
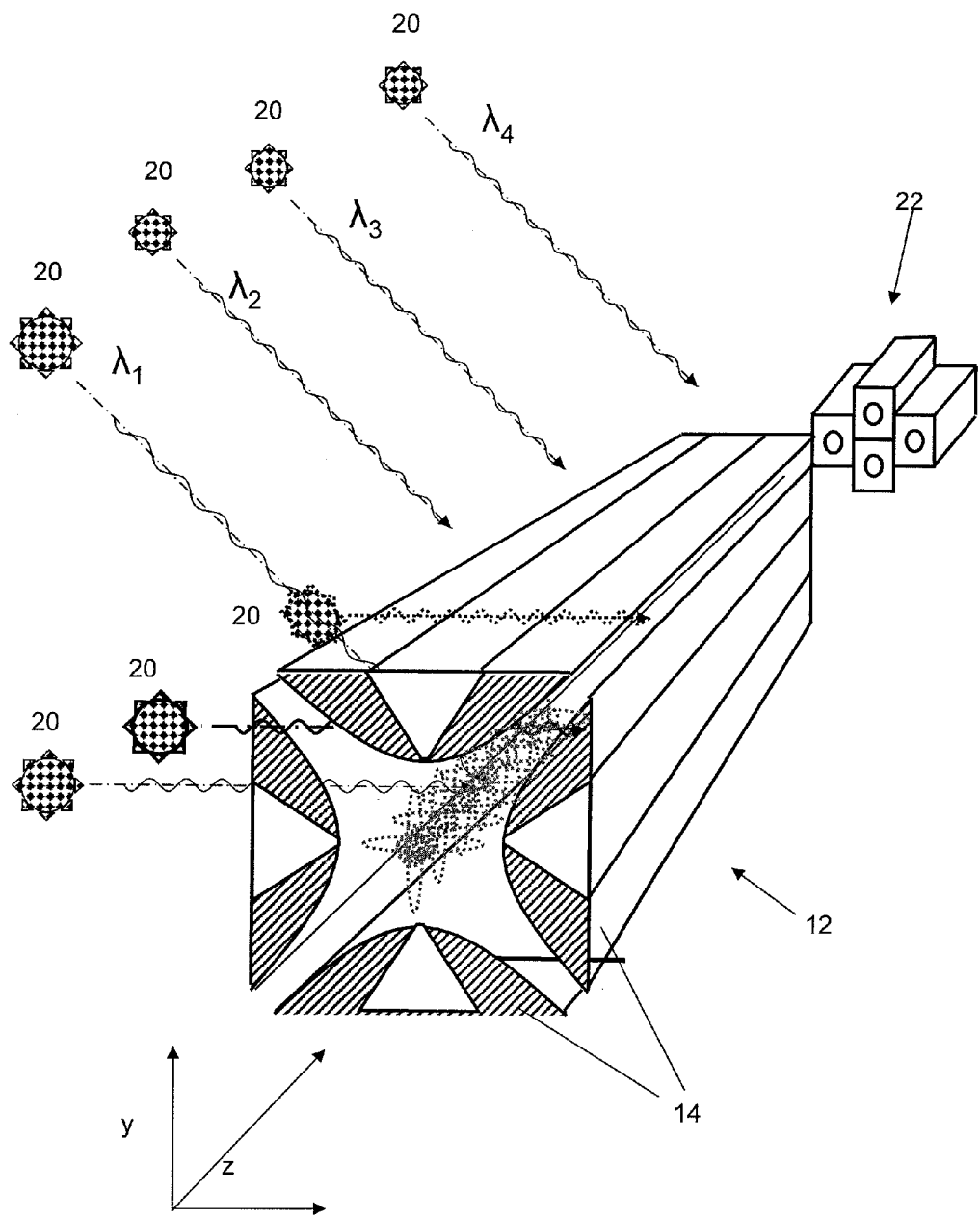
FIG. 26 illustrates four PMTs used to measure select photons in the region of interest. See FIG. 25. For example, ions with the proper fluorescent tag and resonantly excited in the x direction could emit photons that would only be detected by one of the PMT positioned along the x-axis. Ions resonantly excited in the y-direction could be detected by one of the PMT along the y-axis. Alternatively an imaging detector could be used. Ions at m/z 1147 are excited at 540 nm and the emission collected at 590 nm if they contain Cy3 labeling that will fluoresce. An FFT analysis could be applied to the signal collected at the detector.

FIG. 26 illustrates another embodiment of the present invention utilizing four PMTs 22 to measure select photons in a region of interest. This embodiment may be used, for example, in connection with the embodiment described with respect to FIG. 25. For example, ions with the proper fluorescent tag and resonantly excited in the x direction could emit photons that would only be detected by one of the PMT positioned along the x-axis. Ions resonantly excited in the y-direction could be detected by one of the PMT along the y-axis. In place of PMTs, an imaging detector or other optical detector 22 could be used. An FFT analysis could be applied to signal collect at the detector 22

Figure 27:
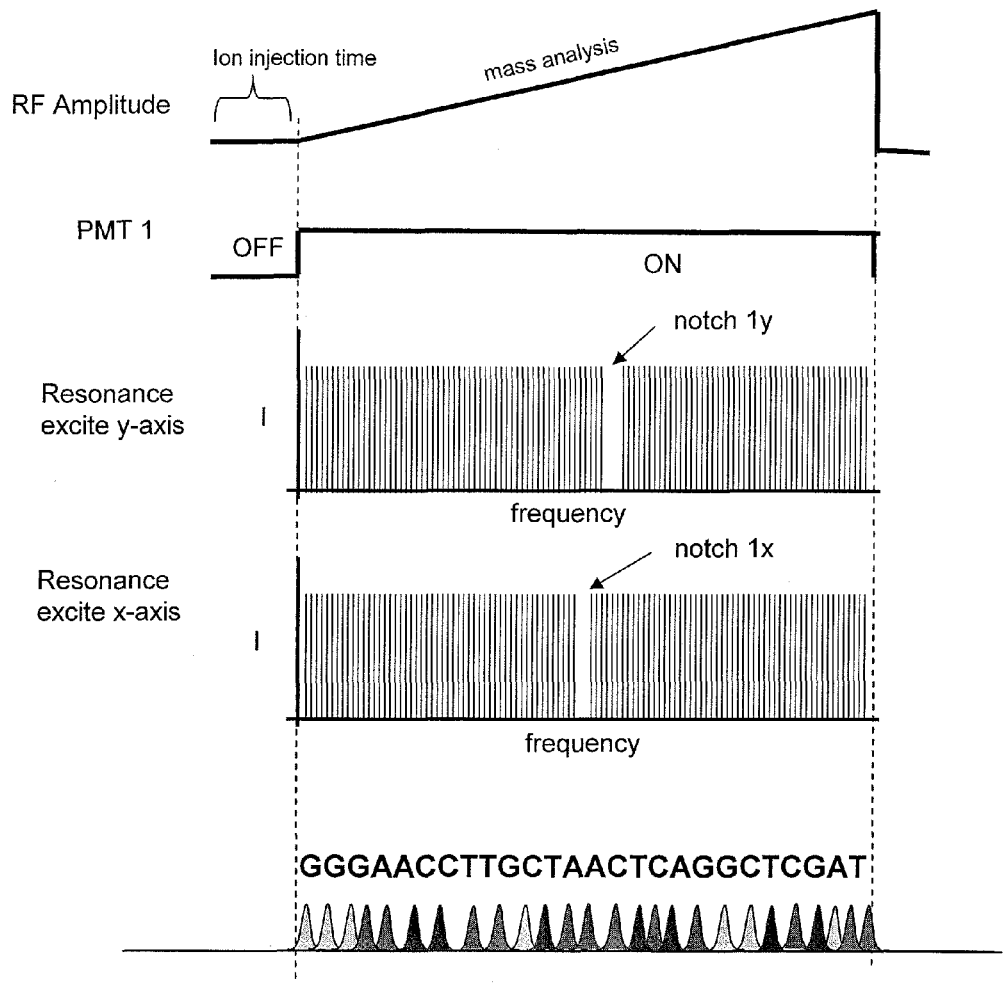
FIG. 27 illustrates a timing diagram with increasing RF amplitude. In other embodiments, the amplitude could remain fixed once the ions are trapped. A sum-of-sines resonance excitation signal is applied to the rods in both the x and y axes (or just one axis) so that select m/z ion will move in and out of resonance. Imaging or photon counting can take place at the center or the outer portions or the ion orbits.

FIG. 27 illustrates a timing diagram with increasing RF amplitude, although in other embodiments of the present invention, the amplitude could remain fixed once the ions are trapped. The timing diagram is for an embodiment of the invention for gas phase DNA sequencing by LIT 12 with optical detection. A sum-of-sines resonance excitation signal is applied to the rods in both the x and y axes (or just one axis) so that select m/z ion will move in and out of resonance. Imaging or photon counting can take place at the center or the outer portions or the ion orbits.

Figure 28:
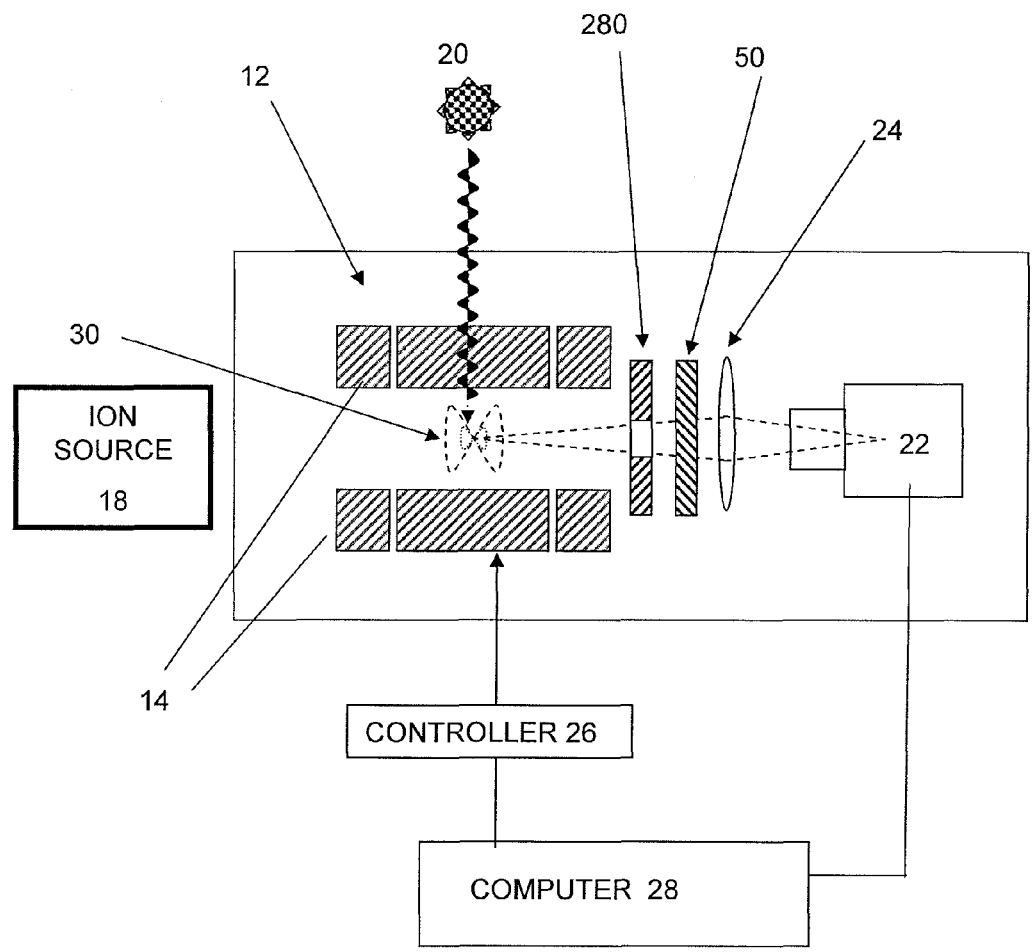
FIG. 28 illustrates the embodiment of an apparatus according to the present invention for the analyzers described in FIGS. 25-27.

FIG. 28 illustrates an embodiment of an apparatus according to the present invention for the analyzers described in FIGS. 25-27. That embodiment may be used to measure photons at the center region of the quadrupole field. The embodiment also includes a limiting aperture 280 for restricting or limiting the region of the ion trap 12 that is viewed by the optical detector 22.

Figure 29:
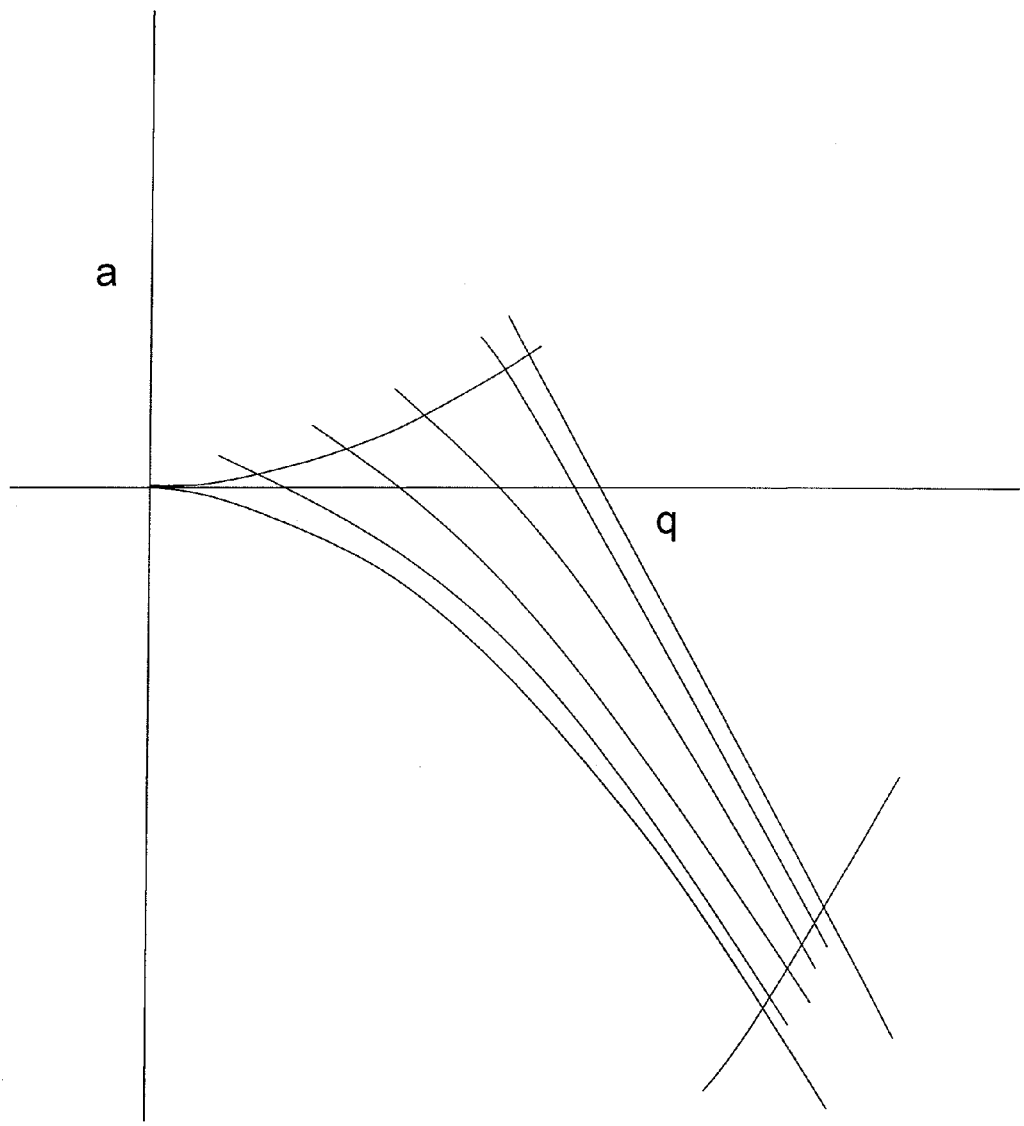
FIGS. 29 and 30 illustrate stability diagrams for the 3D quadrupole field ion trap and the 2D quadrupole field ion trap, respectively.
Figure 30:
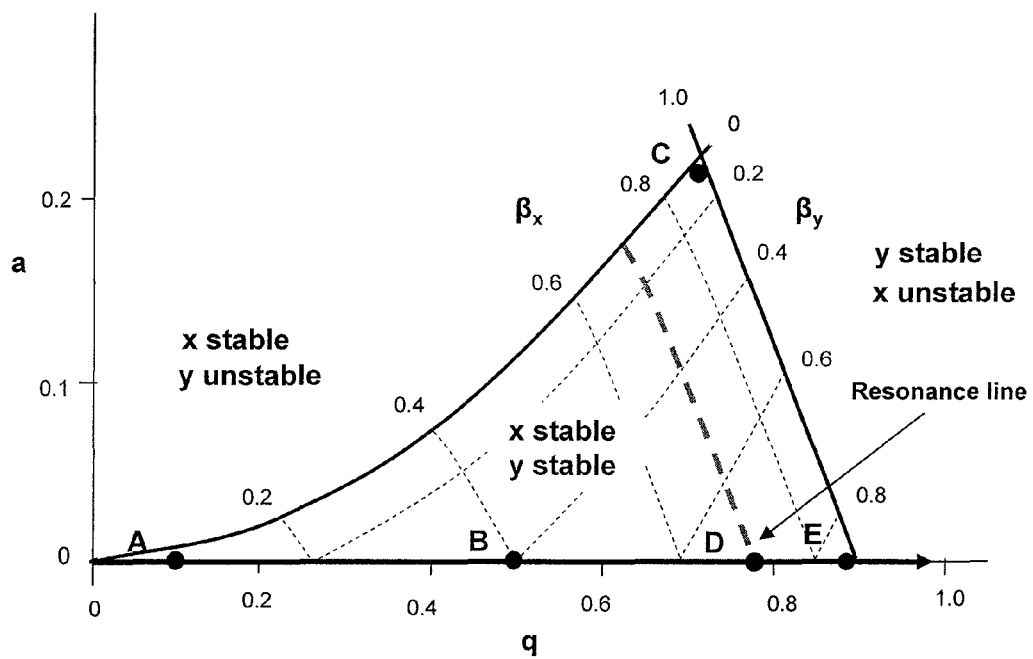

FIGS. 29 and 30 illustrate stability diagrams for the 3D quadrupole field ion trap and the 2D quadrupole field ion trap, respectively.

FIGS. 32-35 illustrate the use of a Fourier Transform method according to the present invention, although similar embodiments may also be used with imaging according to the present invention. FIGS. 32A and 32B illustrate a Fourier Transform mass spectrometer (FTMS) where an ion frequency is measured not by an induction current, but by the emission of a photon after excitation. The inhomogeneous photon emission signal will allow one to determine the emission signal frequency to high precision. The laser beam should be directed along the ion cylinder cloud as shown in FIG. 32B.

Figure 33A:
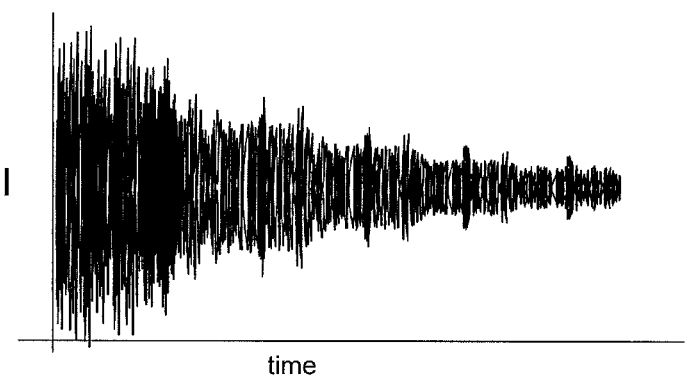
FIG. 33 illustrates that the signal over time in (a.) is transformed into a frequency spectrum in (b.) by FFT. Mass spectrum showing the secular frequency components of the ions due to the optical signal transformed into a frequency spectrum or mass spectrum.
Figure 33B:
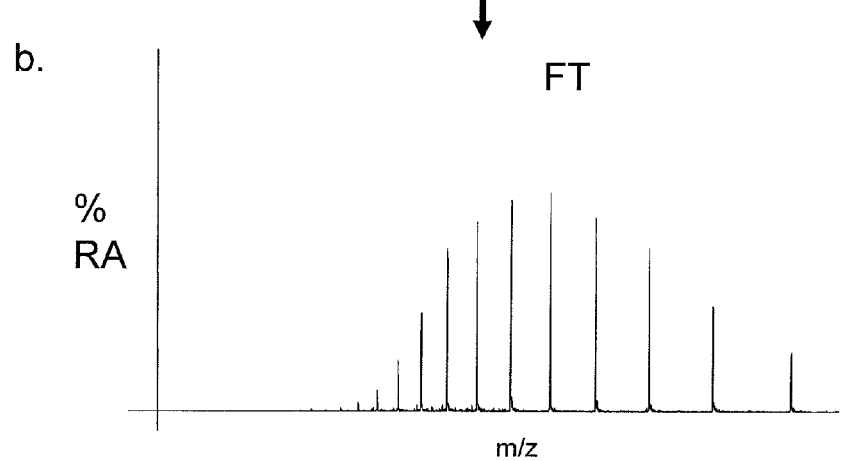

FIGS. 33A and 33B illustrate that the signal over time in (a.) is transformed into a frequency spectrum in FIG. 33B by FFT. The mass spectrum shows the secular frequency components of the ions due to the optical signal transformed into a frequency spectrum or mass spectrum.

Figure 34:
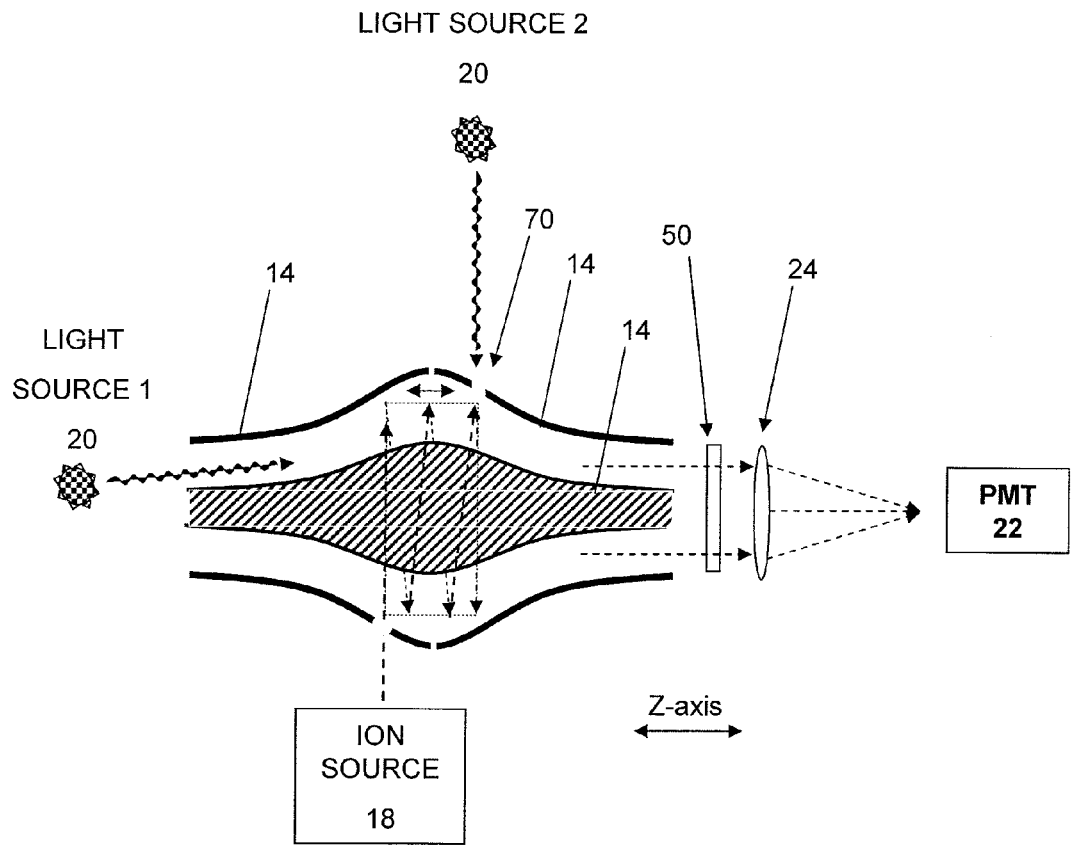
FIG. 34 illustrates another embodiment of an apparatus according to the present invention for an orbitrap mass spectrometer in which the light produced by fluorescence or light scattering is measured over time. Either the circular orbital frequency or the motion along the z-axis {Frequency of axial oscillations=$\omega=[(z/m)k]^{1/2}$} can be measured optically and simultaneously with the induction current measured on the electrodes. Use of the orbital frequency to determine m/z may not be the best embodiment because this frequency is dependent on the initial ion radius and ion velocity. The inside of the orbitrap can be made reflective to photons or the complete electrode can be made to be transparent, yet conductive, so that the maximum number of photons can be captured at a PMT.

FIG. 34 illustrates another embodiment of an apparatus according to the present invention for an orbitrap mass spectrometer in which the light produced by fluorescence or light scattering is measured over time. Either the circular orbital frequency or the motion along the z-axis {Frequency of axial oscillations=$\omega=[(z/m)k]$ ½} can be measured optically, the axial motion is preferred. This optical measurement could occur simultaneously with the induction current measured on the electrodes. Use of the orbital frequency to determine m/z may not be the best embodiment because this frequency is dependent on the initial ion radius and ion velocity. The inside of the orbitrap can be made reflective to photons or the complete electrode can be made to be transparent so that the maximum number of photons can be captured at a PMT 22.

Figure 35:
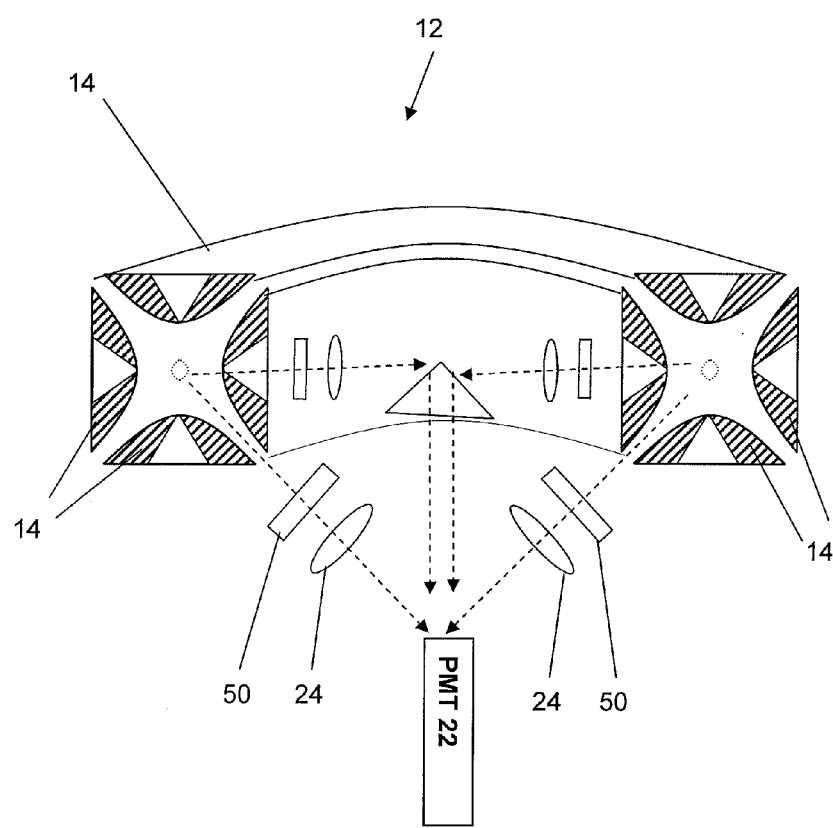
FIG. 35 illustrates the embodiment of an apparatus according to the present invention where a 2D-quadrupole field toroid trap is used to trap the ions while laser diodes could be used as the excitation source. Photons are captured at a PMT after exiting through slots, openings along the asymptotes or through transparent electrodes.

FIG. 35 illustrates the embodiment of an apparatus according to the present invention where a 2D-quadrupole field toroid trap 12 is used to trap the ions while laser diodes could be used as the inhomogeneous excitation source 20 (not shown). Photons are captured at a PMT 22 after exiting through slots, openings along the asymptotes or through transparent electrodes 14.

FIG. 37 illustrates a method of tagging a large protein complex with chromophore molecules so that the m/z can be determine by measuring the LIF and FFT. Light scattering can also be used directly followed by FFT analysis in a LIT 12. In other words, this figure shows optical detection of macromolecules and, in particular, of virus particles.

Figure 38:
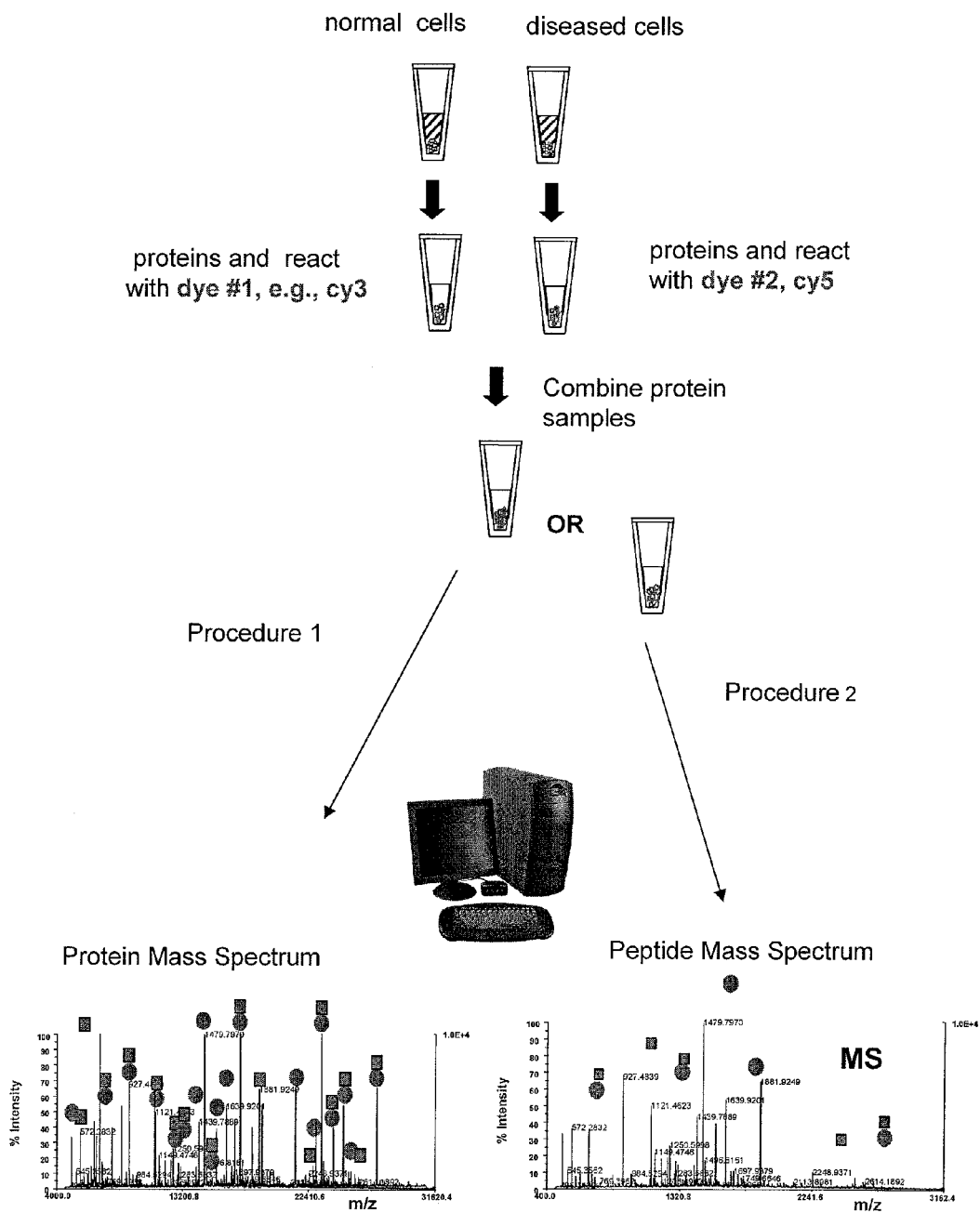
FIG. 38 illustrates a method using LIF where protein regulation from two different cell states is measured by using two different chromophores. The separate protein solutions (diseased cells and normal cells) are react with dye #1, e.g., cy3 and dye #2, cy5 for the normal and diseased states, respectively. The two vials are then combined together two different procedures are followed. In procedure one, the mass and color of each protein are measured directly in an optical mass spectrometer. Differences in the abundance of the same proteins with different colors can be use to determine up or down regulation of protein production and potential be used for disease diagnosis. In procedure two, the dye containing proteins are digested into peptides with trypsin (or other enzyme) and then introduced into a mass spectrometer. Some peptides will have a dye molecule and some will not. By detecting photons emitted in the ion trap and then using a FFT analysis the present invention can be used to determine which peptides contain chromophore 1 or 2 or no chromophore at all and the relative intensity of the two tagged peptides. The present invention can be used to acquire MS data both optically with resolution at R=100,000 and then follow that analysis by convention ion detection as shown in FIG. 2 if desired.

FIG. 38 illustrates a method using LIF where protein regulation from two different cell states is measured by using two different chromophores. The separate protein solutions are combined together and digested into peptides with trypsin (or other enzyme) and introduced into a mass spectrometer. Some peptides will have a dye molecule and some will not. By detecting photons in the ion trap 12 as described herein by FFT the present invention can be used to determine which peptides contain chromophore 1 or 2 or no chromophore at all and the relative intensity of the two tagged peptides. The present invention can acquire MS data both optically with resolution at R>100,000 and then by particle analysis as shown in FIG. 2 if desired.

Figure 39:
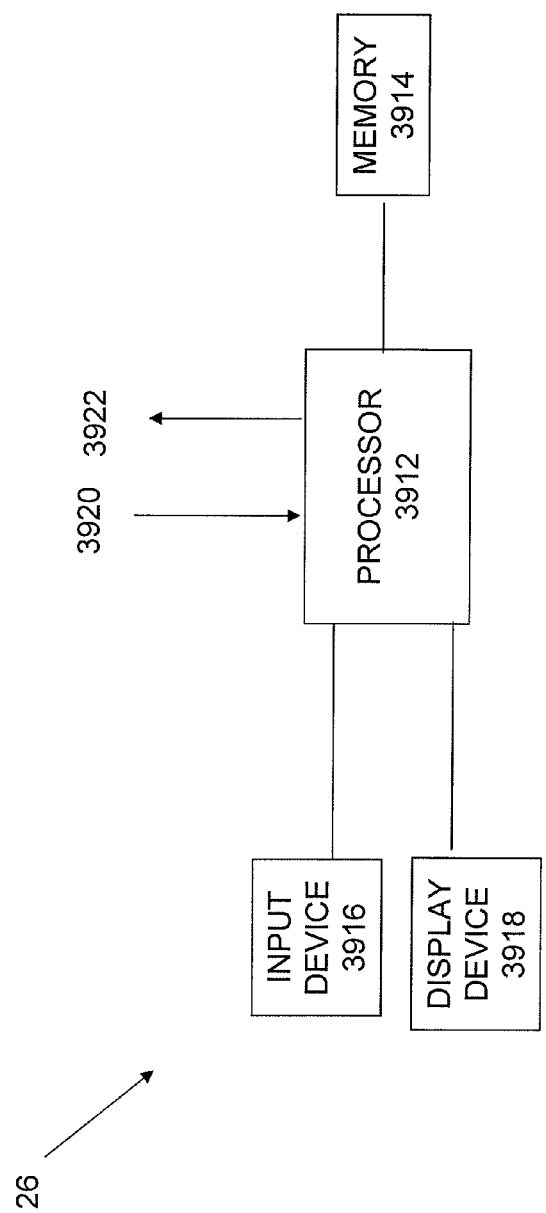
FIG. 39 illustrates one embodiment of the controller 26 according to the present invention.

FIG. 39 illustrates one embodiment of the controller 26 according to the present invention. The controller 26 may include, a processor 3912, memory 3914, an input device 3916, and an output or display device 3918, such as a monitor. The processor 3912 is connected to the memory 3914, the input device 3916, and the output device 3918. The memory 3914 includes computer readable instructions, such as computer hardware, software, firmware, or other forms of computer-readable instructions which, when executed cause the controller 26 to perform certain functions, as described herein. The processor 3912 receives inputs 3920, such as input from the optical detector 22, and provide output 3922, such as control signals to the electrodes 14.

The memory 14 can be any for of computer-readable memory, and may store information in magnetic form, optical form, or other forms. The memory includes computer readable instructions which, when executed, cause the controller 26 to perform certain functions, as described herein. The memory 3914 may be separate from the processor 3912, or the memory 3914 may be integrated with the processor 3912. The memory 3914 may also include more than one memory device, which may be integrated with the processor 3912, separate from the processor 3912, or both.

The input device 3916 may be a keyboard, a touchscreen, a computer mouse, or other forms of inputting information from a user.

The output device 3918 may be a video display or other forms of outputting information to a user.

Many variations of the controller 26 are possible. For example, less than all of the devices illustrated in FIG. 39 may be present. In some embodiments, no input device 3916 and no output device 3918 is present. In that embodiment, input signals 3920 are received and output signals 3922 are generated, but no devices are provided for human interaction because, for example, the process is completely automated. In other embodiments, input 3916 and output 3918 devices are provided. Other variations are also possible.

Figure 40:
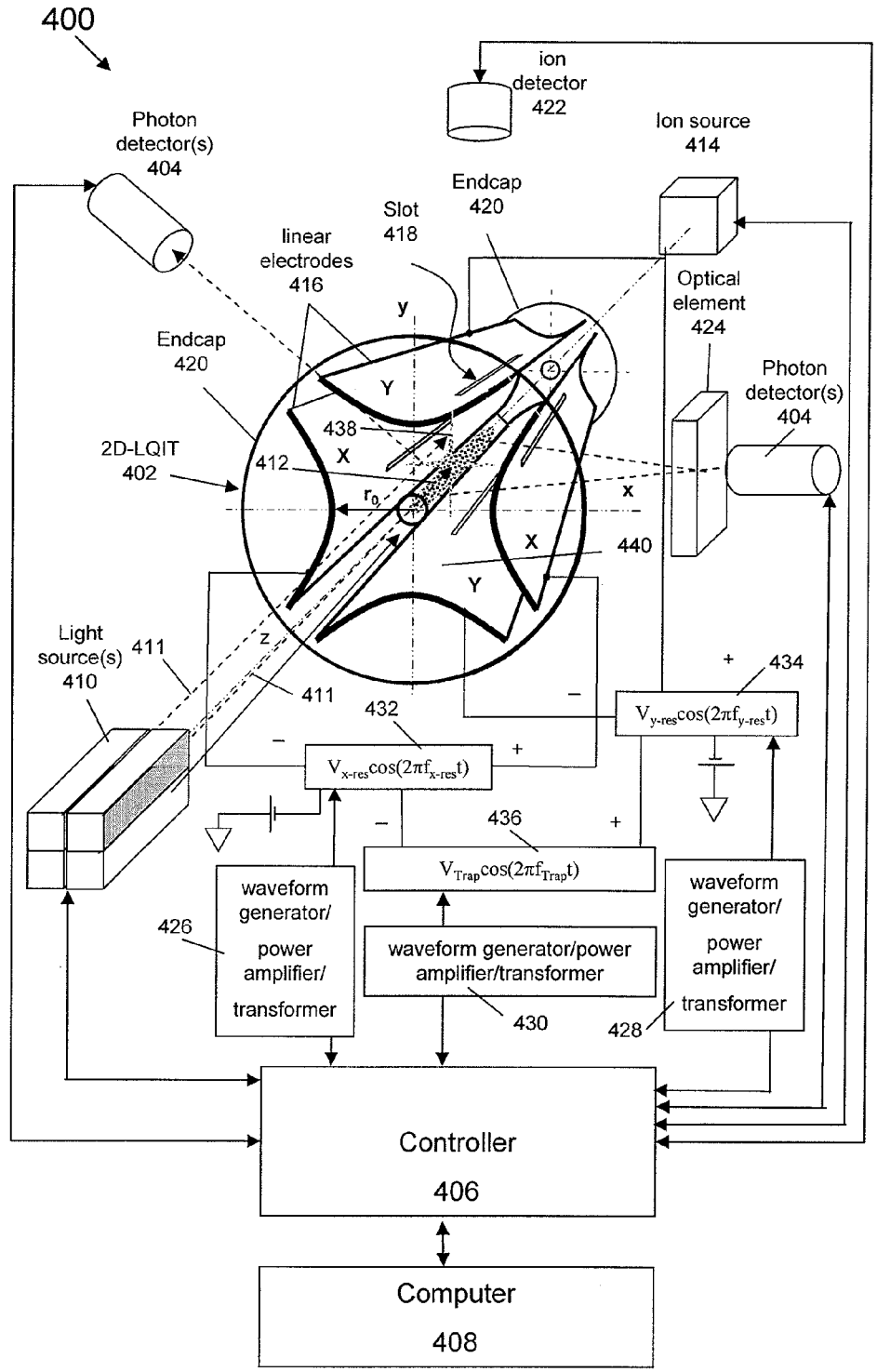
FIG. 40 shows one embodiment using a two-dimensional quadrupole field optical linear ion trap with combined conventional mass analysis using ion ejection and detection and mass analysis incorporating optical detection.

FIG. 40 shows one embodiment using a two-dimensional quadrupole field optical linear ion trap with combined conventional mass analysis using ion ejection and detection and mass analysis incorporating optical detection (LIF, reflection or light scattering). For traditional ion detection a dynode and channel electron multiplier can be used to detect ejected ions radially or axially. For optical detection photons emitted (e.g. by reflection or fluorescence) from photon-excited (e.g., laser-induced) ions are detected using a CCD or PMT (photon detectors). A fast-Fourier transform (FFT) of the time spectrum of the detected photons will produce a frequency spectrum related to the mass-to-charge ratio (m/z) of the ions.

To best excite the ions by photon absorption a laser beam can be focused to expose a portion (non-homogeneous photon excitation) or all of the ion cloud along the z-axis as shown in FIG. 40. Ions may be resonantly excited to larger trajectories thus allowing for improved m/z-analysis, to achieve a better path length for excitation or to move a select mass range into or out of the laser beam for select analyses of mass or frequency of the emitted photon. This type of scan could be called a mass-selective excitation scan incorporating optical detection. For m/z determinations the ions do not have to be ejected from the ion trap and multiple measurements or long measurement times may be achieved. Some systems can allow for simultaneously measurement of the frequency of the ion and the frequency of the photon emitted.

Figure 41A:
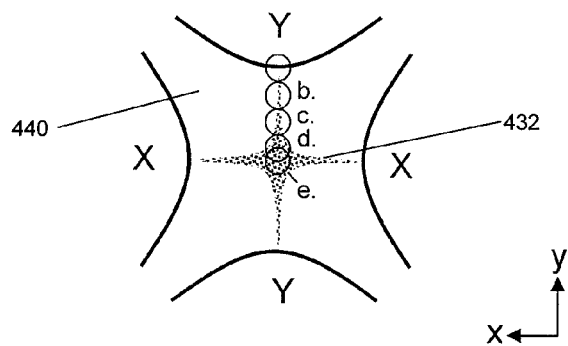
FIGS. 41A and 41B represent cross-sectional images of the electrodes and the ion cloud in the x-y plane expected in the middle of a linear ion trap as shown in FIG. 40.
Figure 41B:
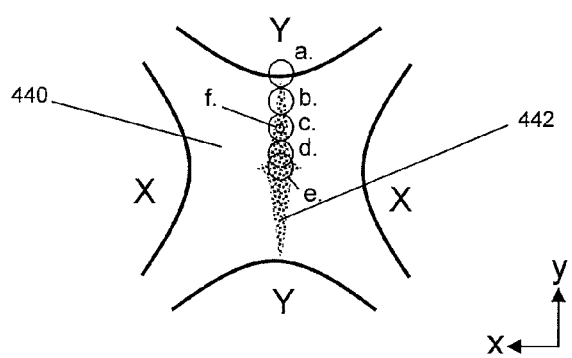

FIGS. 41A and 41B represent cross-sectional images of the electrodes and the ion cloud in the x-y plane expected in the middle of a linear ion trap as shown in FIG. 40. In one example of resonance excitation shown in FIG. 41A, a waveform signal is applied to both the x-rod electrodes and the y-rod electrodes in dipolar fashion in both axes following $V_{u-res} \cos(2\pi f_{u-res} t)$ as shown in the diagram. Ions will resonate at their secular frequency which at low $\beta_u$ can be calculated by $f_{u-res} = \beta_u f_{main}/2$, where u=x or y. At higher $\beta_u$ valued other terms may be needed. The excitation waveform may be tailored-waveform such as a stored-waveform inverse Fourier transform (SWIFT) waveform described by Marshall, Wang and Rica, J. Am. Soc., 1985, 107, 7893-7897) or a single sine wave or a waveform generated by the sum-of-sines to excite a narrow or wide m/z range of ions. Other suitable waveform functions are possible. The waveform could also be applied in a short pulse or multiple pulses as needed. The ions resonating in the x- and y-dimension do not have to be of the same m/z and this will be determined by the resonance excitation frequencies chosen. Thus the excitation waveform may excite all trapped ions or one or more select mass range(s) of interest. In another example, ions may be excited in a single-axis mode of resonance excitation as shown in FIG. 41B. A waveform signal is applied to the y-rods in dipolar fashion following $V_{u-res} \cos(2\pi f_{u-res} t)$ In FIG. 41A resonance excitation waveforms are applied in the x- and y-dimensions, the shape of the ion cross (made up of dots for clarity) will extend outward towards the x and y electrodes as the amplitude of the waveform increases at the secular frequency of the selected ions. The general average shape of the ion cloud (not the individual ion trajectories) could best be described as a four-splined ellipsoid for the LIT. Each spline of the ellipsoid would be in-line with, and pointed to, one of the LIT rods. In short, FIGS. 41A and 41B each represent a slice of the ions from the larger cloud of ions undergoing resonance excitation. (Note that the ion cloud actually extends along the length of the LIT along the z-axis until the trapped ions feel a strong enough repulsive force from the endcaps to be pushed back towards the center. Eventually this z-motion could be damped out due to collisions with a gas like helium.) Under resonance excitation, the ions move to larger orbits towards the electrodes while maintaining a constant frequency. To measure the frequency of these ion while undergoing coherent resonance excitation a laser beam could be positioned for non-homogenously excitation of the ion cloud, for example, at positions (a.) through (f.). Position (e.) is on-axis while position (f.) is overlapping with a smaller subset of the ion cloud. The laser beam is into the plane of the figure. Laser beams cross-sections are typically non-homogenous. In FIG. 41B ions are only resonated in the y-axis while motion in along the x-axis is damped by comparison.

In some cases the optical measurement may be made in only one axis, for example, the x-axis, so as to avoid measuring the $f_{x-res}$ combined with a $f_y$-res measurement. Use of only one axis of excitation so that the measurement is isolated again only in the x-axis may be preferred.

The optical frequency measurement should achieve the best resolution at a low ion abundance and low gas pressure. The ion abundance should be controlled for these optical measurements so that ion-ion (coulomb) repulsion is kept to a minimum. Low pressures can be obtained by using a pulse valve which would allow for the optical measure to be made after the damping gas has pumped to a low pressure.

FIGS. 42A through 42H show tailored waveform frequency-domain spectra of the intensity (i) for the waveform frequencies applied to the x- and or y-rods, respectively. In the following examples, all waveforms (SWIFT or otherwise) can be altered and pulsed as needed. FIGS. 42A and 42B show the case the ions of different m/z receive the same amplitude of excitation. For example, a high m/z ion (might resonated only into the (d.) region while a low m/z ion might resonate into the laser beam region (c.) of FIG. 41 and so on. A notch in the frequency spectrum of FIG. 42D. is shown as an example where select m/z of ions are not resonated at all by the supplementary excitation waveform.

FIG. 42C and FIG. 42D show the frequency spectra where the waveform is synthesized to have less amplitude at lower m/z (higher frequency). This waveform could be used to cause the ions of both high and low m/z to resonate to the same region in the cross-section, for example, into laser beam region (c.) for simultaneous analysis. This would allow for mass analysis multiplexing by allowing all m/z ions to undergo LIF and photon detection simultaneously.

In FIGS. 42E and 42F, different mass ranges are resonantly excited in the x- or y-dimension, respectively, and with different amplitudes as discussed above. Ions above a selected m/z and higher would be resonated in the y-direction in this example.

In FIGS. 42G and 42H, is an example of a narrow band of frequencies (m/z range of ions) that could be resonated into the x- or y-directions. This narrow band could be shifted to a higher or a lower band and a new pulse applied as desired. Additionally, a frequency scan or "chirp" could be applied to scan from a low to higher frequencies over a short period of time to pass through the resonance frequency of all ions selected (not shown).

In all the examples above, the experimental parameters for the resonance excitation waveforms must be set up to stay below the threshold for ion fragmentation or ejection or annihilation on the electrode surface unless that result is desired. Too great of an amplitude could cause fragmentation due to collisions with gas. The frequency domains shown in FIGS. 42A-H can be generated using stored-waveform inverse Fourier transform technology (SWIFT).

The function of resonating ions to achieve coherence and to move them to outer regions of the trapping chamber (e.g., a. thru d.) can have advantages for improved optical measurements (photon detection) and improved photon absorption.

Figure 42:
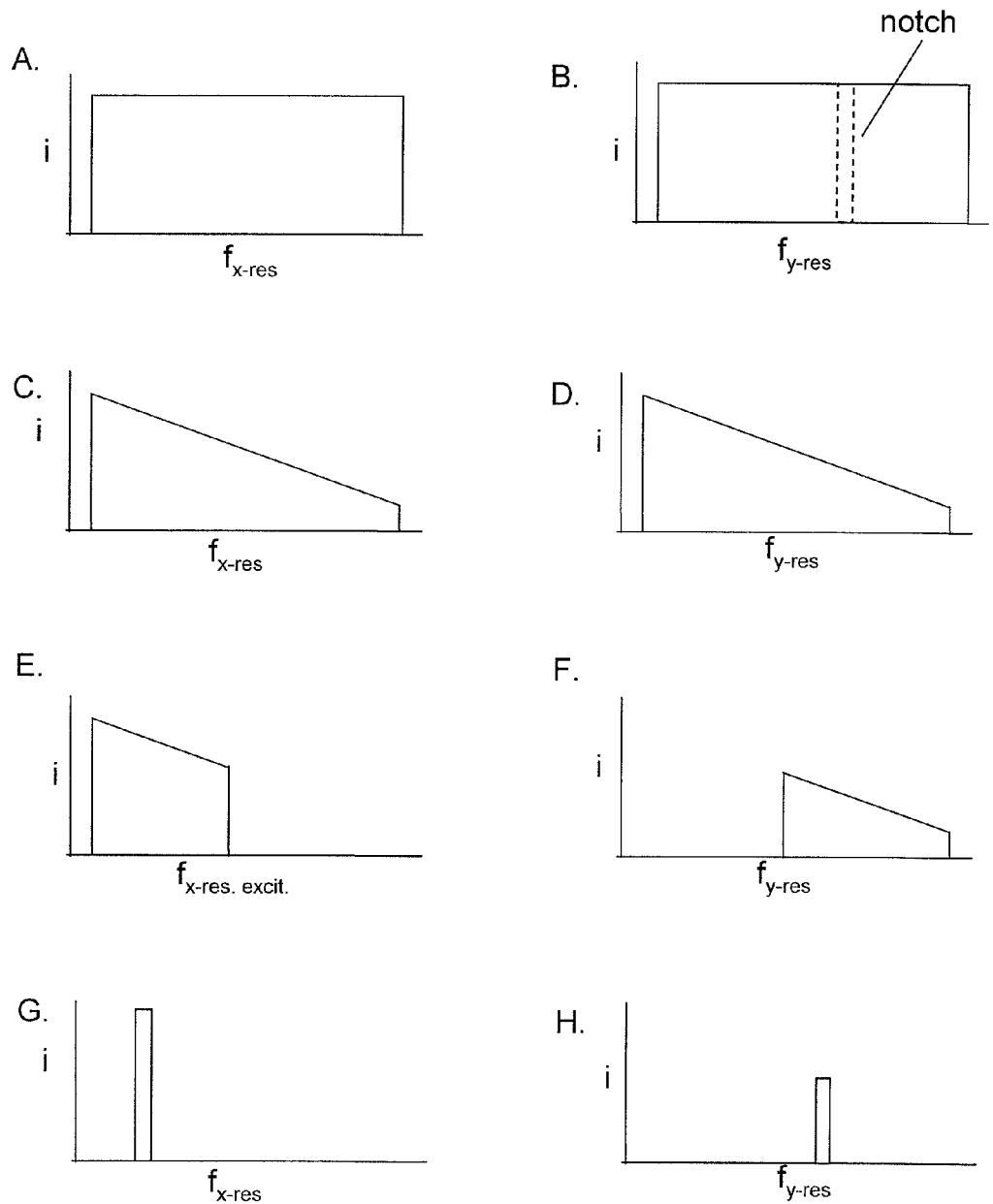
FIGS. 42A and 42B shows frequency spectra for the intensity of the waveform frequencies applied to the x- or y-rods, respectively.
FIG. 42C and FIG. 42D show the frequency spectra where the waveform is synthesized to have less amplitude at lower m/z (higher frequency).
FIGS. 42E and 42F illustrate different mass ranges are resonantly excited in the x- or y-dimension, respectively, and with different amplitudes as discussed above.
FIGS. 42G and 42H illustrate examples of a narrow band of frequencies (m/z range of ions) that could be resonated into the x- or y-directions and this range of frequencies can be scanned to higher or lower frequencies as required.

Examples of features or functions of the present invention illustrated in FIGS. 40-42 and text are: (i) Ions can resonated in x- and or y-directions for measurement purposes; (ii) A mixture of ions over a wide m/z range may be trapped at the same time for the analysis; (iii) An image is not necessary for m/z determination by the above method; (iv) Resonating ions to large trajectories for a larger cross-sectional field has potential optical advantages, but you must resonate the ions without imparting too much internal energy deposition to cause fragmentation; (v) In one example, a resonance signal is applied between two opposite rods to increase the size of the trapped orbits; (vi) In some cases ions may not undergo photon excitation until they are resonated into the excitation light source (laser beam); (vii) Ions can be moved along the operating line in the stability diagram into resonance at a higher frequency as in an amplitude scan to achieve the best resolution at high q; and (viii) Ions can be measured where they are moving the slowest while trapped (near the electrode) and thus would be most likely to be excited in the laser beam due to long exposure times.

Figure 43:
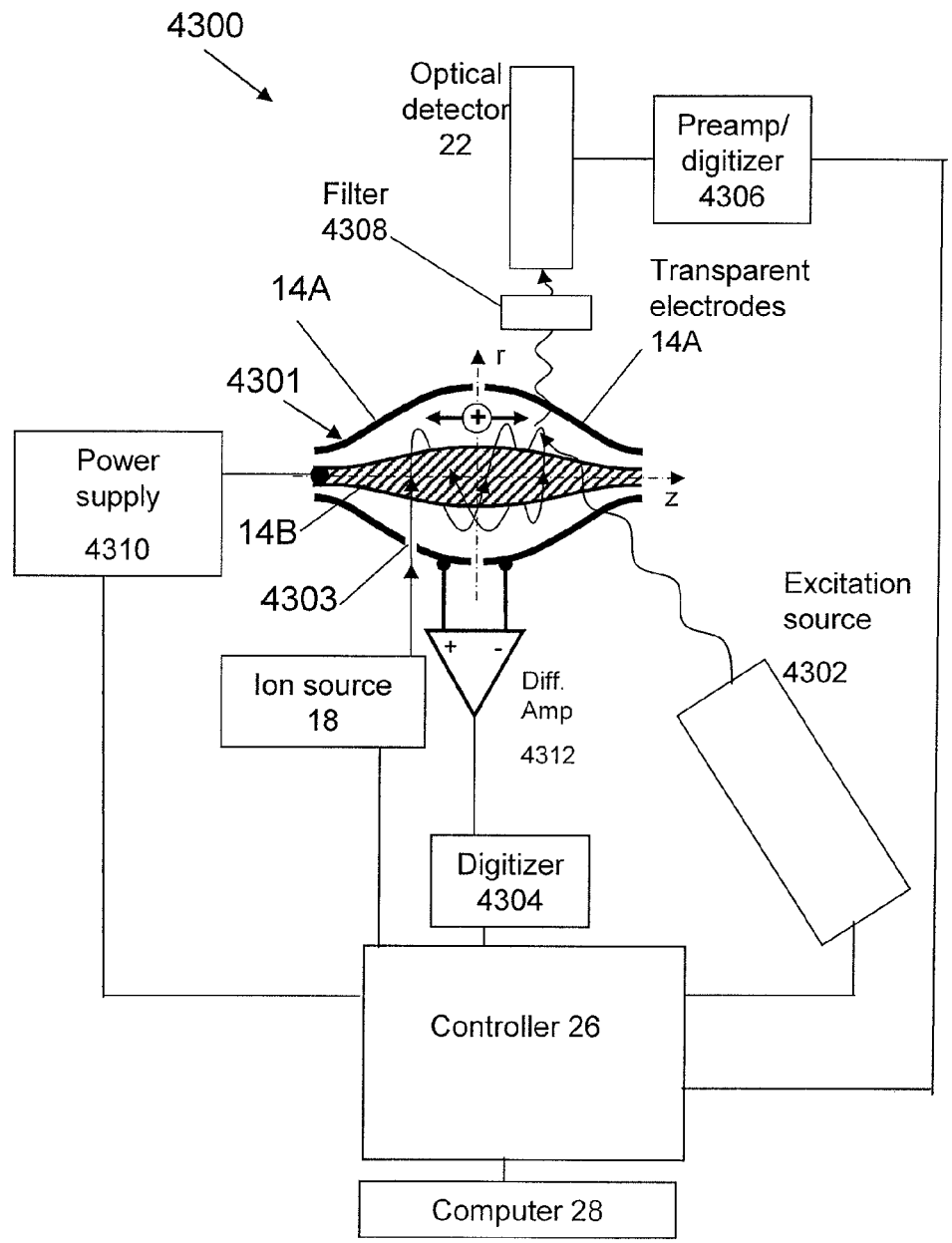
FIG. 43 illustrates another embodiment of an apparatus according to the present invention for an orbitrap mass spectrometer in combination with other system components.

Illustrated in FIG. 43 is an optical orbitrap mass spectrometer 4300 with exemplary components of one embodiment. Any conventional ion source 18, such as an electron ionization, chemical ionization, atmospheric pressure ionization and others of the like, can produce the ions for ion injection into the optical orbitrap 4301. These ions are injected into the device through an aperture 4304 in one of the outside split barrel electrodes 14A and will become trapped by orbiting around the spindle electrode 14B. The ions orbit coherently with no additional excitation waveform. The spindle electrode 14B has a DC potential that is ramped before and during injection until all the ions are trapped and this causes the radius of the ion orbits to decrease. For mass analysis, an image current is measured on the outer split barrel electrodes 14A using a differential amplifier 4312. This time-domain signal is digitized by digitizer 4304 and is then Fourier transformed into a frequency spectrum related to the m/z of all of the ions. For the optical ion trap 4300, the additional hardware of an excitation source 4302 (such as a laser), an optical detector 22 (such as a PMT), and the respective preamps and digitizers 4306 required to measure the photon signal are shown in FIG. 43. For both the image current case and the optical case the axial motion of the ions is measured. In one example, photons from the laser 4302 excite the ions at one end of the device and the photon emission frequency is detected at the optical detector 22. The optical signal measured in the time-domain is Fourier transformed into a frequency spectrum directly related to the m/z of the ions. The same mass analysis equation noted earlier can be used for this conversion to m/z. The optical detector 22 could have a filter 4308 in place so that it detects only a select range of photon frequencies (e.g., colors). A more elaborate optical detector 22 setup could use a monochromater or similar device in front of a PMT to determine the photon frequency. Simultaneous optical and image current m/z analysis and photon frequency analysis can occur. A controller 26 and computer 28 can be used to control the components of the system and acquire the data.

Figure 44:
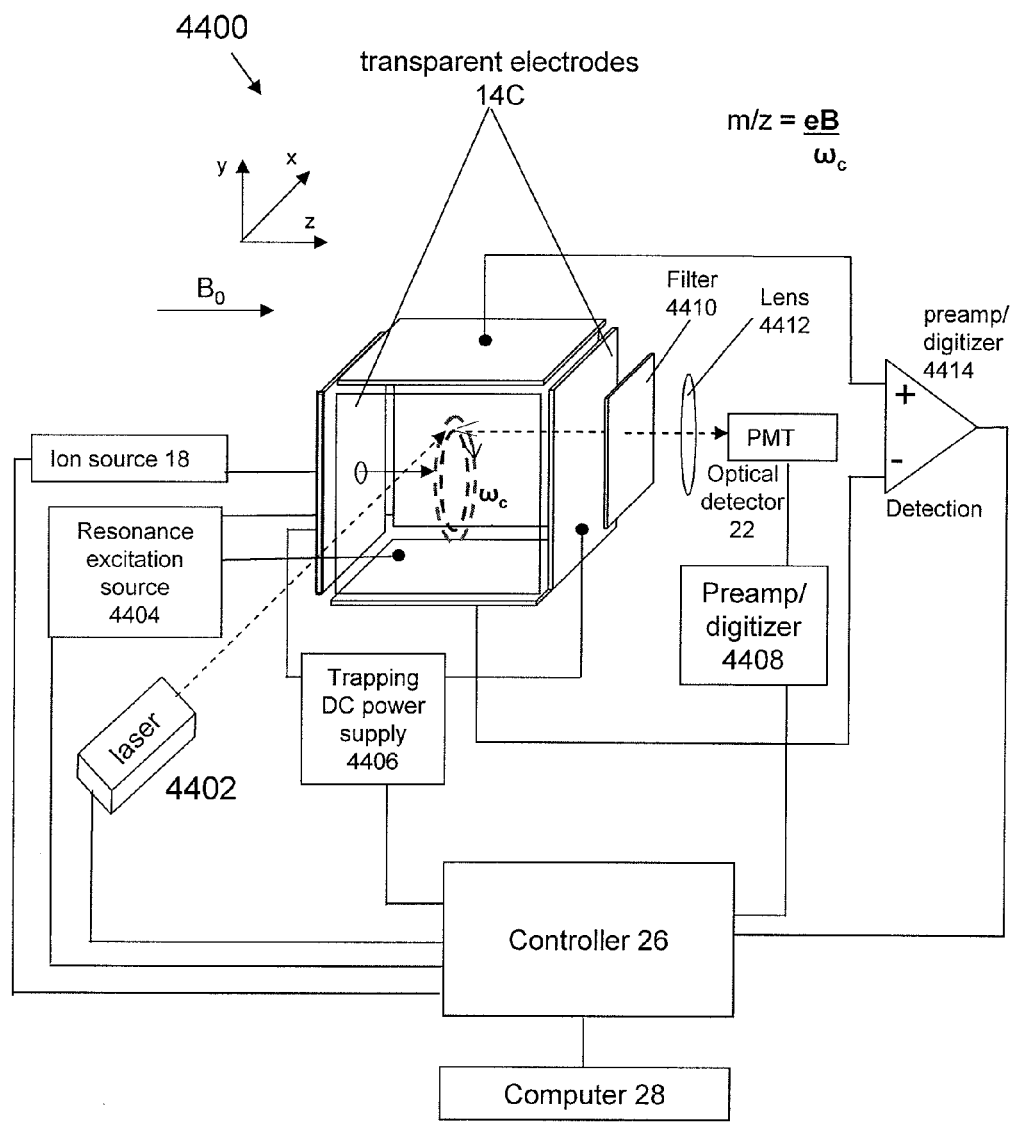
FIG. 44 is an illustration of a Fourier Transform mass spectrometer (FTMS) in combination with other system components.

In FIG. 44 is shown an optical Fourier transform ion cyclotron resonance mass spectrometer (FTICR MS) or FTMS 4400. An ion source 18 provides the ions that may be trapped between the six electrodes 14C. A magnetic field $B_0$ is provided so the ions undergo a cyclotron orbit. A DC trapping power supply 4406 provides trapping field in the z-axis. A resonance excitation waveform such as a tailored SWIFT waveform (Marshall, Wang, Ricca, *JACS*, 1895, 107, 7893-7897.) can be applied to the two x-electrodes to provide coherence of the ion motion of the same m/z and larger orbits. This coherence and large orbits allow for an image time-domain signal to be measured on detection plates by a differential amplifier. A fast Fourier transform converts the time-domain signal into a frequency spectrum which can be converted to m/z spectrum. A laser 4402 can be used as a photon source that can be directed through a transparent electrode 14C or an electrode with an aperture, to overlap with the cyclotron orbits so that the ions will become excited and emit a photon by florescence or other means. The photon emission frequency is detected at the optical detector PMT 22. The optical signal measured in the time-domain is Fourier transformed into a frequency spectrum directly related to the m/z. The same mass analysis equation noted earlier for FTICR can be used for this conversion to m/z. The optical detector 22 could have a filter 4410 in place so that it detects only a select range of photon frequencies (e.g., colors). Note that the optical detector 22 is positioned parallel to the z-axis of the orbits to limit the Doppler effect on the measurement. A controller 26 and computer 28 can be used to control the components of the system and acquire the data.

FIGS. 45A, 45B, and 45C show another embodiment 4500 of the invention a multi-pass light beam from an excitation source such as a laser 4504. The laser beam is traversing the chamber of a linear ion trap 15X in FIG. 45A, and 28X in FIGS. 45B and 45C (viewed down the z-axis). In each example, mirrored surfaces 4514, which could also serve as ion lenses, reflects the light back and forth through the ion cloud 4506 for maximum exposure of the ions. The ions may or may not be undergoing resonance excitation during exposure. Apertures 4508 or transparent electrodes can allow for the laser light to pass into and out of the ion trap chamber 4514. A light sink 4508 could be used to prevent backscattering of photons. The apparatus could be used for both LIF or for improved photo-induced dissociation by allowing for an increased number of excitations per pass.

The present invention has been described in terms of particular examples. However, these examples are illustrative and not limiting, and other variations and modifications of the present invention are contemplated. For example, although aspects of the present invention has generally been described in terms of using two-dimensional quadrupole field ion traps, the present invention may also be used with three-dimensional quadrupole field ion traps, with orbitraps, and with other ion traps. Similarly, although some embodiments are illustrated as using a particular types of devices, other devices may also be used. Those and other variations, modifications, and combinations of the present invention are possible and contemplated, and it is intended that the foregoing specification and the following claims cover such modifications and variations.

What is claimed is:

1. A method of frequency or mass-to-charge ratio (m/z) analysis comprising the steps of:
   injecting ions into an ion trap mass spectrometer;
   applying one or more trapping waveform signals to the ion trap to retain the ions inside the ion trap, wherein each ion of the ions has an initial orbit;
   applying one or more resonance excitation waveform signals to the ion trap to resonate a portion of the ions into a different orbits in the ion trap;
   exciting the portion of ions in the different orbits to emit photon signals;
   detecting and acquiring a time-domain photon signal of frequencies of the portion of the ions in the different orbits in the ion trap; and
   applying fast Fourier transform analysis to obtain the frequency spectrum related to a plurality of m/z ratios of the portion of the ions.

2. The method according to claim 1, wherein the step of exciting the portion of ions in the different orbits to emit photon signals comprises a step of exposing the portion of ions to photons to allow for reflection or scattering of the photons.

3. The method according to claim 1, wherein the step of exciting the portion of ions in the different orbits to emit photon signals comprises a step of exposing the portion of ions to photons to allow for fluorescence from the ions.

4. The method according to claim 1, wherein the one or more resonance excitation waveform signals is capable of exciting all ions in the ion trap.

5. The method according to claim 1, wherein the one or more resonance excitation waveform signals is capable of exciting the portion of the ions in one or more predetermined mass range or ranges.

6. The method according to claim 1, wherein the one or more resonance excitation waveform signals is capable of exciting the portion of the ions in one or more predetermined axis.

7. The method according to claim 1, wherein the step of applying the one or more resonance excitation waveform signals comprises generating a resonance excitation frequency from about 10 GHz to about 1 Hz or about 1 Hz to about 10 GHz.

8. The method according to claim 1, wherein the step of detecting the frequencies of the emitted photon signal comprises orienting an energy source off—a centerline (off-centerline) of the ion trap, whereby energy emitted from the energy source is aimed in the direction of the different orbits to excite ions in the different orbits.

9. The method according to claim 8, wherein the step of orienting the energy source further comprises orienting a plurality of energy sources off-centerline.

10. The method according to claim 1, wherein the step of detecting the frequencies of the emitted photon signal comprises a step of orienting an energy source on—a centerline (on-centerline) of the ion trap, whereby energy emitted from the energy source is aimed in the direction of the centerline to excite ions along the centerline.

11. The method according to claim 8, wherein the step of orienting the energy source off-centerline further comprises the step of orienting the off-centerline energy source parallel with the centerline of the ion trap.

12. The method according to claim 9, wherein the step of exciting the portion of ions in the different orbits further comprises a step of simultaneously actuating the plurality of energy sources for simultaneous measurement of the frequencies of the emitted photon signals.

13. The method according to claim 1, wherein the step of applying the one or more trapping waveform signals comprises the step of increasing an amplitude of the one or more trapping waveform signals to higher voltages in a step wise fashion, wherein fast Fourier transform analysis is taken of the time-domain emitted photon signal at each amplitude.

14. The method according to claim 1, wherein the step of applying one or more resonance excitation waveform signals to the ion trap to resonate the ions to the different orbits comprises a step of applying a waveform to an x-pair or a y-pair electrodes such that the portion of the ions in the ion trap resonate at secular frequencies in an x-direction and/or a y-direction, respectively.

15. The method according to claim 1, wherein the step of detecting further comprises a step of determining the photon frequency at each m/z.

16. The method according to claim 15, wherein the step of detecting further comprises a step of determining the frequencies of the emitted photons simultaneously with the step of determining the photon frequency.

17. A method of mass-to-charge ratio (m/z) analysis comprising the steps of:
injecting ions into a Fourier transform-based ion trap mass spectrometer;
applying one or more waveform signals to the ion trap to cause the ions to be trapped and to follow orbits in the ion trap;
exciting a portion of the ions in the orbits to emit photons;
detecting and acquiring a time-domain photon signal of frequencies of the portion of the ions in the orbits in the ion trap; and
applying fast Fourier transform analysis to the time-domain photon signal to obtain a frequency spectrum related to a m/z of the portion of the ions in the orbits.

18. The method according to claim 17, wherein the mass spectrometer is an orbitrap mass spectrometer.

19. The method according to claim 17, further comprising the step of measuring a frequency of the emitted photon.

20. The method according to claim 17, further comprising the step of measuring a charge induced time-domain signal and applying fast Fourier transform analysis to obtain another frequency spectrum.

21. The method according to claim 20, wherein the steps of obtaining the frequency spectrum and the another frequency spectrum are executed simultaneously.

22. The method according to claim 17, wherein the frequencies detected are axial frequencies.

23. The method according to claim 17, wherein the mass spectrometer is a Fourier transform ion cyclotron resonance (FT ICR) mass spectrometer.

24. The method according to claim 23, further comprising the step of applying a tailored waveform signal to the FT ICR, wherein the tailored waveform signal is a stored waveform inverse Fourier transform (SWIFT) waveform to cause the ions to be in resonance, and coherent, and to move from initial cyclotron orbits to different cyclotron orbits.

25. An orbitrap mass spectrometer for frequency or mass-charge ratio (m/z) analysis comprising:
an ion source;
an optical orbitrap having a plurality of electrodes and an aperture, wherein the ions produced by the ion source are injected into the optical orbitrap through the aperture;
an excitation source juxtaposition to the optical orbitrap to excite a portion of the ions trapped in the optical orbitrap to emit photons;
a detector juxtaposition to an electrode of the plurality of electrodes to detect photon emission frequencies emitted from the portion of the ions;
a preamp/digitizer in electrical communication with the detector to digitize a time-domain photon signal of frequencies of the portion of the ions; and
a computer electrically connected to the preamp/digitizer (i) to receive the time-domain signal of the ions, and (ii) to perform a Fourier transform of the time-domain signal into a frequency spectrum related to m/z for the portion of the ions.

26. A Fourier transform ion cyclotron resonance mass spectrometer for frequency or mass-charge ratio (m/z) analysis comprising:
an ion source;
a Fourier transform ion cyclotron resonance mass spectrometer (FTMS) having a plurality of electrodes and an aperture, wherein the ions produced by the ion source are injected into the FTMS through the aperture;
a waveform generator electrically connected to the FTMS to apply a resonance excitation waveform to at least one electrode of the plurality of electrodes to provide coherence of the ions and to resonate the ions having the same m/z;
a photon source directed towards the FTMS to overlay cyclotron orbits of the ions trapped in the FTMS to excite the ions;
a detector juxtaposition to an electrode of the plurality of electrodes to detect the photon emission frequency of the emitted photons from the ions;
a preamp/digitizer in electrical communication with the detector to digitize a time-domain photon signal of frequencies of the ions; and
a computer electrically connected to the preamp/digitizer (i) to receive the time-domain signal of the ions, and (ii) to perform a Fourier transform of the time-domain signal of the ions into a frequency spectrum related to m/z for the portion of the ions.

27. The orbitrap mass spectrometer according to claim 25, wherein one or more electrodes of the plurality of electrodes is a solid transparent electrode.

28. The Fourier transform ion cyclotron resonance mass spectrometer according to claim 26, wherein one or more electrodes of the plurality electrodes is a solid transparent electrode.

* * * * *

UNITED STATES PATENT AND TRADEMARK OFFICE
CERTIFICATE OF CORRECTION

| | |
|---|---|
| PATENT NO. | : 8,395,112 B1 |
| APPLICATION NO. | : 12/898264 |
| DATED | : March 12, 2013 |
| INVENTOR(S) | : Mark E. Bier |

It is certified that error appears in the above-identified patent and that said Letters Patent is hereby corrected as shown below:

In the Specification

In Column 1, Line 19, regarding the Statement Regarding Federally-Sponsored Research should be inserted to read:
--Statement Regarding Federally-Sponsored Research
This invention was made with United States government support under grant number DBI0454980 awarded by the National Science Foundation. The U.S. government has certain rights in the invention.--

Signed and Sealed this
Twenty-fifth Day of April, 2023

Katherine Kelly Vidal
*Director of the United States Patent and Trademark Office*